(12) United States Patent
Sekiya et al.

(10) Patent No.: US 8,399,204 B2
(45) Date of Patent: Mar. 19, 2013

(54) METHOD FOR SCREENING OF SUBSTANCE WHICH ALTER GPR120-MEDIATED CELL-STIMULATING ACTIVITIES

(75) Inventors: Tomoko Sekiya, Tsukuba (JP); Norimasa Miyamoto, Ibaraki-Ken (JP); Hirokazu Tanaka, Chiba-Ken (JP); Naoko Massaki, Ibaraki-Ken (JP)

(73) Assignee: Eisai R&D Management Co., Ltd., Tokyo-To (JP)

( * ) Notice: Subject to any disclaimer, the term of this patent is extended or adjusted under 35 U.S.C. 154(b) by 699 days.

(21) Appl. No.: 11/991,441

(22) PCT Filed: Sep. 1, 2006

(86) PCT No.: PCT/JP2006/317331
§ 371 (c)(1),
(2), (4) Date: Mar. 17, 2009

(87) PCT Pub. No.: WO2007/026874
PCT Pub. Date: Mar. 8, 2007

(65) Prior Publication Data
US 2011/0183318 A1    Jul. 28, 2011

(30) Foreign Application Priority Data
Sep. 2, 2005 (JP) ................................ 2005-254643

(51) Int. Cl.
*G01N 33/53* (2006.01)
*G01N 33/567* (2006.01)
(52) U.S. Cl. ......................................... 435/7.2; 435/975
(58) Field of Classification Search .................. None
See application file for complete search history.

(56) References Cited

U.S. PATENT DOCUMENTS
6,835,380 B2 * 12/2004 Horwitz et al. ............. 424/141.1
2003/0022186 A1   1/2003 Feder et al.

FOREIGN PATENT DOCUMENTS
| JP | 2001-211885 | | 2/2000 |
| JP | 2005-015358 | A | 1/2005 |
| JP | 2005-110658 | A1 | 4/2005 |
| WO | WO-00/00611 | A2 | 1/2000 |
| WO | WO-00/50596 | A3 | 8/2000 |
| WO | WO2004/065960 | * | 8/2004 |

OTHER PUBLICATIONS

Grandison L. Endocrinology 114(1):1-7, 1984.*
Katsuma et al., "Free Fatty Acids Inhibit Serum Deprivation-induced Apoptosis through GPR120 in a Murine Enteroendocrine Cell Line STC-1", J. Biol. Chem., vol. 280, No. 20, pp. 19507-19515, May 2005.
Hirasawa et al., "Free Fatty acids regulate gut incretin glucagon-like peptide-1 secretion through GPR120", Nature Medicine, vol. 11, pp. 90-94, Jan. 2005.
Fredriksson et al., "Seven evolutionarily conserved human rhodopsin G protein-coupled receptors lacking close relatives", FEBS Letters, vol. 554, pp. 381-388, 2003.
Xing et al., "Protein Kinase C-dependent Activation of Cytosolic Phospholipase $A_2$-Adrenergic Receptors in Madin-Darby Canine Kidney Cells", J. Clin. Invest., vol. 97, No. 5, pp. 1302-1310, 1996.
Lee et al., "The Inducible G Protein-coupled Receptor *edg-1* Signals via the Gi/Mitogen-acivated Protein Kinase Pathway", J. Biol. Chem., vol. 271, No. 19, pp. 11272-11279, 1996.
Ikeno et al., "Secretory Phospholipase $A_2$ Induce Neurite Outgrowth in PC12 Cells through Lysophosphatidylcholine Generation and Activation of G2A Receptor", J. Biol. Chem., vol. 280, No. 30, pp. 28044-20852, Jul. 2005.
Cockcroft S et al:, The Biochemical Journal, 263(3); 715-723 (1989).
Sonoda Hirofumi et al., The Journal of Biological Chemistry, 277(37); 34254-34263 (2002).
Supplementary European Search Report, EP 06797273, dated Feb. 10, 2009.
Notification of Reason for Rejection from Japan Patent Application No. 2007-533357, dated Jul. 29, 2011. Translation enclosed.
Argument from Japan Patent Application No. 2007-533357, dated Sep. 27, 2011. Translation enclosed.
Amendment from Japan Patent Application No. 2007-533357, dated Sep. 27, 2011. Translation enclosed.
Communication pursuant to Article 94(3) EPC from European Patent Application No. 06797273.7, dated May 5, 2011.
Response to Communication pursuant to Article 94(3) EPC from European Patent Application No. 06797273.7, Nov. 15, 2011.
Muhl et al., "PDGF Suppresses the Activation of Group II Phospholipase $A_2$ Gene Expression by Interleukin 1 and Forskolin in Mesangial Cells," FEBS 291:249-252, 1991.
Zanassi et al., "cAMP-Dependent Protein Kinase Induces cAMP-Response Element-Binding Protein Phosphorylation via an Intracellular Calcium Release/ERK-Dependent Pathway in Striatal Neurons," J. Biol. Chem. 276:11487-11495, 2001.

* cited by examiner

*Primary Examiner* — Robert Landsman
(74) *Attorney, Agent, or Firm* — Clark & Elbing LLP

(57) ABSTRACT

The present invention provides a screening method for determining whether a substance of interest is a substance which alters GPR120 mediated cell stimulating activities, comprising using a substance of interest, a biomembrane containing GPR120, or cells containing said biomembrane, and phospholipase or salts thereof. According to a screening method of the present invention, the method can screen substances such as CCK and GLP-1 which are involved in the secretion of hormones in gastrointestinal tracts.

9 Claims, 27 Drawing Sheets

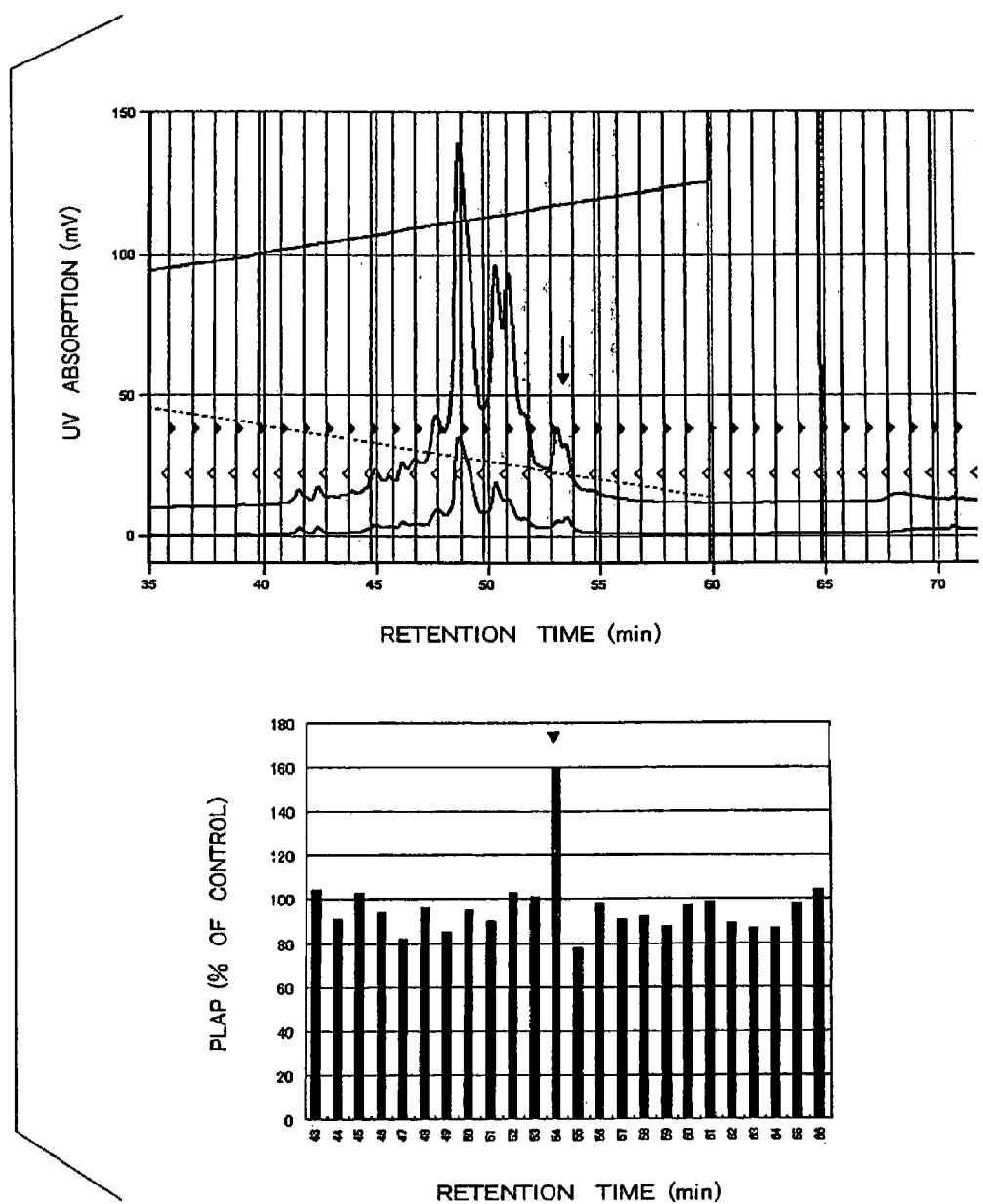
F I G. 6A

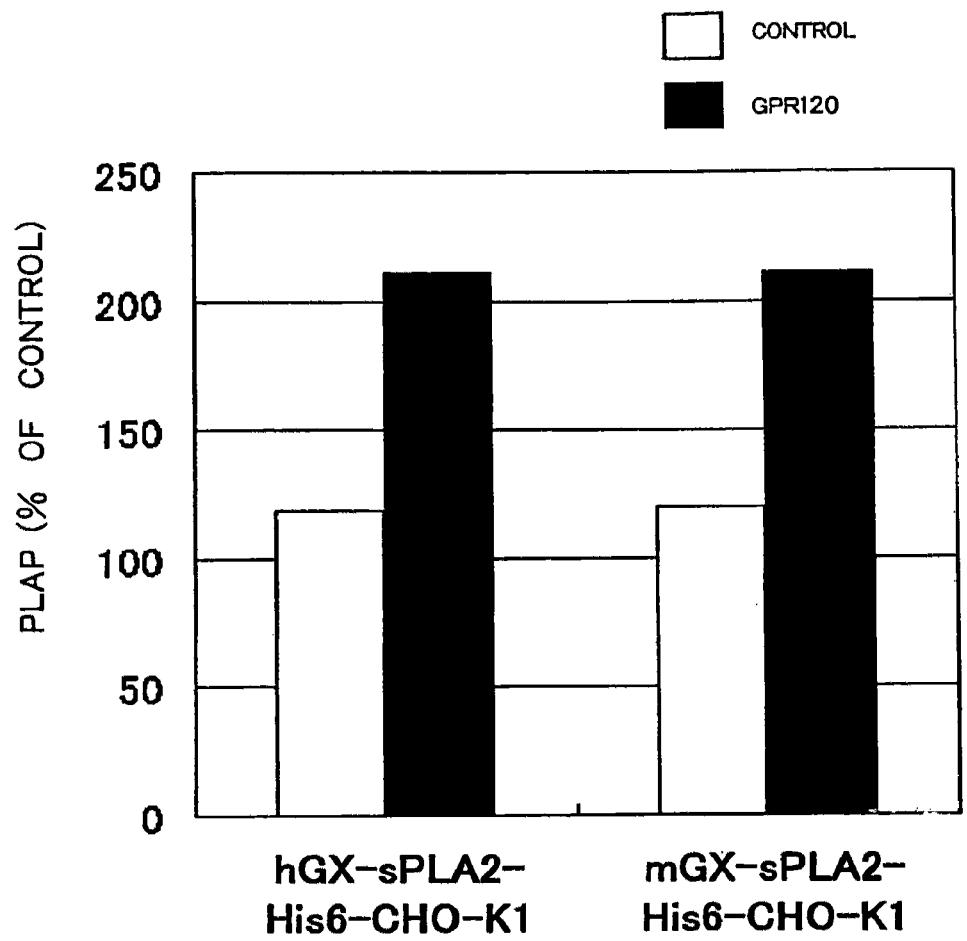
F I G. 7

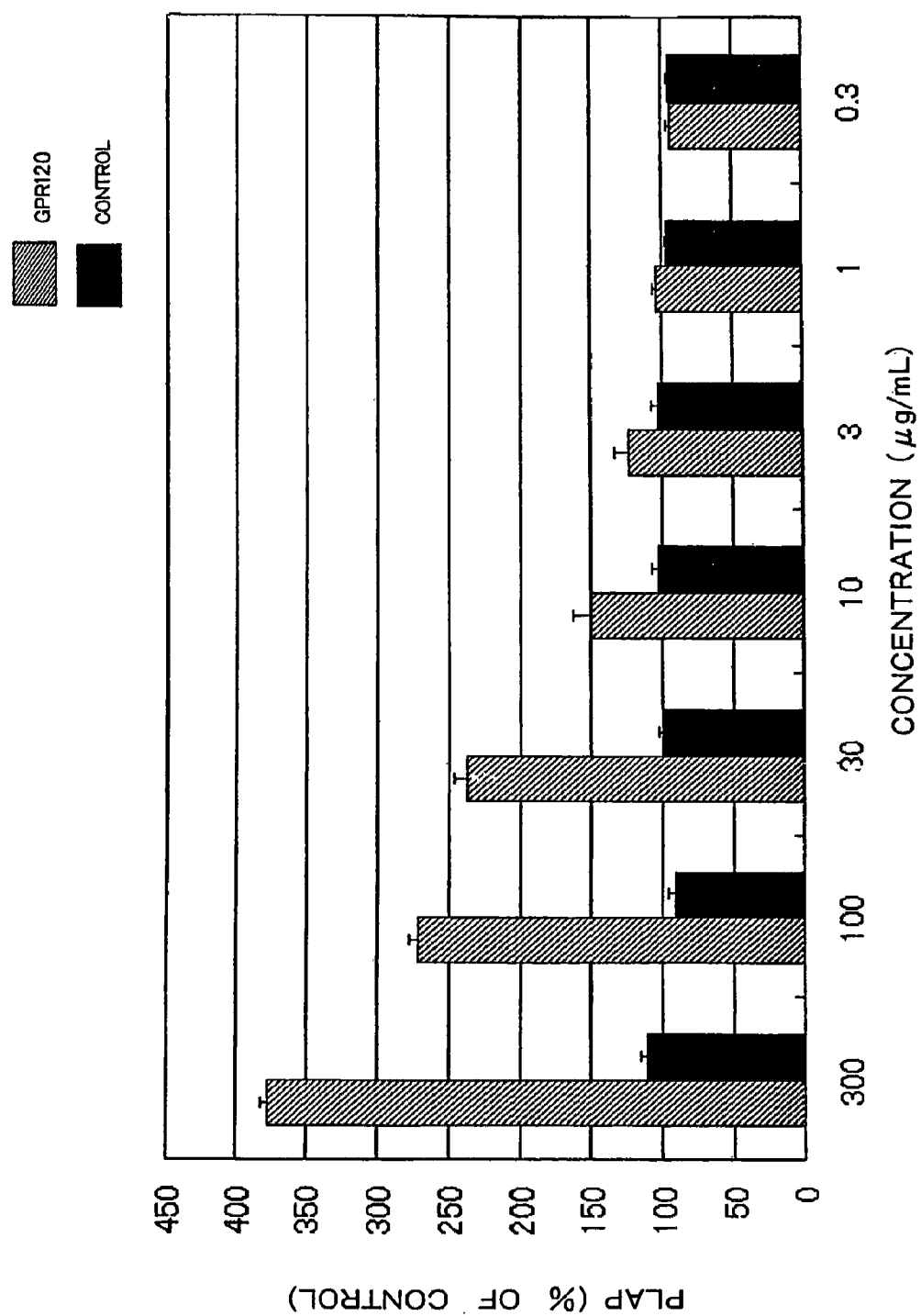
F I G. 10B

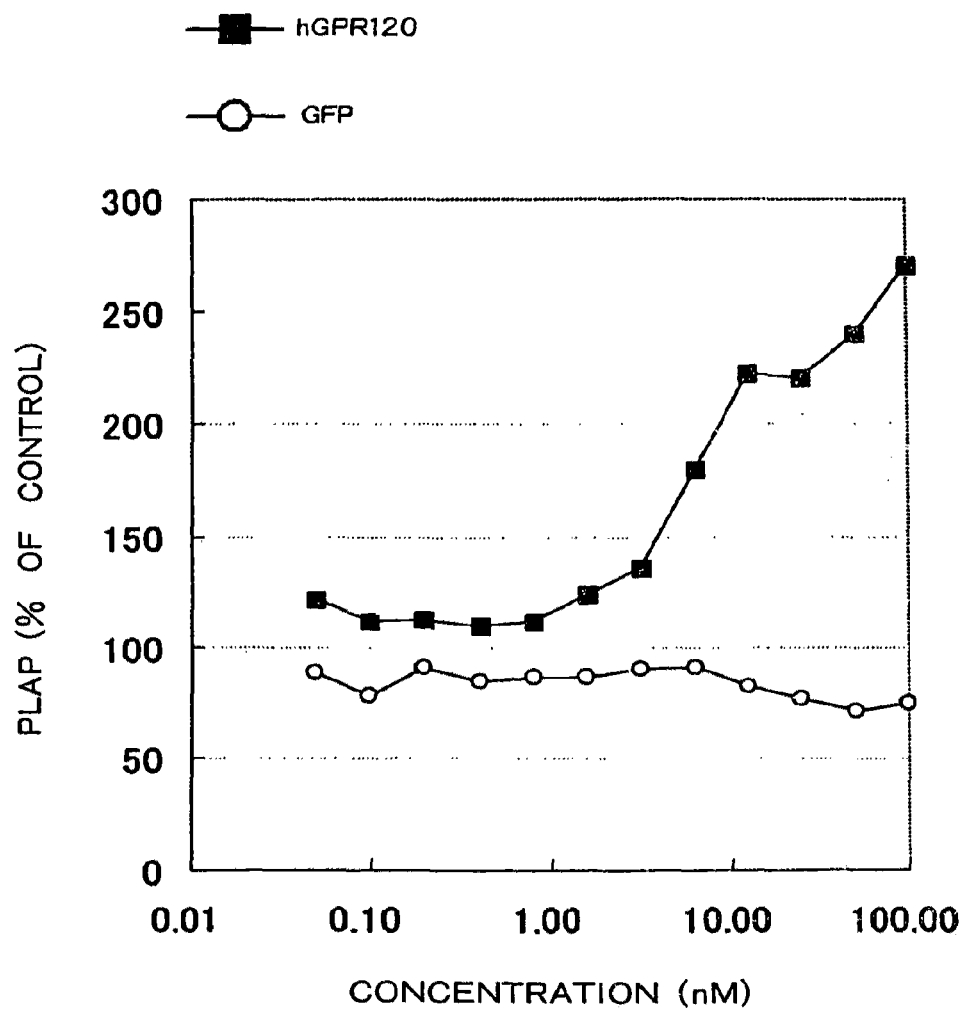
F I G. 13A

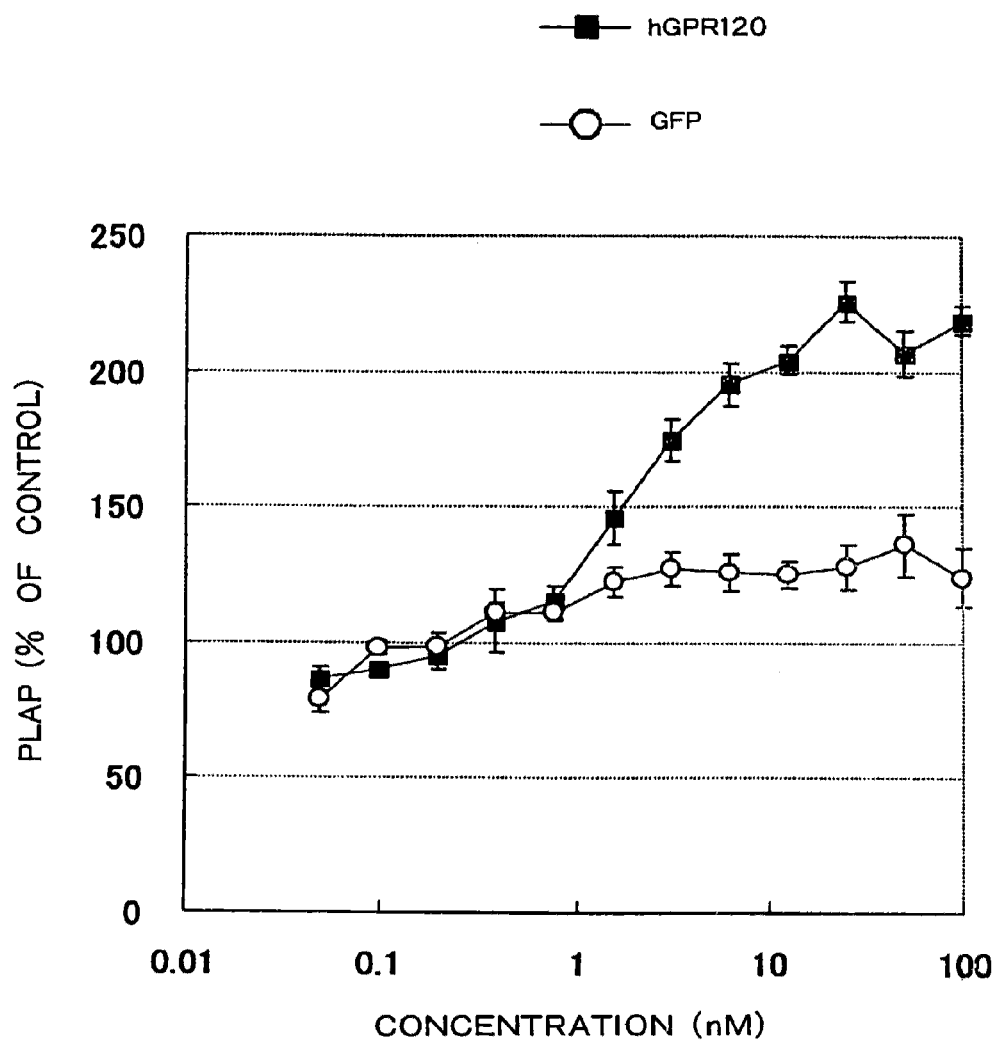
F I G. 14A

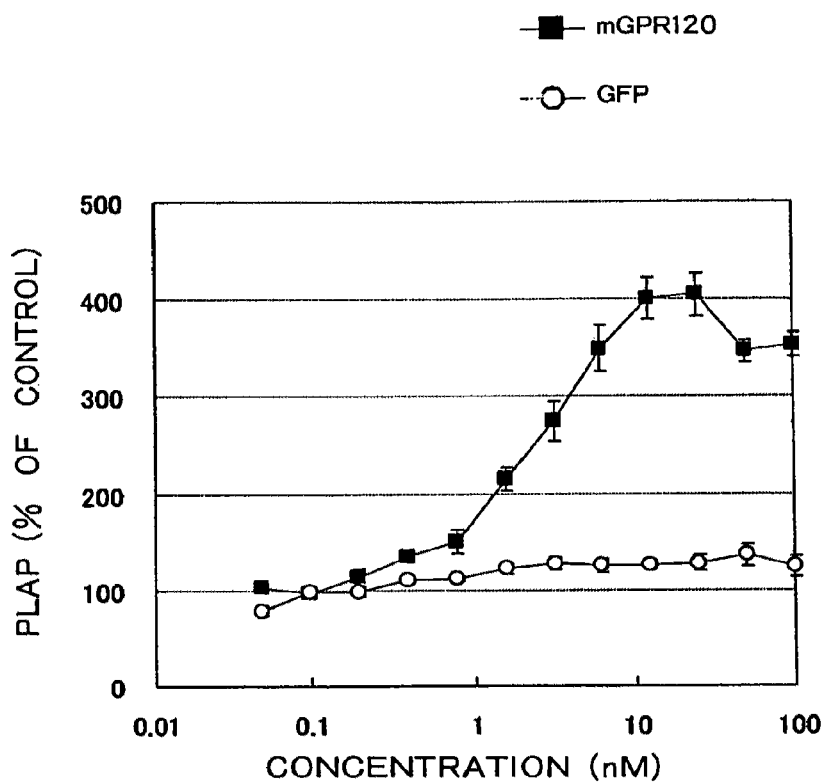
F I G. 14B
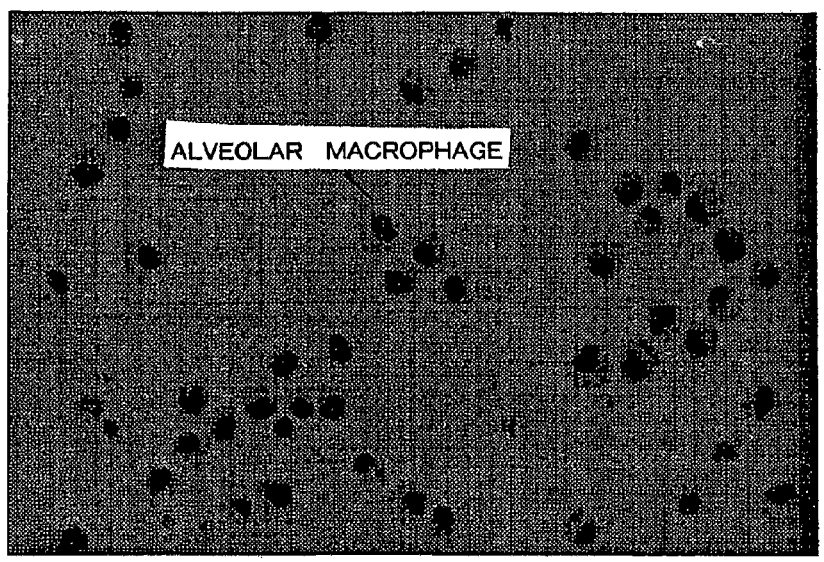
F I G. 15A

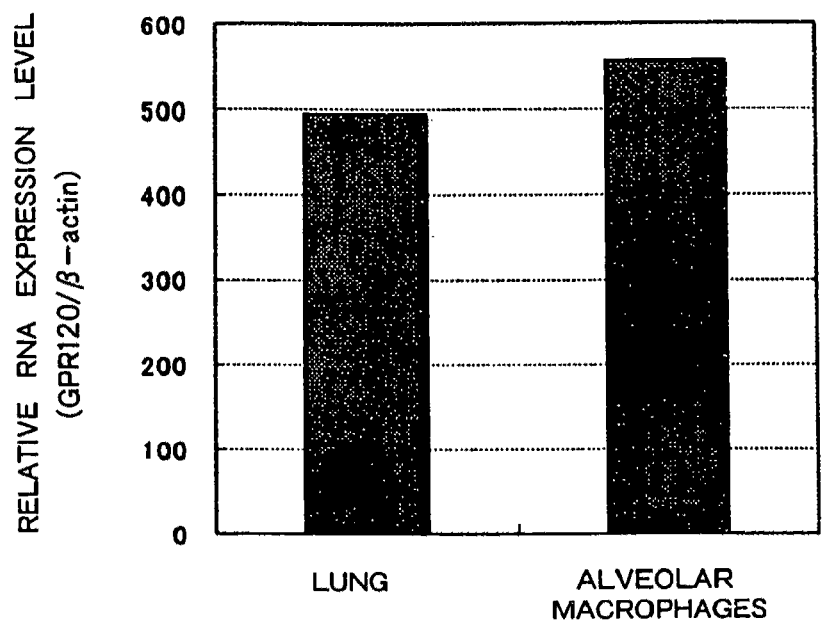
F I G. 15B
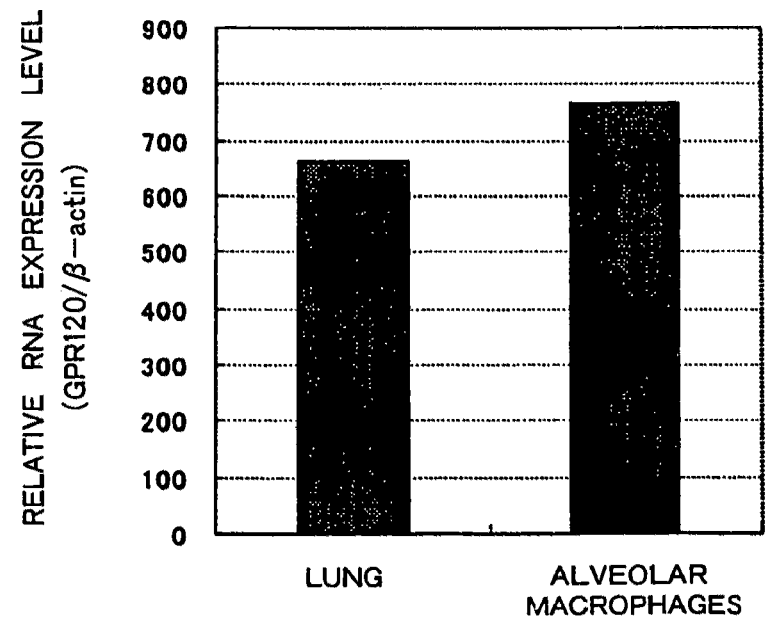
F I G. 15C

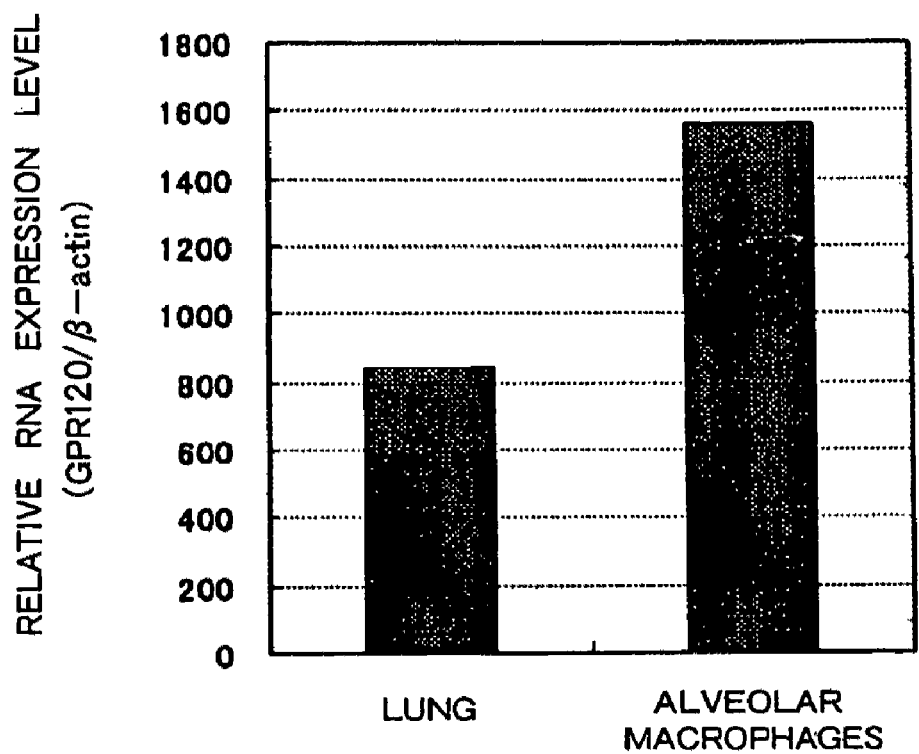
F I G. 15D

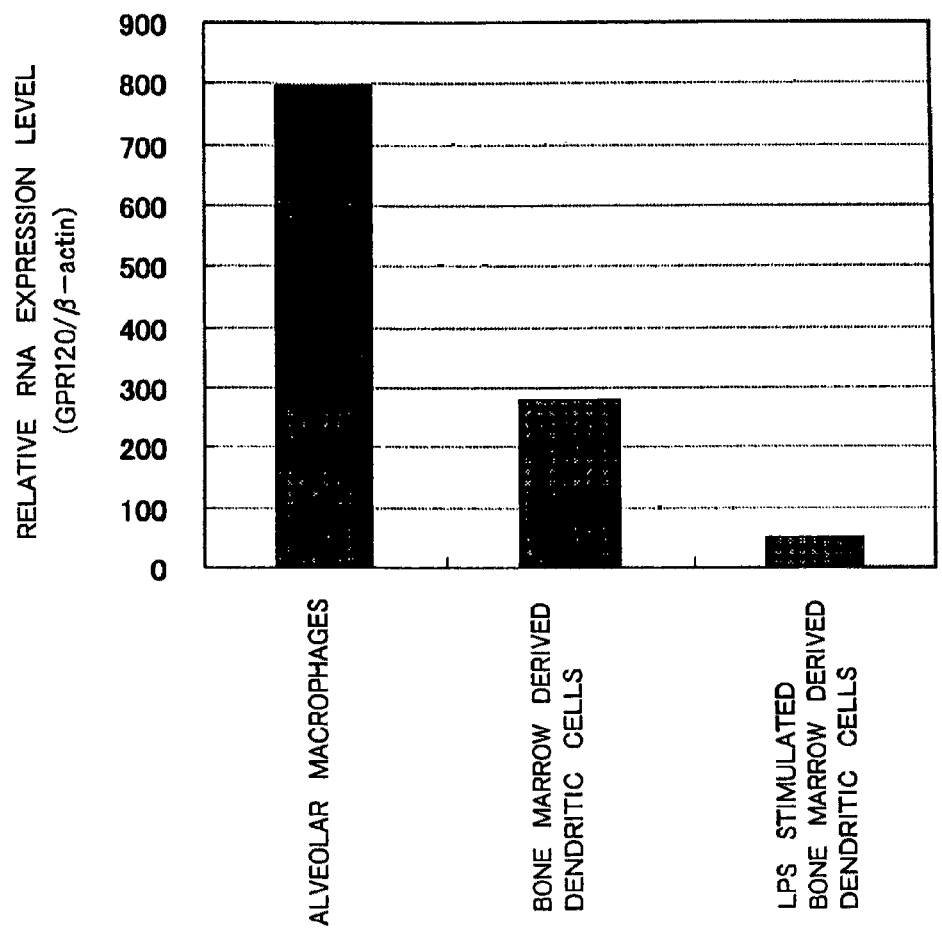
F I G. 20

METHOD FOR SCREENING OF SUBSTANCE WHICH ALTER GPR120-MEDIATED CELL-STIMULATING ACTIVITIES

CROSS-REFERENCE TO RELATED APPLICATIONS

This application is based upon and claims the benefit of priority from the prior Japanese Patent Application No. 2005-254643 filed on Sep. 2, 2005, the entire contents of which are incorporated herein by reference.

BACKGROUND OF THE INVENTION

1. Field of the Invention

This invention relates to a method for screening for a substance which alters the interaction between GPR120, a G protein-coupled receptor protein, and phospholipase or salts thereof (in particular, a substance which alters GPR120 mediated cell stimulating activity), and a screening kit to be used for such screening.

2. Background Art

Many of physiologically active substances such as hormones and neurotransmitters regulate biological functions through their specific receptor proteins expressed on cell surface membranes. Many of these receptor proteins share a 7-transmembrane structure which couples with trimeric G protein (guanine nucleotide-binding protein) which is present intracellularly and accordingly, are called G-protein coupled receptors (GPCR).

GPCR is expressed on the cell surface of a variety of functional cells, organs and organ parts and activates or suppresses cellular functions by transmitting a signal intracellularly via binding to its regulatory molecule. Accordingly, GPCR plays an important role in a variety of organs and organ parts. It is important to clarify interactions between GPCR and these physiologically active substances for better understanding of biological functions, and for the development of drugs which are closely related thereto. The development of these therapeutic drugs requires efficient screening for GPCR agonists and antagonists, a functional analysis of a receptor protein expressed in a living body, and expression systems of the gene in appropriate cells.

In recent years, the presence of a number of novel genes have been revealed by a random analysis of cDNA sequences shown in EST database and the like, or a comprehensive analysis of genome DNA. GPCRs share a 7-transmembrane domain and also a number of other common sequences. Because of this, novel members of GPCR have been found among a number of those newly discovered genes. Ligands for these novel GPCRs thus discovered are usually unidentified. Identification of ligands and functional analysis for orphan GPCRs whose ligands are not yet identified are believed to be significantly important because these may provide an opportunity for the development of new therapeutic drugs.

In most cases, it is difficult to predict a ligand for each of orphan GPCRs. Ligands for GPCRs include a wide variety of substances such as biological amines, amino acids, nucleic acids and its metabolites, peptides, proteins (for example, hormones, and chemokines), and lipids. Purification of a ligand from extracts requires an extraction method specific to each type of ligand substances. Also, in general, a type of signal transduction system activated by orphan GPCR after responding to a ligand is not easily predictable and studies are required in miscellaneous expression systems. Since prediction of a tissue in which a ligand is present is not easy, a number of different tissue extracts are required. Thus, the ligand identification for orphan GPCRs faces a great deal of difficulty. Discovery of a novel ligand for GPCR and its direct application, or screening for a new drug using the novel ligand is expected to provide an opportunity to develop new drugs of which action mechanism is novel and entirely different from that of currently available drugs.

GPR120 has been known to be one of GPCRs (WO00/00611 and, WO00/50596). Ligands for GPCR120 are not completely elucidated, however, fatty acids has been reported as one of ligands (WO2004/065960 and Japanese Patent Application Laid-Open Publication No. 2005-15358).

GPR120 has been known to be involved in the stimulation of cholecystokinin (CCK) secretion from the STC-1 cell line, an intestinal secretory cell line, and therapeutic applications of GPR120 agonists and antagonists are expected to be useful for eating disorders represented by anorexia and, hyperphagia and intestinal disorders associated with those (Japanese Patent Application Laid-Open Publication No. 2005-15358). In addition, it has been reported that GPR120 has stimulatory effects on the secretion of glucagon like peptide-1 (GLP-1) from the STC-1 cell line, an intestinal secretory cell line, and substances interacting with GPR120 are expected to be useful for its therapeutic application for diabetes (Akira Hirasawa et al., Nature Medicine, 11, 90-94, 2004). Moreover, GPR120 is expressed in the pituitary gland and its potential involvement in stress regulation has been also suggested (WO2004/065960).

As described above, fatty acids have been reported as ligands for GPR120. However, it is often difficult to make a ligand solution with fatty acids because fatty acids are barely soluble in water solvent system. Also, fatty acids are easily absorbed to plastics or glass which is used for screening, and unsaturated fatty acids are easily oxidized. Moreover, fatty acids are known to bind to albumin easily. Under physiological conditions, most of fatty acids are bound to blood albumin and only a small part of fatty acids (1%) exist as free fatty acid. For that reason, inhibitory effects of bovine serum albumin (BSA) on GPR120 activity stimulated by fatty acid have been observed in the screening of a GPR120 ligand using fatty acid, and the necessity of screening in the absence of serum or albumin is reported (for example, Akira Hirasawa et al. Nature Medicine, 11, 90-94, 2004). On the other hand, generally, the screening for a drug using cells and proteins is often carried out in the presence of serum or albumin (BSA and the like) since conditions closer to physiological conditions are required. If the screening is carried out in the absence of serum, a long time culture is usually difficult because of cellular damages in the condition where serum is absent. Therefore, it is necessary that cells are cultured in serum containing media in advance and at the time of the screening the media is replaced by the one that contains no serum, which makes the process more complicated.

Accordingly, it has been expected for a new screening system not using fatty acid directly to screen for GPR120 agonists or antagonists.

Phospholipase is a family of enzymes which hydrolyze an ester linkage of glycerophospholipids, and is classified into phospholipase A1, A2, B, C and D depending on the position of the ester linkage to be hydrolyzed. Phospholipase A2 (PLA2) is further classified into secretory (sPLA2), cytoplasmic (cPLA2) and calcium independent (iPLA2) forms. Among them, there are 10 enzymes known for sPLA2.

SUMMARY OF THE INVENTION

The present inventors have now found that, surprisingly, phospholipase, in particular, secretory phospholipase A2

(sPLA2), honey bee venom phospholipase A2 and snake venom phospholipase A2, can activate GPR120 mediated cell stimulating activity. The present invention is based on these findings.

Accordingly, an objective of the present invention is to provide a screening method for a substance which alters the interaction between GPR120 and phospholipase, in more detail, a method for screening substances which alter GPR120 mediated cell stimulating activity, a screening kit to be used for such method, and the like.

According to the present invention, the invention provides a screening method for determining whether a substance of interest is a substance which alters GPR120 mediated cell stimulating activities, comprising using a substance of interest, a biomembrane containing GPR120, or cells containing said biomembrane, and phospholipase or salts thereof. The term "Biomembranes" used herein includes cellular membranes, membranes such as organelles constructing cellular membranes and cells, and lipid bilayer membranes and the like. In addition, reconstructed membranes such as liposome are also included herein. In the present invention, biomembranes containing GPR120, preferably, refer to cellular membranes containing GPR120.

An aspect of the present invention provides a screening method which is characterized by using GPR120, cellular membranes containing GPR120, or cells containing said cellular membranes, and phospholipase and salts thereof, for a substance which alters the interaction between GPR120 and phospholipase and salts thereof. Herein, preferably, substances to be screened are substances which can alter GPR120 mediated cell stimulating activity.

According to a preferred aspect of the present invention, a method of the invention includes the following steps: contacting biomembranes containing GPR120 or cells containing those with phospholipase or salts thereof in the presence or absence of a substance to be screened, and measuring cell stimulating activities to compare between a result measured in the presence of a substance to be screened and a result measured in the absence of the substance.

Furthermore, the present invention provides a screening kit comprising at least GPR120 containing biomembranes or cells containing those, and phospholipase or salts thereof. Also, the invention provides use of GPR120 containing biomembranes or cells containing those, and phospholipase and salts thereof to screen substances which alters GPR120 mediated cell stimulating activity.

According to a screening method of the present invention, the method can screen substances such as CCK and GLP-1 which are involved in the secretion of hormones in gastrointestinal tracts. Accordingly, a method of the invention can screen substances useful for preventive and therapeutic use for diabetes, diabetic complications such as diabetic retinopathy and diabetic nephropathy, hyperlipidemia, arteriosclerosis, angina pectoris, myocardial infarction, pituitary function disorders, mental disorders, immunological diseases, inflammatory diseases, macrophage or dendritic cell related diseases, cancer, eating disorders, represented by anorexia and hyperphagia, and intestinal diseases associated with eating disorders.

BRIEF DESCRIPTION OF DRAWINGS

FIG. 6A shows a UV absorption pattern of rat testis extracts analyzed by HPLC using the Vydac218TP C18 reversed phase column, and GPR120 mediated PLAP activities in each fraction. Active fraction was recovered in peaks shown with arrows.
FIG. 7 shows the result of PLAP activities in GPR120-SE302 cells and control cells using the cultured media of GX-sPLA2-His6-CHO-K1 cells.
FIG. 9A shows the case where hGX-sPLA2-His was used.
FIG. 9B shows the case where mGX-sPLA2-His was used.
FIG. 10B shows the result of PLA2 activities in mGPR120-SE302 cells using commercially-available porcine pancreatic sPLA2 compared to control cells.
FIG. 13A shows the result of PLAP activities in GPR120-SE302 cells using C-terminal FLAG tagged recombinant hGX-sPLA2 compared to control cells.
FIG. 14A shows the result of PLAP activities. GPR120-SE302 cells using C-terminal FLAG tagged recombinant mGX-sPLA2 compared to control cells.
FIG. 14B shows the result of PLAP activities in mGPR120-SE302 cells using C-terminal FLAG tagged recombinant mGX-sPLA2 compared to control cells.
FIG. 15A shows alveolar macrophages stained using Diff-Quick Stain™.
FIG. 15B shows the relative RNA expression level of mGPR120 in lung and alveolar macrophages from C57BL/6 mice.
FIG. 15C shows the relative RNA expression level of mGPR120 in lung and alveolar macrophages from BALB/c mice.
FIG. 15D shows the relative RNA expression level of rat GPR120 in lung and alveolar macrophages from SD rat.

FIG. 20 shows the relative mGPR120 RNA expression in mouse bone marrow derived dendritic cells.

DETAILED DESCRIPTION OF THE INVENTION

Phospholipase

Figure 1:
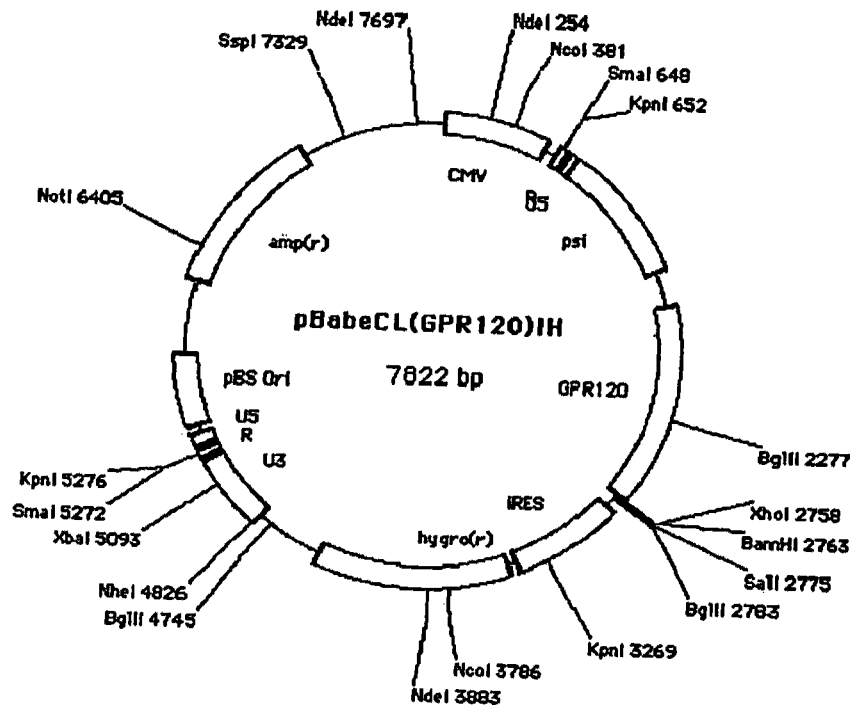
FIG. 1 shows the construction of pBabeCL(GPR120)IH.

The screening method according to the present invention uses phospholipase. Phospholipase includes phospholipase A1, A2, B, C and Z, and phospholipase A1 and phospholipase A2 are preferred for the present invention and phospholipase A2 is more preferred. Phospholipase A2 can be classified into secretory (sPLA2), cytoplasmic (cPLA2) and calcium independent (iPLA2) phospholipase A2 by nature, and a secretory phospholipase is preferred for the present invention. Also, phospholipase A2 derived from honey bee venom or snake venom can be used. According to the present invention, as phospholipase, secretory phospholipase A2 and honey bee venom phospholipase A2 are even more preferred.

Secretory phospholipase A2 (sPLA2) can be classified into 10 groups, IB, IIA, IIC, IID, IIE, IIF, III, V, X, and XIIA, and in the present invention, group IB, IIA, V, and X are preferred, and group IB and X are more preferred, and group X is further preferred.

Phospholipases are well known enzymes and they are easily available for a person skilled in the art. For example, phospholipases can be prepared from organisms comprising a desired type of phospholipase through extraction and purification processes using conventional methods. Moreover, commercially-available phospholipases can be used. Furthermore, signal sequences, prepro-sequences, and sequences of mature form are easily known from the database comprising these sequences and published references. Thus, a polynucleotide capable of expressing a desired phospholipase can be obtained, the cells and the like are prepared by transfecting the cells with the polynucleotide using gene technology methods so as to express the desired phospholipase, and these cells and the like may be used.

Amino acid sequences of phospholipases and encoding DNA sequences have been reported. For example, for secretory phospholipase A2, Swiss Prot accession number: P04054 (human group IB), Q9Z0Y2 (mouse group IB), P04055 (rat group IB), P00592, (pig group IB), P14555 (human group IIA), P31482 (mouse group IIA), P48076 (mouse group IIC), Q9UNK4 (human group IID), Q9NZK7 (human group IIE), Q9BZM2 (human group IIF), Q9NZ20 (human group III), P39877 (human group V), P97391 (mouse group V), O15496 (human group X), Q9QXX3 (mouse group GX), Q9QZT3 (rat group GX), and GenBank accession number: NM_030821 (human group IIA) and the like have been reported. In addition, for honey bee venom phospholipase A2, Swiss Prot accession number: P00630 has been reported. Moreover, for snake venom phospholipase A2, Swiss Prot accession number: SP62022, P00602 and the like have been reported. For phospholipases used in the present invention, the amino acid sequence and the encoding DNA can be specifically identified based on such published information.

Moreover, some of phospholipases become an active form through processing of precursor phospholipase (for example, secretory phospholipase A2 and honey bee venom phospholipase A2). In addition, some of phospholipases become an active form when a prepro-sequence is further removed from a prepro-form in which a signal sequence is removed from a precursor (for example, secretory phospholipases A2 of group IB, secretory phospholipases A2 of group X, and honey bee venom phospholipase A2). Phospholipase used in the present invention can be any of precursor phospholipase, prepro-phospholipase and active forms of phospholipase; however, active forms of phospholipase are preferred. When used in experiments, active forms of phospholipase are optionally referred to simply as phospholipase. For these precursors, prepro-forms and active forms of phospholipase used in the present invention, the amino acid sequence and the DNA encoding thereof can be specifically identified based on the published information.

Specifically, phospholipases of the present invention is composed of polypeptides selected from a group consisting of (A) to (E):

(A) polypeptides comprising any of amino acid sequences previously identified by accession numbers (preferably the amino acid sequence of SEQ ID NO 23, 35, 36, 39, or 41);

(B) polypeptides comprising said amino acid sequences of (A) in which one or several (preferably one or a few) amino acids are substituted, deleted, inserted and/or added, and having substantially the same activity as phospholipase;

(C) polypeptides consisting of said amino acid sequences of (A) having 80% or higher identity to amino acid sequences of (A);

(D) polypeptides encoded by polynucleotide which can hybridize with polynucleotides consisting of base sequences encoding said amino acid sequences of (A) under stringent conditions, and having substantially the same activity as phospholipase; and (E) polypeptides encoded by polynucleotide consisting of base sequences having 80% or higher (preferably 85% or higher, more preferably 90% or higher, even more preferably 95% or higher, even further preferably 98% or higher, particularly preferably 99% or higher) identity to base sequences encoding said amino acid sequences of (A), and having substantially the same activity as phospholipase.

Phospholipases used in the present invention are preferably "polypeptides comprising any of the aforementioned amino acid sequences identified by accession numbers". Said polypeptides include salts thereof, polypeptides with or without a disulfide bond, polypeptides with or without phosphorylation, and furthermore, polypeptides with or without a sugar chain. Phospholipases used in the present invention can be specifically identified by the amino acid sequence or DNA encoding the amino acid sequence based on the published information.

Said "polypeptides with a disulfide bond" refers to polypeptides in which one amino acid at a specific site is crosslinked with another amino acid at another specific site by a —S—S— bond.

Herein, "any of amino acid sequences identified by the aforementioned accession numbers" refers to amino acid sequences identified by the predetermined publicly-known database based on the aforementioned accession numbers which are preferably SEQ ID NO 23, 35, 36, 39 or 41 and more preferably SEQ ID NO 35.

Herein, polypeptides "having substantially the same activity as phospholipase" refers to the polypeptides having activation effects directly or indirectly on GPR120, and GPR120 mediated signal transduction effects, in more detail, having cell stimulating activities on GPR120 expressing cells (for example, detection of changes in translation and transcription of reporter genes due to production of signal transduction substances, release of intracellular $Ca^{2+}$, activation of adenylate cyclase, production of intracellular cAMP, production of intracellular cGMP, release of arachidonic acid, release of acetylcholine, production of inositol phosphate, changes in cell membrane potential, phosphorylation or activation of intracellular proteins, pH changing activity, phosphorylation or activation of MAP kinase, c-fos or c-jun inducing activity, glycerol production activity, lipolytic activity, adrenocorticotrophic hormone (ACTH) secretion activity, chorecystokinin (CCK) secretion activity, glucagon like peptide (GLP-1) secretion activity, and the like). And substantially the same means activities are qualitatively the same. Namely, for having "substantially the same activity as phospholipase", preferably, said activities are equivalent (for example, about 0.01 to 100 fold, preferably 0.05 to 20 fold, more preferably 0.5 to 2 fold) to the activity of phospholipase. These activities can be measured by a conventional method, for example, using the method described in examples below.

In one preferred aspect of the present invention, said polypeptides of (B) (optionally referred to as "modified polypeptides" hereinafter) is a polypeptide comprising any of amino acid sequences identified by the aforementioned accession numbers (preferably SEQ ID NO 23, 35, 36, 39 or 41) in which amino acid sequences have one or several (preferably one or a few) conservative substitutions, and still have substantially the same activity as phospholipase.

"Conservative substitution" in the present specification refers to substitutions of one or several (preferably a few) amino acid residues with another chemically analogous amino acid residue. For example, there may be mentioned a case that a hydrophobic residue is substituted by another hydrophobic residue, or a polar residue is substituted by another polar residue with the same charge. These functionally similar amino acids which are capable of such substitution are well known in the field of the art for each amino acid. Specific examples include alanine, valine, isoleucine, leucine, proline, tryptophan, phenylalanine, methionine and the like, as non-polar (hydrophobic) amino acids. Examples for polar (neutral) amino acids are glycine, serine, threonine, tyrosine, glutamine, asparagine, cysteine, and the like. Examples for positively charged (basic) amino acids are arginine, histidine, lysine and the like. In addition, examples for negatively charged (acidic) amino acids are aspartic acid, glutamic acid and the like.

Herein, the number of amino acids which can be deleted, substituted, inserted and/or added is, for example, 1 to 30, preferably 1 to 20, more preferably 1 to 10, even more preferably 1 to 5, particularly preferably 1 to 2. In addition, said altered polypeptides include salts thereof, polypeptides with or without a disulfide bond, with or without phosphorylation, with or without a sugar chain. Thus, the source of said altered polypeptides is not limited to human so far as polypeptides meet these conditions.

These altered polypeptides may include polypeptides further altered or modified at the N-terminus (amino terminus) and the C-terminus (carboxyl terminus). For example, the C-terminal carboxyl group can be carboxylate (—COO—), amide (—CONH$_2$) or ester (—COOR). In addition, herein said R may be, for example, a linear, branched or circular C1-6 alkyl group, C6-12 aryl group, or the like. Moreover, altered polypeptides include polypeptides with an N-terminal amino group protected by a common protective group.

Examples of said polypeptides of (B) are phospholipases or variants thereof derived from organisms other than human [for example, non-human mammals (for example, mouse, rat, hamster, pig, dog and the like), birds, reptiles, amphibians, fishes, insects and the like]. Specific examples include polypeptides composed of the amino acid sequence of SEQ ID NO 23, 36, 39, or 41 (derived from rat, mouse, pig, and bee (Western honey bee)).

Said polypeptides of (C) (optionally referred to as "homologous polypeptides" hereinafter) are not limited so far as polypeptides have 80% or higher identity with respect to the amino acid sequence of phospholipases, but preferably 85% or higher, more preferably 90% or higher, even more preferably 95% or higher, further more preferably 98% or higher, particularly preferably 99% or higher homology to the amino acid sequence of phospholipase, and have substantially the same activity as phospholipase.

Any of values for "identity" used in the present specification can be values calculated using a homology search program well known to a person skilled in the art, and for example, values can be calculated by the homology algorithm BLAST (Basic local alignment search tool) http://www.ncbi.nlm.nih.gov/BLAST/ provided by National Center for Biotechnology Information (NCBI) using default (initially set) parameters. In addition, said homologous polypeptides include salts thereof, polypeptides with or without a disulfide bond, with or without phosphorylation, and, furthermore, polypeptides with or without a sugar chain. Thus, the source of said homologous polypeptides is not limited to human so far as polypeptides meet these conditions. For example, said homologous polypeptides include phospholipases and variants thereof derived from organisms other than human [for example, mammals other than human (for example, mouse, rat, hamster, pig, dog and the like), birds, reptiles, amphibians, fishes, insects and the like].

Specifically, said homologous polypeptides of (C) are, for example, polypeptides composed of amino acid sequence of SEQ ID NO 23, 36, 39, or 41 (derived from rat, mouse, pig and bee).

In addition, in this specification, the term "variant" refers to "variation", namely individual variations of the same polypeptide within the same species, or variations of homologous polypeptides between several species.

Moreover, partial polypeptides of phospholipase of the present invention, (namely, phospholipases, altered polypeptides thereof and homologous polypeptides thereof) also can be used so far as the polypeptide has substantially the same activity as phospholipase. In this case, the number of amino acids composing partial polypeptides is 90%, 80%, 70%, 60%, 50%, 40%, 30%, 20%, 10% or 5% of the number of amino acids of phospholipase.

Method for Preparing Phospholipase

These phospholipases (namely, phospholipases, altered polypeptides thereof, and homologous polypeptides thereof) and their partial polypeptides of the present invention can be prepared by various publicly known methods, such as gene engineering methods, and synthetic methods. Specifically, if gene engineering methods are applied, desired polypeptides can be prepared by inserting the polynucleotide encoding phospholipase or its partial peptide into appropriate host cells, culturing transformants under conditions which enable expression of the gene, and carrying out isolation and purification of the desired polypeptides from cultured materials using conventional methods for isolation and purification of expressed proteins. As the aforementioned methods for isolation and purification there can be mentioned salting out with ammonium sulfate, ion-exchange chromatography using ion-exchange cellulose, molecular sieve chromatography using molecular sieve gels, affinity chromatography using protein A-bound polysaccharides, dialysis, freeze-drying and the like. In addition, in case synthetic methods are applied, conventional methods of synthesis such as a liquid phase method or a solid phase method can be used, and usually an automatic synthesizer can be used. Synthesis of chemically modified compounds can be carried out using conventional methods. Moreover, a desired partial polypeptide can be prepared by enzymatic cleavage using appropriate proteases.

Among methods for preparation of phospholipase used in the present invention, gene engineering methods are described in detail in the following, these methods can be also applied for partial polypeptides thereof with no particular limitation so far as partial polypeptides can be used for the screening which will be described later.

Polynucleotides Encoding Phospholipase

Polynucleotides encoding phospholipase used in the present invention (namely, phospholipases, altered polypeptides thereof, and homologous polypeptides thereof) are not specifically limited so far as the polynucleotides encode said phospholipases, said altered polypeptides, or said homologous polypeptides.

In addition, the term "polynucleotide" used in the present specification refers to both DNA and RNA. Polynucleotides encoding phospholipase used in the present invention are specifically selected from the group consisting of (I)-(VI) listed below:

(I) polynucleotides composed of any of base sequences identified by the aforementioned accession numbers (preferably the base sequence of SEQ ID NO 25, 28, 37, 38 or 40);

(II) polynucleotides encoding "polypeptides composed of any of amino acid sequences identified by the aforementioned accession numbers (preferably the amino acid sequence of SEQ ID NO 23, 35, 36, 39, or 41)";

(III) polynucleotides encoding "polypeptides comprising any of amino acid sequences identified by the aforementioned accession numbers (preferably the amino acid sequence of SEQ ID NO 23, 35, 36, 39, or 41) and having substantially the same activity as phospholipase";

(IV) polynucleotides encoding "polypeptides comprising any of amino acid sequences identified by the aforementioned accession numbers (preferably the amino acid sequence of SEQ ID NO 23, 35, 36, 39, or 41) in which one or several (preferably one or a few) amino acids are deleted, substituted, inserted and/or added at one or several sites (preferably one or a few), and yet having substantially the same activity as phospholipase";

(V) polynucleotides which can hybridize with the polynucleotide composed of any of base sequences identified by the aforementioned accession numbers (preferably, the base sequence of SEQ ID NO 25, 28, 37, 38, or 40) under stringent conditions, and encode polypeptides having substantially the same activity as phospholipase; and (VI) polynucleotides having 80% or higher, preferably 85% or higher, more preferably 90% or higher, even more preferably 95% or higher, even further preferably 98% or higher and particularly preferably 99% or higher identity to any of the base sequences identified by the aforementioned accession numbers (preferably the base sequence of SEQ ID NO 25, 28, 37, 38, or 40) and encode polypeptides having substantially the same activity as said phospholipase.

Herein, "any of base sequences identified by the aforementioned accession numbers" refers to the base sequences which are identified by the predetermined publicly-known database based on the aforementioned accession numbers (or the base sequence encoding the amino acid sequence thereby specified), preferably base sequences of SEQ ID NO 25, 28, 37, 38 or 40, and more preferably 25.

In an aspect of the present invention, polynucleotides encoding phospholipase used in the present invention are polynucleotides encoding "polypeptides comprising any of amino acid sequences identified by the aforementioned accession numbers (preferably SEQ ID NO 23, 35, 36, 39, or 41) in which one or several (preferably one or a few) amino acids are deleted, substituted, inserted and/or added at one or several sites (preferably one or a few), and yet having substantially the same activity as said phospholipase". Herein, the number of amino acids which may be deleted, substituted, inserted and/or added is, for example, 1 to 30, preferably 1 to 20, more preferably 1 to 10, even more preferably 1 to 5, and particularly preferably 1 to 2.

Variants obtained by adding, deleting and/or substituting amino acids can be, for example, prepared by conducting site-specific mutagenesis of the DNA encoding the polypeptides using a publicly known method (for example, see Nucleic Acid Research, Vol. 10, No. 20, p. 6487-6500, 1982). The term "one or several amino acids" used in this specification refers to a certain number of amino acids which can be added, deleted, inserted and/or substituted by site-specific mutagenesis.

Site-specific mutagenesis, for example, other than a particular inconsistency which is a desired mutation, can be carried out using synthetic oligonucleotide primers complementary to a single stranded phage DNA to be mutated. Namely, complementary DNA chains are synthesized by phage using said synthetic oligonucleotide as a primer, and host cells are transformed by introducing the obtained double stranded DNA. Cultured materials of transformed bacteria are plated on agar plates to make a plaque from a single cell containing the phage. By doing so, theoretically, 50% of new colonies contain the phage having mutated single strand and the remaining 50% contains the original sequence. Plaques obtained are hybridized with synthetic probes labeled by kinase treatment under the temperature that the probe can hybridize with DNA having, a desired mutation but can not hybridize with the original chain. Then, plaques hybridized with said probe are picked up and cultured to recover DNA.

Moreover, in addition to the above-mentioned site-specific mutagenesis, there are other methods to substitute, delete, insert, and/or add one or several amino acids on amino acid sequences of bioactive peptides of phospholipase without loosing activity thereof, such as a method to treat genes with mutagen and a method to cleave/open genes selectively and delete, add, insert and/or substitute selected nucleotides, and then make the linkage.

In this specification, "deletion" includes deletion of terminal amino acid residues of the amino acid sequence, and deletion of amino acid residues in the middle of the amino acid sequence.

The term "addition" includes addition of amino acid residues at a terminus of the amino acid sequence and deletion of amino acid residues in the middle of the amino acid residues.

There are several codons encoding one amino acid. Therefore, any DNA encoding any of amino acid sequences identified by the aforementioned accession numbers (preferably the amino acid sequence of SEQ ID NO 23, 35, 36, 39 or 41), or any DNA encoding the domain having enzyme activity thereof are included within the range of the present invention.

In another aspect of the present invention, polynucleotides encoding phospholipases used in the invention can hybridize with polynucleotides composed of any of the base sequences identified by the aforementioned accession numbers (preferably the base sequence of SEQ ID NO 25, 28, 37, 38 or 40)

under stringent conditions and encode polypeptides having substantially the same activity as said phospholipase. Specifically, it refers to polynucleotides composed of the base sequences of SEQ ID NO 25, 28, 37, 38, or 40 (derived from mouse, rat, pig, and bee).

In this specification, polynucleotides which can hybridize under stringent conditions refers to specifically, for example, polynucleotides having at least 70% or higher, preferably 80% or higher, more preferably 85% or higher, even more preferably 90% or higher and even further preferably 95% or higher and particularly preferably 98% or higher and most preferably 99% or higher identity to the base sequences of SEQ ID NO 25, 28, 37, 38, or 40 when calculated by homology search software such as FASTA, BLAST, Smith-Waterman [Meth. Enzym., 164, 765 (1988)] using default (initially set) parameters. Moreover, as "stringent hybridization conditions", there can be mentioned, for example, "2×SSC, 0.1% SDS, 50° C.", "2×SSC, 0.1% SDS, 42° C.", and "1×SSC, 0.1% SDS, 37° C." and as more stringent conditions, there can be mentioned, for example, "2×SSC, 0.1% SDS, 65° C.", "0.5×SSC, 0.1% SDS, 42° C.", and "0.2×SSC, 0.1% SDS, 65° C.". In more particularly, as a method using Rapid-hyb buffer (Amersham Life Science), it can be considered to carry out pre-hybridizing at 68° C. for 30 min or more, then adding probes and hybridizing at 68° C. for one hour or more followed by washing three times in 2×SSC and 0.1% SDS at room temperature for 20 min, three times in 1×SSC, 0.1% SDS at 37° C. for 20 min, and finally twice in 1×SSC, 0.1% SDS at 50° C. for 20 min. Alternatively, for example, pre-hybridization can be carried out in Expresshyb Hybridization Solution (CLONTECH) at 55° C. for 30 min or more, then adding labeled probes and incubating at 37-55° C. for 1 hour or more and washing three times in 1×SSC, 0.1% SDS, at room temperature for 20 min, once in 1×SSC, 0.1% SDS, at 37° C. for 20 min. Herein, conditions can be made more stringent by raising temperature for pre-hybridization, hybridization and the second washing. For example, temperature for pre-hybridization or hybridization can be 60° C., or 68° C. for even more stringent conditions. A person skilled in the art can set a condition to obtain isoforms and allelic variants of phospholipase, and corresponding genes derived from other species by taking into account other conditions such as probe concentration, probe length, and incubation time in addition to the condition such as salt concentration of buffer and temperature.

Detailed procedures of a hybridization method can be found in "Molecular Cloning, A Laboratory Manual 2nd ed." (Cold Spring Harbor Press (1989); in particular, Section 9.47-9.58), "Current Protocols in Molecular Biology" (John Wiley & Sons (1987-1997); in particular, Section 6.3-6.4, and "DNA Cloning 1: Core Techniques, A Practical Approach 2nd Ed." (Oxford University (1995); in particular, Section 2.10 for experimental conditions). As polynucleotides to be hybridized, there can be mentioned polynucleotides comprising the base sequences having at least 50% or higher, preferably 70% or higher, more preferably 80% or higher, even more preferably 90% or higher (for example, 95% or higher, or even 99% or higher) identity to the base sequences comprising the base of SEQ ID NO 25, 28, 37, 38 or 40. The degree of identity can be determined by BLAST algorithm (Altschul (1990) Proc. Natl. Acad. Sci. USA 87: 2264-8; Karlin and Altschul (1993) Proc. Natl. Acad. Sci. USA 90: 5873-7) in the same way as determination of homology as described above. Other than the above-mentioned BLASTN program for base sequence, other programs to determine identity of amino acid sequence based on this algorithm, such as BLASTIX (Altschul et al. (1990) J. Mol. Biol. 215: 403-10), have been developed and available. Specific methods for analysis can be found at the aforementioned website http://www.ncbi.nlm.nih.gov., and the like.

In addition, by polymerase chain reaction (PCR) (Current Protocols in Molecular Biology, John Wiley & Sons (1987) Section 6.1-6.4), isoforms and allelic variants of phospholipase and the like can be obtained from cDNA libraries and genome libraries of mammals, such as human, mouse, rat, rabbit, hamster, chicken, pig, cattle, goat, sheep and the like, using primers designed based on the base sequences of SEQ ID NO 25, 28, 37, 38, or 40.

The base sequence of polynucleotides can be confirmed by determining the sequence using a conventional method. For example, confirmation can be made using a method such as the dideoxynucleotide chain termination method (Sanger et al. (1977) Proc. Natl. Acad. Sci. USA 74: 5463). Moreover, the sequence can be also analyzed using an appropriate DNA sequencer.

Polynucleotides encoding phospholipases of the present invention can be, for example, nature-derived or completely synthetic. Furthermore, polynucleotides can be synthesized from a part of nature-derived nucleotides. As typical methods to acquire polynucleotides encoding phospholipase used in the present invention, there can be mentioned, for example, a method to screen from commercially-available DNA libraries or cDNA libraries using an appropriate DNA probe prepared based on the information of the sequence of partial polynucleotides (for example, base sequences encoding amino acid sequences of SEQ ID NOS 21 and 24).

Polynucleotides encoding phospholipases used in the present invention are preferably "polynucleotides composed of any of the base sequences identified by the aforementioned accession numbers (for example, the base sequence of SEQ ID NO 25). The base sequence of SEQ ID NO 25 has an open reading frame which starts with ATG at nucleotide number 441-443 and ends with TAA at nucleotide number 936-938. In addition, polynucleotides composed of the base sequences of SEQ ID NO 25, 28, 37, 38 or 40 can be mentioned.

Plasmids

As a method to incorporate the DNA fragments of the present invention into plasmids, there can be mentioned, for example, a method described by Sambrook, et al. in Molecular Cloning, A Laboratory Manual, second edition, Cold Spring Harbor Laboratory, 1.53 (1989) or the like. Conveniently, commercially-available ligation kits (for example, products by Takara Shuzo Co., Ltd. and the like) can be also used. Recombinant plasmids prepared by these methods are introduced into host cells (for example, *E. coli* YBI, LE392 or XL-1Bluc and the like). Plasmids used for transformation are not specifically limited to any particular plasmid so far as the above-mentioned polynucleotides encoding the aforementioned phospholipases are contained, and plasmids prepared by inserting those polynucleotides into publicly known vectors selected appropriately according to host cells to be used can be mentioned. For example, phospholipase alone, or fusion protein of phospholipase and protein tag (for example, histidine tag, FLAG tag, glutathione-S-transferase (GST), maltose binding protein (MBP)) can be incorporated into expression vectors.

Vectors can be conveniently prepared by conventional method by linking a desired gene into vectors for recombination (plasmid DNA) available in the art. Examples of Vectors used herein are specifically but not limited to *Escherichia coli* derived plasmids such as pBluescript, pUC18, pUC19, and pBR322.

Expression vectors are particularly useful for the production of desired proteins. Expression vectors which can express a desired gene and produce a desired protein in variety of host cells including prokaryotic cells and/or eukaryotic cells can be employed without any restriction. However, for example, expression vectors for *Escherichia coli* include, preferably, pQE-30, pQE-60, pMAL-C2, pMAL-p2, and pSE420, and expression vectors for yeast include, preferably, pYES2 (the genus of *Saccharomyces*), pPIC3, 5K, pPIC9K, pAO815 (these four are the genus of *Pichia*), pBacPAK8/9, pBK283, pVL1392, pBlueBac4.5, and the like.

Transformants

Transformants can be prepared by introducing the desired expression vector into host cells. Host cells used herein are not specifically limited so far as cells are appropriate for expression vectors of the present invention and able to be transformed, and a variety of cells conventionally used in the field of the art of the present invention including natural cells or artificially established recombinant cells. For example, bacterial cells (the genus of *Escherichia* and *Bacillus*), yeast cells (the genus of *Saccharomyces, Pichia*, and the like), animal cells, insect cells, and plant cells can be mentioned.

In particular, *Escherichia coli* bacteria, yeast cells or insect cells are preferred. Specifically, *Escherichia coli* bacteria (M15, JM109 and the like), yeast cells (INVSc1 (the genus of *Saccharomyces*), GS115, KM71 (these two are the genus of *Pichia*), and the like), insect cells (BmN4, silkworm larva and the like) are illustrated. In addition, as animal cells, cells derived from mouse, rat, hamster, monkey or human or cultured cell lines thereof are illustrated. Furthermore, plant cells are not specifically limited so far as they can be cultured, and for example, cells derived from tobacco, plants of the genus of *Arabidopsis*, rice, corn and wheat are illustrated.

For vectors of the present invention, a methionine codon (ATG) is illustrated as a suitable initiation codon and a common termination codon (for example, TAG, TGA and the like) is illustrated as a termination codon.

Expression vectors can be prepared by linking at least a promoter, an initiation codon, a desired gene, a termination codon and a terminator domain continuously and circularly to an appropriate unit capable of replication. Herein, if desired, appropriate DNA fragments (for example, linker or other restriction sites and the like.) can be employed by conventional methods such as digestion by restriction enzyme or ligation using T4DNA ligase.

Introduction of expression vectors used in the present invention into host cells [transformation (transduction)] can be achieved using publicly known conventional methods. For example, bacterial cells (*E. coli, Bacillus subtilis*, or the like) can be transformed using the method by Cohen et al. [Proc. Natl. Acad. Sci. USA, 69, 2110 (1972)], the protoplast method [Mol. Gen. Genet., 168, 111 (1979)] or the competent method [J. Mol. Biol., 56, 209 (1971)]. *Saccharomyces cerevisiae* can be transformed, for example, using the method by Hinnen et al. [Proc. Natl. Acad. Sci. USA, 75, 1927 (1978)] or the lithium method [3. Bacteriol., 153, 163 (1983)]. Animal cells can be transformed, for example, using the method by Graham [Virology, 52, 456 (1973)], and insect cells can be transformed, using, for example, the method by Summers et al. [Mol. Cell. Biol., 3, 2156-2165, (1983)], respectively. Plant cells can be transformed by the method using *Agrobacterium* bacteria (Horsch et al., Science, 227, 129 (1985), Hiei et al., Plant J., 6, 271-282 (1994)), the electroporation method (Fromm et al., Nature, 319, 791 (1986)), the PEG method (Paszkowski et al., EMBO J., 3, 2717 (1984)), the microinjection method (Crossway et al., Mol. Gen. Genet., 202, 179 (1986)), or the particle acceleration method (McCabe et al., Bio/Technology, 6, 923 (1988)).

In the present invention, phospholipase can be expressed (produced), for example, by culturing the transformed cells comprising expression vectors prepared as described above in the nutrient media. Preferably, the nutrient medium contains carbon sources and inorganic nitrogen sources or organic nitrogen sources required for the growth of host cells (transformants). Examples of carbon sources are glucose, dextran, soluble starch, sucrose, and methanol. Examples of inorganic or organic nitrogen sources are ammonium salts, nitrates, amino acids, corn steep liquor, peptone, casein, meat extracts, soybean waste, and potato extracts. In addition, if desired, the medium may contain other nutrients (for example, inorganic salts (for example, sodium chloride, calcium chloride, sodium dihydrogenphosphate, and magnesium chloride), vitamins, antibiotics (for example, tetracycline, neomycin, ampicillin, kanamycin and the like). Cultures are carried out using a well known method to the field of the art. Culture conditions such as temperature, medium pH and culture time are appropriately selected to enable cells to produce a large amount of proteins of the present invention.

Specific culture media and culture conditions used for host cells are illustrated below, but not limited to those illustrated. If bacteria, Actinomyces, yeasts, or filamentous bacteria are used as host cells, for example, liquid media comprising the aforementioned nutrient sources are suitable. Preferably, examples of media with pH 5-8 are LB medium, M9 medium (Miller et al., Exp. Mol. Genet., Cold Spring Harbor Laboratory, p. 431, 1972), and the like. Using these media, cell cultures can be carried out usually at 14-43° C., for about 3-24 hours under aeration and stirring if necessary. If bacteria of genus *Bacillus* are used as host cells, cells are usually cultured at 30-40° C. for about 16-96 hours under aeration and stirring if necessary.

If yeast cells are used as host cells, culture media such as Burkholder minimum medium (Bostian, Proc. Natl. Acad. Sci. USA., Vol. 77, p. 4505, 1980) can be used preferably at pH 5-8. Cell cultures are usually carried out at about 20-35° C. for about 14-144 hours, and aeration or stirring can be applied as needed. If animal cells are used as host cells, for example, MEM medium (Science, Vol. 122, p. 501, 1952), DMEM medium (Virology, Vol. 8, p. 396, 1959), PRMI1640 medium (J. Am. Med. Assoc., Vol. 199, p. 519, 1967), and 199 medium (Proc. Soc. Exp. Biol. Med., Vol. 73, p. 1, 1959) and the like comprising about 5-20% of fetal bovine serum can be used. Medium pH of about 6-8 is preferred. Cultures are usually carried out at 30-40° C. for about 15-72 hours, and also aeration and stirring can be applied as needed.

If insect cells are used as host cells, for example, Grace's medium (Proc. Natl. Acad. Sci. USA., Vol. 82, p. 8404, 1985) comprising fetal bovine serum can be mentioned and the medium pH of about 5-8 is preferred. Cultures are usually carried out at 20-40° C. for about 15-100 hours, and also aeration and stirring can be applied as needed.

Methods for expression and purification of phospholipase are found in a number of publicly known literatures (for example, Kohji Hanasaki, et al., The Journal of Biological Chemistry 274 (48), 34203-34211, 1999, and the like).

Methods for purification of a desired polypeptide from cultured materials of transformants (expressing cells or culture supernatants) are, for example, salting out with ammonium sulfate, ion-exchange chromatography using a ion-exchange cellulose, molecular sieve chromatography using molecular sieve gel, affinity chromatography using protein A-linked polysaccharides, dialysis, freeze drying, or the like. In addition, for synthetic methods, conventional methods such as liquid phase synthesis or solid phase synthesis can be applied, and usually an automatic synthesizer can be used.

Synthesis of chemical modifiers can be carried out using conventional methods. Moreover, a desired partial polypeptide can be prepared by enzymatic cleavage using appropriate proteases.

Phospholipases used in the present invention may be salts thereof. Herein, "salts" refers to pharmaceutically acceptable salts which are not specifically limited so far as they form pharmaceutically acceptable salts with phospholipase. Specific examples include hydrohalide salts (for example, hydrofluoride, hydrochloride, hydrobromide, hydroiodide and the like), inorganic acid salts (for example, sulfates, nitrates, perchlorates, phosphates, carbonates, bicarbonates and the like), organic carbonates (for example, acetates, oxalates, maleates, tartrates, fumarates, citrates and the like), organic sulfonates (for example, methanesulfonates, trifluoromethanesulfonates, ethanesulfonates, benzenesulfonates, toluenesulfonates, camphorsulfonates and the like), amino acid salts (for example, aspartates, glutamates and the like), quaternary amines, alkaline metal salts (for example, sodium salts, potassium salts and the like), and alkaline earth metal salts (for example, magnesium salts, calcium salts and the like).

Phospholipases used in the present invention have a stimulatory activity of GPR120, and fragments of phospholipase can be used so far as the fragments have substantially the same activity as phospholipase.

Herein, the aforementioned fragments "have substantially the same activity as phospholipase" means that the fragment has a signal transduction activity mediated by GPR120, in more detail, the fragment has a cell stimulating activity on cells expressing GPR120 (for example, detection of changes in translation and transcription of reporter genes due to production of signal transduction substances, release of intracellular $Ca^{2+}$, activation of adenylate cyclase, production of intracellular cAMP, production of intracellular cGMP, release of arachidonic acid, release of acetylcholine, production of inositol phosphate, changes in cell membrane potential, phosphorylation or activation of intracellular proteins, pH changing activity, phosphorylation or activation of MAP kinase, c-fos or c-jun inducing activity, glycerol production activity, lipolytic activity, activation of adrenocorticotrophic hormone (ACTH) secretion, activation of chorecystokinin (CCK) secretion, activation of glucagon like peptide (GLP-1) secretion and the like). And substantially the same means activities are qualitatively the same, namely, in order to have "substantially the same activity as phospholipase", said activities are preferably equivalent (for example, about 0.01-100 fold, preferably 0.05-20 fold, more preferably 0.5-2 fold). These activities can be measured by a conventional method, for example, using the method described in examples below.

GPR120

GPR120 used in the present invention is not particularly limited in source thereof so far as it has an activation effect in response to phospholipase (for example, sPLA2) and a cell stimulating activity of cells expressing GPR120 (for example, detection of changes in translation and transcription of reporter genes due to production of signal transduction substances, release of intracellular $Ca^{2+}$, activation of adenylate cyclase, production of intracellular cAMP, production of intracellular cGMP, release of arachidonic acid, release of acetylcholine, production of inositol phosphate, changes in cell membrane potential, phosphorylation or activation of intracellular proteins, pH changing activity, phosphorylation or activation of MAP kinase, c-fos or c-jun inducing activity, glycerol production activity, lipolytic activity, activation of adrenocorticotrophic hormone (ACTH) secretion, activation of chorecystokinin (CCK) secretion, activation of glucagon like peptide (GLP-1) secretion and the like), for example, it includes GPR120 derived from natural sources such as GPR120 expressing organs, tissues and cells, and artificially prepared GPR120 using well known gene engineering methods or synthetic methods. In addition, a partial polypeptide of GPR120 is not specifically limited so far as it can be used for screening as described below, for example, a partial polypeptide which has a cell stimulating activity of phospholipase and a polypeptide comprising the amino acid sequence corresponding to the extracellular domain can be used.

Specifically, GPR120 used for screening of the present invention is a kind of G-protein coupled receptor protein and is a polypeptide of which amino acid sequence (derived from human, mouse and rat) and the DNA sequence encoding thereof have been reported [for example, GenBank accession number NP_859529 (human), NP_861413 (mouse), XP_215281 (rat), GPR120 is also called 14273]. Specifically, GPR120 is a polypeptide selected from the group consisting of:

(a) polypeptides comprising the amino acid sequence of SEQ ID NO 2;

(b) polypeptides comprising the amino acid sequence of SEQ ID NO 2, in which one or several (preferably one or a few) amino acids are substituted, deleted, inserted and/or added, and having substantially the same activity as GPR120;

(c) polypeptides consisting of the amino acid sequence having 80% or higher identity to the amino acid sequence of SEQ ID NO 2;

(d) polypeptides encoded by polynucleotides which can hybridize with polynucleotides consisting of the base sequence of SEQ ID NO 1 under stringent conditions and have substantially the same activity as GPR120;

(e) polypeptides encoded by polynucleotides consisting of the base sequences having 80% or higher (preferably 85% or higher, more preferably 90% or higher, even more preferably 95% or higher, even further preferably 98% or higher, particularly preferably 99% or higher) identity to the base sequence of SEQ ID NO 1, and have substantially the same activity as GPR120.

For GPR120 used in the present invention, "polypeptides composed of the amino acid sequence of SEQ ID NO 2" are preferred. In addition, said polypeptides include salts thereof, polypeptides with or without a disulfide bond, with or without phosphorylation, and furthermore with or without a sugar chain.

Herein, polypeptides "having substantially the same activity as GPR120" refers to the polypeptides having an activation effect in response to phospholipase (for example, sPLA2) and having a GPR120 mediated signal transduction activity, in more detail, having an activation effect of GPR120 expressing cells (for example, detection of changes in translation and transcription of reporter genes due to production of signal transduction substances, release of intracellular $Ca^{2+}$, activation of adenylate cyclase, production of intracellular cAMP, production of intracellular cGMP, release of arachidonic acid, release of acetylcholine, production of inositol phosphate, changes in cell membrane potential, phosphorylation or activation of intracellular proteins, pH changing activity, phosphorylation or activation of MAP kinase, c-fos or c-jun inducing activity, glycerol production activity, lipolytic activity, activation of adrenocorticotrophic hormone (ACTH) secretion, activation of chorecystokinin (CCK) secretion, activation of glucagon like peptide (GLP-1) secretion and the like). In addition, "substantially the same" means its activity is qualitatively equivalent. Namely, in order to "have substantially the same activity as GPR120", said activity is preferably equivalent (for example, about 0.01-100 fold, preferably 0.05-20 fold, more preferably 0.5-2 fold) to the activity of GPR120. These activities can be measured using conventional methods, for example, using the methods described in examples below.

In a preferred aspect of the present invention, said polypeptides of (b) (optionally referred to as "altered polypeptides" hereinafter) can be polypeptides comprising the amino acid sequence of SEQ ID NO 2 in which the amino acid sequence has one or several (preferably one or a few) conservative substitutions and yet having substantially the same activity as GPR120.

Herein, "conservative substitution" in this specification means one or several (preferably a few) amino acid residues are replaced with other chemically similar amino acid residues without substantially altering activity of peptides. For example, there can be mentioned a case where a hydrophobic residue is substituted by another hydrophobic residue, or a case where a polar residue is substituted by another polar residue having the same charges. Functionally similar amino acids for which such substitution can be made are publicly known in the field of the art. Specific examples of non-polar (hydrophobic) amino acids are alanine, valine, isoleucine, leucine, proline, tryptophan, phenylalanine, methionine and the like. Examples of polar (neutral) amino acid include glycine, serine, threonine, tyrosine, glutamine, asparagine, cysteine and the like. Examples of positively charged (basic) amino acid include arginine, histidine, lysine, and the like. In addition, examples of negatively charged (acidic) amino acid include aspartic acid, glutamic acid and the like.

Herein, the number of amino acids which can be deleted, substituted, inserted and/or added is, for example, 1 to 30, preferably 1 to 20, more preferably 1 to 10, even more preferably 1 to 5, and particularly preferably 1 to 2. In addition, said altered polypeptides include salts thereof, polypeptides with or without a disulfide bond, polypeptides with or without phosphorylation, and, furthermore, polypeptides with or without a sugar chain. Accordingly, sources of said altered polypeptides are not limited to human so far as these conditions are satisfied.

Altered polypeptides may further include polypeptides with alteration or modification at N-terminus (amino terminus) and C-terminus (carboxyl terminus). For example, the C-terminal carboxyl group can be carboxylate (—COO$^-$), amide (—CONH$_2$) or ester (—COOR). Moreover, said R can be, for example, a linear, branched, or circular C1-6 alkyl and C6-12 aryl group. In addition, altered polypeptides may include polypeptides with the N-terminal amino group protected by a common protective group.

Examples of said polypeptides of (b) include GPR120 or variants thereof derived from organisms other than human [for example, mammals other than human (for example, mouse, rat, hamster, pig, dog and the like), birds, reptiles, amphibians, fishes, insects and the like]. Specifically, polypeptides composed of the amino acid sequence of SEQ ID NOs 4 and 5 (mouse derived and rat derived) are included.

Said polypeptides of (c) (optionally referred to as "homologous polypeptides" hereinafter) are not limited so far as it is composed of amino acid sequences with 80% or higher identity to the amino acid sequence of GPR120, but preferably 85% or higher, more preferably 90% or higher, even more preferably 95% or higher, even further preferably 98% or higher, particularly preferably 99% or higher identity and yet has substantially the same activity as GPR120.

Any of values for "identity" used in the present specification can be values calculated using a homology search program known to a person skilled in the art, for example, values can be calculated by the homology algorithm BLAST (Basic local alignment search tool) http://www.ncbi.nlm.nih.gov/BLAST/ provided by National Center for Biotechnology Information (NCBI) using default (initially set) parameters. In addition, said homologous polypeptides include salts thereof, polypeptides with or without a disulfide bond, with or without phosphorylation, and, furthermore, polypeptides with or without a sugar chain. Accordingly, sources of said altered polypeptides are not limited to human so far as polypeptides meet these conditions. For example, GPR120 or variants thereof derived from organisms other than human [for example, mammals other than human (for example, mouse, rat, hamster, pig, dog and the like), birds, reptiles, amphibians, fishes, insects and the like is included. Specifically, polypeptides composed of the amino acid sequence of SEQ ID NOs 4 and 6 (mouse derived and rat derived) are included.

Furthermore, a partial polypeptide of GPR120 (namely, GPR120, altered polypeptides thereof, or homologous polypeptides thereof) can be used so far as it has substantially the same activity as GPR120 (for example, an activation effect mediated by arachidonic acid or γ-linolenic acid, or capability of binding to arachidonic acid or γ-linolenic acid and a variety of cell stimulating activity caused thereby, a partial polypeptide comprising the amino acid sequence corresponding to the extracellular domain). Herein, the number of amino acids composing the partial polynucleotide is 90%, 80%, 70%, 60%, 50%, 40%, 30%, 20%, 10% or 5% of the number of amino acids of GPR120.

Preparation Methods for GPR120

GPR120 (namely, GPR120, altered polypeptides, and homologous polypeptides) and their partial polypeptides used in the present invention can be prepared by various publicly known methods, for example, gene engineering methods, and synthetic methods. Specifically, when gene engineering methods are applied, these polypeptides can be prepared by inserting the polynucleotide encoding GPR120 or its partial peptide into appropriate host cells, culturing the obtained transformants under conditions which enable expression of the gene, and carrying out isolation and purification of a desired polypeptides from cultured materials using conventional methods for isolation and purification of expressed proteins. Said methods for isolation and purification include, for example, salting out with ammonium sulfate, ion-exchange chromatography using ion-exchange cellulose, molecular sieve chromatography using molecular sieve gels, affinity chromatography using protein A-bound polysaccharides, dialysis, freeze-drying and the like. In addition, when synthetic methods are applied, conventional methods of synthesis such as a liquid phase method or a solid phase method can be used, and usually an automatic synthesizer can be used. Synthesis of chemically modified compounds can be carried out using conventional methods. Moreover, a desired partial polypeptide can be prepared by enzymatic cleavage using appropriate proteases.

Among methods for preparation of GPR120 used in the present invention, gene engineering methods are described in detail in the following. These methods can be applied to prepare partial polypeptides thereof with no particular limitation so far as partial polypeptides can be used for the screening which will be described later.

Polynucleotides Encoding GPR120

Polynucleotides encoding GPR120 used in the present invention (namely, GPR120, altered polypeptides, and homologous polypeptides) are not specifically limited so far as polynucleotides encode said GPR120, said altered polypeptides, or said homologous polypeptides.

In addition, the term "polynucleotide" used in the present specification includes both DNA and RNA. Polynucleotide encoding GPR120 used in the present invention are specifically selected from the group consisting of (i)-(vi) listed below:

(i) polynucleotide composed of the base sequence of SEQ ID NO 1;

(ii) polynucleotide encoding the "polypeptide composed of the amino acid sequence of SEQ ID NO 2";

(iii) polynucleotide encoding the "polypeptide composed of the amino acid sequence of SEQ ID NO 2 and yet having substantially the same activity as said GPR120";

(iv) polynucleotide encoding the "polypeptide comprising the amino acid sequence of SEQ ID NO 2 in which one or several (preferably one or a few) amino acids are deleted, substituted, inserted and/or added at one or several sites (preferably one or a few), and yet having substantially the same activity as GPR120";

(v) polynucleotide which can hybridize with the polynucleotide composed of the base sequence of SEQ ID NO 1 under stringent conditions, and encodes a polypeptide having substantially the same activity as GPR120; and (vi) polynucleotide having 80% or higher, preferably 85% or higher, more preferably 90% or higher, even more preferably 95% or higher, even further preferably 98% or higher and particularly preferably 99% or higher identity to the base sequence of SEQ ID NO 1, and encoding a polypeptide having substantially the same activity as said GPR120.

In an aspect of the present invention, a polynucleotide encoding GPR120 used in the present invention is the polynucleotide encoding the "polypeptide comprising the amino acid sequence of SEQ ID NO 2 in which one or several (preferably one or a few) amino acids are deleted, substituted, inserted and/or added at one or several sites (preferably one or a few) and still having substantially the same activity as said GP120". Herein, the number of amino acids which may be deleted, substituted, inserted and/or added is, for example, 1-30, preferably 1-20, more preferably 1-10, even more preferably 1-5, and particularly preferably 1-2.

Variants obtained by adding, deleting and/or substituting amino acids can be prepared, for example, by conducting site-specific mutagenesis of the DNA encoding the polypeptides, a well known conventional method (for example, see Nucleic Acid Research, Vol. 10, No. 20, p. 6487-6500, 1982). The term "one or several amino acids" used in this specification refers to the certain number of amino acids which can be added, deleted, inserted and/or substituted by site-specific mutagenesis.

Site-specific mutagenesis, for example, other than a particular inconsistency which is a desired mutation, can be carried out using synthetic oligonucleotide primers complementary to a single stranded phage DNA to be mutated. Namely, complementary DNA chains are synthesized by phage using the above-mentioned synthetic oligonucleotide as a primer, and host cells are transformed by introducing the obtained double stranded DNA. Cultured materials of transformed bacteria are plated on agar plates and a plaque is made from a single cell comprising the phage. By doing so, theoretically, 50% of new colonies contain phage having mutation as a single stranded DNA and another 50% contains the original sequence. Plaques obtained are hybridized with synthetic probes labeled by kinase treatment under the temperature that the probe can hybridize with the one which perfectly coincides with a DNA having a desired mutation but can not hybridize with the original DNA. Then, plaques hybridized with the probe are picked up and cultured to recover DNA.

Meanwhile, in addition to the aforementioned site-specific mutagenesis, methods for substituting, deleting, inserting and/or adding one or several amino acids in the amino acid sequence of the biological active peptide of GPR120 without loosing its activity include a method to treat a gene with mutagen and a method to cleave and open a DNA gene, and delete, add, insert and/or substitute a selected nucleotide, and then to ligate the gene.

The term "deletion" includes deletion of amino acid residues at a terminus of the amino acid sequence and deletion of amino acid residues in the middle of the amino acid sequence.

The term "addition" also includes addition of amino acid residues at a terminus of the amino acid sequence and deletion of amino acid residues in the middle of the amino acid residues.

There are several codons encoding a single amino acid. Accordingly, any of DNA encoding the amino acid sequence or its enzyme activity domain of SEQ ID NO 2, 4, or 6 is included within the range of the present invention.

According to another aspect of the present invention, a polynucleotide encoding GPR120 used in the present invention includes of a polynucleotide which can hybridize with the polynucleotide composed of the base sequence listed as SEQ ID NO 1 under stringent conditions, and encodes a polypeptide having substantially the same activity as the aforementioned GPR120". Specifically, polynucleotides composed of the base sequence of SEQ ID NO 4 or 6 (derived from mouse and rat) are included.

In this specification, a polynucleotide which can hybridize under stringent conditions refers to, specifically, a polynucleotide with at least 70% or higher, preferably 80% or higher, more preferably 85% or higher, even more preferably 90% or higher, further more preferably 95% or higher, particularly preferably 98% or higher, and most preferably 99% or higher identity to the base sequence of SEQ ID NO 1 when identity is calculated by homology search software such as FASTA, BLAT, Smith-Waterman [Meth. Enzym., 164, 765 (1988)] using default (initially set) parameters. The "stringent" hybridization condition may be similar to the aforementioned phospholipase. The section of the aforementioned phospholipase can be referred for detailed procedure of the hybridization.

Alternatively, isoforms and allelic variants of phospholipase can be obtained from cDNA libraries and genome libraries derived from human, mouse, rat, rabbit, hamster, chicken, pig, cattle, goat, sheep and the like using primers designed based on the base sequence of SEQ ID NO 1, 3, or 5 by polymerase chain reaction technology (PCR) (Current Protocols in Molecular Biology, John Wiley & Sons (1987) Section 6.1-6.4).

A base sequence of a polynucleotide can be determined and confirmed using a conventional method. For example, sequence confirmation can be made using the dideoxynucleotide chain termination method (Sanger et al. (1977), Proc. Natl. Acad. Sci. USA 74: 5463) and the like. In addition, an appropriate DNA sequencer can be used for sequence analysis.

A polynucleotide encoding GPR120 used for the present invention can be, for example, a natural polynucleotide or a completely synthetic polynucleotide. Moreover, a polynucleotide can be synthesized from a part of a natural polynucleotide. Typical methods to obtain a polynucleotide encoding GPR120 of the present invention include, for example, a commonly used method in the field of gene engineering, for example a method to screen commercially-available libraries or cDNA libraries using appropriate DNA probes prepared based on the information of, for example, a partial polynucleotide sequence (for example, the base sequence of SEQ ID NO 1).

A polynucleotide encoding GPR120 of the present invention is preferably "a polynucleotide composed of the base sequence of SEQ ID NO 1". The base sequence of SEQ ID NO 1 has an open reading frame which starts with ATG of the nucleotide number 1-3 and ends with TAA of the nucleotide number 1084-1086. In addition, a polynucleotide composed of the base sequence of SEQ ID NOs 1 and 5 is included.

Plasmids

A plasmid used for the aforementioned transformation is not specifically limited so far as it has the polynucleotide encoding GPR120 as described above, and plasmids prepared by inserting said polynucleotide into a publicly known expression vector selected as appropriate depending on the host cell to be used.

Transformants

The aforementioned transformant also is not specifically limited so far as it has a polynucleotide encoding GPR120 as described above, for example, it can be a transformant in which said polynucleotide is incorporated into chromosome of a host cell, a transformant comprising a plasmid in which said polynucleotide is incorporated, or a transformant which is not expressing GPR120. Said transformant can be prepared, for example, by transforming a desired host cell with the plasmid or the polynucleotide itself.

Said host cells can include, for example, publicly known microorganisms commonly used such as *Escherichia coli* bacteria (for example, *Escherichia coli* 3M109), or yeast cells (for example, *Saccharomyces cerevisiae* W303), or publicly known cultured cells such as animal cells (for example, CHO cells, HEK-293 cells, or COS cells) or insect cells (for example, BmN4 cells, and Sf-9 cells).

In addition, said publicly known vectors include, for example, pUC, pTV, pGEX, pKK or pTrcHis for *Escherichia coli* bacteria; pEMBLY or pYES2 for yeast cells; pcDNA3, pMAMneo or pBabe-puro for CHO cells, HEK-293 cells and COS cells; vectors having polyhedrin promoter of Bombix mori nuclear polyhedrosis virus (BmNPV) (for example, pBK283) for BmN4 cells.

Cells containing GPR120 are not specifically limited so far as GPR120 is expressed on cell surface membranes, and, for example, can be obtained by culturing the transformants (namely, cells transformed by plasmids incorporated with the polynucleotide encoding GPR120) under conditions enabling cells to express GPR120, or by injecting RNA encoding GPR120 into appropriate cells and culturing them under conditions enabling cells to express GPR120.

Cellular Membrane Fragments

In addition, cellular membrane fragments to be used in the present invention containing GPR120 of the present invention can be obtained, for example, by breaking up cells which express said GPR120 and separating fractions which are rich in cellular membranes. Examples of methods to break up cells include a method to smash using a homogenizer (for example, Potter-Elvehjem homogenizer), grinding with a Waring blender or Polytron (Kinematica Co.), breaking using a sonicator, a method to eject cells through a narrow nozzle by pressurizing using a French press, or the like. Moreover, methods to fractionate membranes can be, for example, methods for fractionation using centrifugal force such as centrifugal fractionation, or density gradient centrifugation.

Screening Methods

As mentioned above, the present invention provides a method using biomembranes containing GPR120 or cells containing said biomembranes, and phospholipase or salts thereof to screen for a substance which alters the interaction between GPR120 and phospholipase or salts thereof. Preferably, this method comprises making a contact between biomembranes containing GPR120 or cells containing said biomembranes, and phospholipase or salts thereof, and measuring and comparing cell stimulating activities in the presence and absence of a substance of interest.

According to a more preferable aspect of the invention, the method further comprises the step of determining whether the substance alters GPR120 mediated cell stimulating activity when there is a difference in the results in the presence and absence of the substance of interest.

According to this screening method, substances of interest (test compounds) can be screed for a stimulatory activity or an inhibitory activity distinctively on GPR120 functions. Namely, this screening method enables screening for a compound which alters the interaction between phospholipase and GPR120, specifically, screening for a compound which affects activation of GPR120, more specifically, screening for a substance which alters GPR120 mediated cell stimulating activity, even more specifically, screening for a substance which stimulates GPR120 function (an agonist), or for a substance which inhibits GPR120 function (an antagonist).

Accordingly, if the cell stimulating activity in the presence of a substance of interest is higher compared to the cell stimulating activity in the absence of the substance of interest, the substance of interest can be determined as a stimulatory substance of GPR120 function (a GPR120 agonist). If the cell stimulating activity in the presence of a substance of interest is lower than the cell stimulating activity in the absence of the substance of interest, the substance of interest can be determined as an inhibitory substance of GPR120 function (a GPR120 antagonist).

According to a preferable aspect of the present invention, cell stimulating activities can be measured by a reporter assay system detecting changes in translation and transcription of reporter genes by the production of signal transduction materials, or by measuring a parameter selected from the group consisting of a release of intracellular $Ca^{2+}$, an activation of adenylate cyclase, a production of intracellular cAMP, a production of intracellular cGMP, a release of arachidonic acid, a release of acetylcholine, a production of inositol phosphate, changes in cell membrane potential, phosphorylation or activation of intracellular proteins, a pH changing activity, phosphorylation or activation of MAP kinase, an activation of c-fos, a glycerol production activity, a lipolytic activity, adrenocorticotrophic hormone (ACTH) secretion activity, chorecystokinin (CCK) secretion activity, glucagon like peptide (GLP-1) secretion activity and the like. More preferably, a reporter assay system or an increase of intracellular $Ca^{2+}$ concentration can be measured.

In the present invention, for example, a GPR120 mediated increase in intracellular $Ca^{2+}$ concentration or an increase in transcription of a reporter gene can be measured by a publicly known method, compounds can be screened for a stimulatory activity or an inhibitory activity distinctively on GPR120 mediated functions. This is based on the application of an intracellular signal transduction caused by the interaction of phospholipase with GPR120 such as, for example, an elevation of intracellular calcium concentration.

For example, if phospholipase interacts with cells derived from mammals (for example, HEK-293 cells or CHO cells) expressing GPR120 on cell membrane (preferably, over-expressing by introduction of an expression vector containing GPR120), an intracellular $Ca^{2+}$ concentration increases.

When compounds are screened for a stimulatory activity on GPR120 functions, instead of a substance capable of activation of GPR120 mediated cell stimulation in this screening system (for example, phospholipase), a compound may be preferably selected by bringing a substance of interest alone in contact with cells to elevate intracellular $Ca^{2+}$ concentration.

When compounds are screened for an inhibitory activity on GPR120 functions, phospholipase or salts thereof and a substance of interest may be added to the screening cells. An intracellular calcium concentration elevates in response to the activity of phospholipase, however, if a substance of interest antagonizes the activity of phospholipase, an elevation in intracellular calcium concentration is suppressed. In this case, said substance of interest can be selected as an inhibitory compound of GPR120 functions.

Intracellular calcium concentration can be measured, for example, using calcium fluorescent probes (for example, Fura-2, and Fluo-3). In addition, commercially-available calcium measurement kits can be used.

In the present invention, moreover, compounds can be screened for a stimulatory activity or an inhibitory activity distinctively on GPR120 functions using cells expressing GPR120 on cell membrane (preferably, over-expressing by introduction of an expression vector containing GPR120), and furthermore containing a reporter gene with a cAMP responsive element (CRE) located 5'-upstream (for example, alkaline phosphatase gene, luciferase gene, β-lactamase gene, nitroreductase gene, chloramphenicol acetyltransferase gene, β-galactosidase gene and the like, or fluorescent protein genes such as green fluorescent protein (GFP) gene) (optionally referred to as "cells for screening" hereinafter). In this case, an activation of transcription of a reporter gene with CRE in a promoter domain introduced into said cells for screening caused by miscellaneous intracellular signal transduction in the cells is utilized.

In the following, procedures to screen compounds for a stimulatory activity or an inhibitory activity distinctively on GPR120 functions are described in more detail.

In the aforementioned cells introduced with a reporter gene having said CRE in the promoter domain, for example, an expression level of a reporter gene becomes elevated when intracellular cAMP concentrations increase or intracellular $Ca^{2+}$ concentrations increase. In addition, activities can be measured while basic cellular levels of cAMP are elevated by addition of an activating reagent for adenylate cyclase (for example, forskolin and the like). Expression levels of reporter gene products can be measured by measuring luminescence derived from the amount of a luminescent substance produced from a substrate reacted with a reporter gene product which is included in the supernatant of a cell culture or in the extract of a cell, or measuring fluorescence derived from fluorescent protein produced as a reporter gene.

Moreover, if phospholipase or salts thereof are added, as a result of activation of intracellular signal transduction (for example, an increase in intracellular $Ca^{2+}$ concentration), an expression level of a reporter gene is elevated. Thus, if compounds are screened for a stimulatory activity on GPR120 functions, instead of a substance capable of activating GPR120 mediated cell stimulation, a compound may be preferably selected by bringing a substance of interest alone in contact with cells in this screening system to increase expression levels of a reporter gene product.

If compounds are screened for an inhibitory activity on GPR120 functions, phospholipase and salts thereof and a substance of interest may be preferably added to cells for screening. In addition, activities can be measured while basic cellular levels of cAMP are elevated by addition of an activating reagent for adenylate cyclase (for example, forskolin and the like). By an effect of phospholipase, an expression level of a reporter gene product increases in the culture supernatant or in the cell, however, if a substance of interest antagonizes the action of phospholipase, an expression of a reporter gene product is suppressed. In this case, said substance of interest can be selected as a compound to inhibit GPR120 functions.

It can be easily confirmed whether an effect of a substance of interest is mediated via GPR120 or not. For example, in parallel with said test using cells for screening (namely, cells expressing GPR120 on cell membrane and having a reporter gene with CRE located 5'-upstream), a similar test using control cells (for example, cells having a reporter gene with CRE located 5'-upstream but not expressing GPR120 on cell membrane) is carried out. As a result, when an effect of the substance of interest is not mediated by its binding to GPR120, the same effects on expression levels of a reporter gene product are observed between cells for screening and control cells, while if an action of the aforementioned substance of interest is mediated by its binding to GPR120, different effects on expression levels of a reporter gene product are observed between cells for screening and control cells.

In another aspect of the present invention, substances can be screened for altering binding between phospholipase and GPR120 as a substance to alter the interaction between phospholipase and GPR120. In this case, the screening method of the present invention comprises the following steps: making a contact between biomembranes expressing GPR120 or cells comprising said membranes, and phospholipase or salts thereof in the presence or absence of a substance of interest, measuring an amount of binding of phospholipase or its salts to biomembranes containing GPR120 or cells containing said biomembranes, and comparing the amounts of binding in the presence and absence of a substance of interest. According to this screening method, compounds can be screened for a stimulatory activity or an inhibitory activity indistinctively. That is, when the method of the aspect can be applied, screening for a substance which alters the interaction between phospholipase and GPR120 can be carried out, specifically, screening for a compound which alters the binding ability of phospholipase to GPR120, more specifically, screening for a compound which is capable of stimulating or inhibiting GPR120 functions can be carried out.

Specifically, a screening for a compound can be carried out without distinguishing the ability to stimulate or inhibit GPR120 functions by making a contact between GPR120 and labeled phospholipase in the presence and absence of a substance of interest, and comparing the amounts of specific phospholipase binding to GRP120 under said conditions. That is, said amount of specific phospholipase binding to GPR120 in the presence of a substance of interest is decreased compared to the amount of specific phospholipase binding to GPR120 in the absence of a substance of interest, the substance of interest can be determined as a substance capable of altering the interaction between phospholipase and GPR120, specifically, the substance of interest can be determined as a compound capable of altering the binding ability of phospholipase binding to GPR120, more specifically, the substance of interest can be determined as a GPR120 agonist or a GPR120 antagonist.

When an amount of binding is measured, phospholipase or its salts can be labeled. Said labeling substances include, for example, radio-isotopes, enzymes, fluorescent substances, and luminescent substances. For radio-isotopes, for example, $[^3H]$, $[^{14}C]$, $[^{125}I]$, and $[^{35}S]$ can be used. For said enzymes, for example, β-galactosidase, alkaline phosphatase, peroxidase and the like can be used. For fluorescent substances, for example, fluorescent isothiocyanate, BODIPY and the like can be used. For luminescent substances, for example, luciferin, lucigenin and the like can be used. In addition, a chimeric protein between phospholipase and a marker protein (for example, GFP and the like) can be prepared using gene engineering methods.

Moreover, since GPR120 has been suggested its involvement in secretion of cholecystokinin (CCK) and glucagon like peptide-1 (GLP-1), a compound obtained by the screening method of the present invention can be administered in human or organisms other than human [for example, non-human mammals (for example, cattle, monkey, bird, cat, mouse, rat, hamster, pig, dog and the like), birds, reptiles, amphibians, fishes, insects and the like], and by analyzing using cellular concentration of gastrointestinal hormones (for example, an amount of CCK and GLP-1, and the like) as an index, or analyzing using post-dose autonomic motions as an index, it is possible to confirm and determine whether or not the compound is effective against eating disorders represented by anorexia and hyperphagia, obesity and its associated diabetes, diabetic complications such as diabetic retinitis, or diabetic nephropathy, hyperlipidemia, arteriosclerosis, hypertension, regulation of digestive functions, pituitary hormone secretion, and stress control. The aforementioned mammals are not limited to normal animals and animal models of genetic diseases and gene-manipulated animals can be also used. Administration routes of the substance of interest can be oral or parenteral. Parenteral administration routes include, for example, intravenous, intraarterial, subcutaneous, intraperitoneal, intratrachial, intrarectal, and intracerebral administration, preferably, intraventricular administration in close proximity to hypothalamus. It is also effective to perform tests for measurement of, for example, motility of gastrointestinal tracts, contraction of gallbladder, gastrointestinal hormone secretion, pituitary hormone secretion, weight change, insulin secretion, and blood lipid level as an index for screening. Number of administration of a substance of interest can be once or several times per day, and an administration period or observation period of a substance of interest can be from one day to several weeks.

Substances of interest used in the present invention can be any kind of compounds and include, for example, expression products of gene libraries, synthetic small molecule libraries, nucleic acids (oligo DNA, oligo RNA), synthetic peptide libraries, antibodies, bacterial secreted substances, cell (microorganisms, plant cells, animal cells) extracts, cell (microorganisms, plant cells, animal cells) culture supernatants, purified or partially purified polypeptides, extracts derived from marine organisms, plants or animals, soil, and random phage peptide display libraries.
Kit for Screening A screening kit according to the present invention includes, at least, biomembranes containing GPR120 or cells including said membranes, phospholipase or salts thereof. Preferably, this kit is for screening substances which alter GPR120 mediated cell stimulating activity. Said screening kit can further include, if desired, miscellaneous reagents to implement the screening method of the present invention, for example, buffer solutions for binding reaction, buffer solutions for washing, instructions and/or apparatuses and the like.

The screening kit in another aspect of the present invention includes, at least, phospholipase or salts thereof, and cells expressing GPR120 on cell membrane (preferably, over-expressing by introduction of an expression vector containing GPR120) and containing a reporter gene with cAMP responsive element (CRE) located 5' upstream (for example, alkaline phosphatase gene, luciferase gene, and the like). Said screening kit can further include, if desired, miscellaneous reagents such as, for example, substrates for reporter gene products (for example, alkaline phosphatase or luciferase and the like), activation agents for adenylate cyclase (for example, forskolin), buffer solutions for binding reaction, buffer solutions for washing, instructions and/or apparatuses. In addition, said screening kit may include cells having a reporter gene with CRE located 5'-upstream, but not expressing GPR120 on the cell membrane as a control.

The screening kit in another aspect of the present invention includes, at least, phospholipase or salts thereof, and cells expressing GPR120 on the cell membrane (preferably, over-expressing by introduction of an expression vector containing GPR120). Said screening kit can further include, if desired, miscellaneous reagents such as, for example, calcium fluorescent probes (for example, Fura-2 and the like), buffer solutions for binding reaction, buffer solutions for washing, instructions, and/or apparatuses. In addition, said screening kit may include cells not expressing GPR120 on the cell membrane as a control.

Pharmaceutical Preparations Comprising a Compound Obtained by the Screening Method of the Present Invention High levels of GPR120 expression were detected, as shown in Examples 8, and 28-33 described later, in the pituitary gland, lung, intestinal tracts (particularly, in the ileum, cecum and large intestine), testis, prostate gland, thyroid gland, adrenal gland, miscellaneous types of adipose tissues (subcutaneous fat, mesenteric fat, epididymal fat, and brown fat), alveolar macrophages, dendritic cells, and lymph nodes. Among them, high levels of GPR120 expression were detected in the pituitary gland, lung, alveolar macrophages, adipose tissues, dendritic cells, and the like. Thus, according to the present invention, substances useful for prevention or therapeutic treatment for diabetes, diabetic complications such as diabetic retinopathy or diabetic nephropathy, hyperlipidemia, arteriosclerosis, angina, myocardial infarction, pituitary dysfunction, mental disorders, immunological diseases, inflammatory diseases, macrophage and dendritic cell related diseases, cancer, typical eating disorders such as anorexia and hyperphagia, and furthermore, its associated diseases of large intestine. Moreover, GPR120 has been reported to be involved in stimulatory activity on cholecystokinin (CKK) secretion from intestinal secretory cell line STC-1 (Japanese Patent Application Laid-Open Publication No. 2005-15358). CCK also suppresses eating action regulated by vagus nerve in peripheral region. CCK is released from gastrointestinal organs such as stomach and duodenum and has a variety of functions such as gastric acid secretion, gallbladder contraction, stimulation of pancreatic enzyme secretion and intestinal peristalsis as a gastrointestinal hormone. Based on these, it is predicted that GPR120 is involved in eating disorders represented by anorexia and hyperphagia, obesity and its associated diabetes, hypertension, arteriosclerosis and regulation of gastrointestinal functions.

Furthermore, GPR120 has been reported to stimulate a release of glucagon like peptide-1 (GLP-1) from intestinal secretory cell line STC-1 (Akira Hirasawa et al., Nature Medicine, 11, 90-94, 2004). Since GLP-1 is an important hormone involved in a stimulation of insulin secretion and a metabolic homeostasis, it is predicted that GPR120 is involved in metabolic diseases.

In addition, an elevation of GPR120 mRNA expression level was detected in the pituitary gland of rats subjected to restraint and water immersion stress, suggesting the involvement of GPR120 in stress control (International Publication WO2004/065960). Moreover, an expression level of GPR120 is high in pituitary gland suggesting its involvement in pituitary hormone secretion (for example, ACTH and the like).

Accordingly, compounds obtained by the screening method of the present invention can be used as drugs for treating eating disorders represented by anorexia and hyperphagia, obesity and its associated diabetes, hyperlipidemia, arteriosclerosis, hypertension, immunological diseases, inflammatory diseases, cancer and the like, regulatory agents for gastrointestinal functions, agents for improving abnormal secretion of pituitary hormones and stress control drugs.

Thus, compounds obtained by the screening method of the present invention are effective compounds to treat eating disorders represented by anorexia and hyperphagia, obesity and its associated diabetes, hyperlipidemia, arteriosclerosis, hypertension, immunological diseases, inflammatory diseases, cancer and the like, and gastrointestinal malfunctions, and furthermore, abnormal secretion of pituitary hormones, stress syndromes and the like.

Said compounds can be salts thereof, and moreover, the compounds and salts thereof can be solvates (for example, hydrates, alcohol hydrates and ether hydrates). Herein, "salts" refers to pharmacologically acceptable salts which are not specifically limited so long as they can form pharmacologically acceptable salts with a compound obtained by the screening method of the present invention. Specifically, those include, preferably, hydrohalide salts (for example, hydrofluoride, hydrochloride, hydrobromide, hydroiodide and the like), inorganic acid salts (for example, sulfates, nitrates, perchlorates, phosphates, carbonates, bicarbonates and the like), organic carbonates (for example, acetates, oxalates, maleates, tartrates, fumarates, citrates and the like), organic sulfonates (for example, methanesulfonates, trifluoromethanesulfonates, ethanesulfonates, benzenesulfonates, toluenesulfonates, camphorsulfonates and the like), amino acid salts (for example, aspartates, glutamates and the like), quaternary amine salts, alkaline metal salts (for example, sodium salts, potassium salts and the like), and alkaline earth metal salts (for example, magnesium salts, calcium salts and the like).

Compounds obtained by the screening method of the present invention can be used alone, but also can be used as pharmaceutical compositions by combining with pharmacologically acceptable carriers. Herein, the ratio of an active ingredient to carriers can be variable between 1-90 wt %. In addition, the pharmaceutical composition can be administered to human or organisms other than human [for example, non-human mammals (for example, cattle, monkey, bird, cat mouse, rat, hamster, pig, dog and the like), birds, reptiles, amphibians, fishes, insects and the like] in a variety of dosage forms by either oral or parenteral (for example, intravenous injection, intramuscular injection, subcutaneous administration, rectal administration, transdermal administration). Accordingly, pharmaceutical compositions comprising a compound obtained by the screening method of the present invention can be prepared as appropriate dosage forms depending on its administration route which include, specifically, oral forms such as tablets, capsules, granules, powders and syrups, or parenteral forms such as injections, drip injections, liposomes, suppositories. These preparations can be made with commonly used excipients, binders, disintegrators, lubricants, coloring agents, flavoring agents, and, if necessary, stabilizers, emulsifiers, absorption stimulators, surfactants, pH adjusters, antiseptics, antioxidants, extenders, wetting agents, surface activation agents, dispersing agents, buffering agents, preservatives, dissolution aids, soothing agents and the like, and can be formulated by combining with ingredients generally used for pharmaceutical preparations using a conventional method. These usable and non-toxic ingredients include, for example, plant and animal oils such as soybean oil, beef tallow, synthetic glycerides and the like; hydrocarbons, for example, liquid paraffin, squalane, solid paraffin and the like; ester oils, for example, myristic acid octyldodesyl, myristic acid isopropyl and the like; higher alcohols, for example, cetostearylalcohol, behenylalcohol and the like; silicone resins; silicone oils; surfactants, for example, polyoxyethylene fatty acid ester, sorbitan fatty acid ester, glycerin fatty acid ester, polyoxyethylene sorbitan fatty acid ester, polyoxyethylene cured castor oil, polyoxyethylene/polyoxypropylene block polymer, and the like; water soluble polymers, for example, hydroxyethyl cellulose, polyacrylic acid, carboxyvinyl polymer, polyethylene glycol, polyvinylpyrrolidone, methyl cellulose and the like; lower alcohols, for example, ethanol, isopropylalcohol and the like; polyols, for example, glycerin, propyleneglycol, dipropyleneglycol, sorbitol, polyethyleneglycol and the like; saccharides, for example, glucose, sucrose and the like; inorganic powders, for example, silicic acid anhydride, aluminium magnesium silicate, aluminium silicate; inorganic salts, for example, sodium chloride, sodium phosphate and the like; and purified water and the like using a conventional method. The aforementioned usable and non-toxic excipients include, for example, lactose, fructose, cornstarch, sucrose, glucose, mannitol, solbit, crystalline cellulose, silicone dioxide and the like. Binders include, for example, polyvinylalcohol, polyvinylether, methylcellulose, ethylcellulose, gum Arabic, tragacanth, gelatin, shellac, hydroxypropylmethylcellulose, hydroxypropylcellulose, polyvinylpyrrolidone, polypropyleneglycol/polyoxyethylene block polymer, meglumine and the like. Disintegrators include, for example, starch, agar, gelatin powder, crystalline cellulose, calcium carbonate, sodium bicarbonate, calcium citrate, dextrin, pectin, carboxymethylcellulose calcium and the like. Lubricants include, for example, magnesium stearate, talc, polyethyleneglycol, silica, cured plant oils and the like. Coloring agents include additives approved for pharmaceutical use. Flavoring agents include cocoa powder, menthol, empasm, peppermint oil, borneol, cinnamon powder and the like. The ingredients listed above can be salts thereof or hydrates thereof.

Dosage forms and/or a required dosage range depend on a selection of compounds obtained by the screening method of the present invention, subjects to be administered, administration routes, properties of preparations, patient's conditions and physician's judgment. However, a range of appropriate dosages is, for example, about 1.0-1,500 µg per 1 kg body weight, preferably, about 10-500 µg per 1 kg body weight. Taking efficacy differences in different administration routes into consideration, dosages required are predicted to be widely changed. For example, a higher dosage will be required for oral administration than for intravenous injection. These changes in dosage can be adjusted using standard optimization procedures based on experiences which are well appreciated in the field of the art.

In the present specification, "therapeutic treatment" generally refers to obtaining a desired pharmacological efficacy and/or physiological efficacy. An efficacy is preventative in a sense that a compound prevents diseases and/or symptoms completely or partially, and therapeutic in a sense that a compound heals bad effects caused by diseases and/or symptoms completely or partially. In this specification, "therapeutic treatment" includes optional therapeutic treatments for diseases in mammals, particularly in humans, for example, (1A) preventing a disease or a symptom in patients who have a predisposition to the disease or symptom but have not been diagnosed;
(1B) inhibiting symptoms of a disease, namely, blocking or delaying progress thereof; and/or
(1C) relieving symptoms of a disease, namely, setting a disease or a symptom back, or reversing the progress of a disease.

EXAMPLES

The present invention will be described in detail in the following with examples which are not intended to limit the invention.

Example 1

Preparation of a Polynucleotide Encoding GPR120

(1) Preparation of a Polynucleotide Encoding Human GPR120

For isolation of a polynucleotide encoding human GPR120 (optionally referred to simply as GPR120 or hGPR120 hereinafter), a pair of primers, a 5'-primer (5'-GATATCGCCGC-CACCATGTCCCCTGAATGCGCGCGGGCA-3') (SEQ ID NO 7) and a 3'-primer (5'-GATATCTTAGCCA-GAAATAATCGACAAGTC-3') (SEQ ID NO 8), were designed based on the nucleic acid sequence of 1086 bp of SEQ ID NO 1.

A template cDNA was obtained by reverse transcription of RNA prepared from human colon cancer cell line, Caco-2 cells. Specifically, total RNA was extracted from Caco-2 cells (ATCC) cultured in a 75 cm$^2$ flask using RNeasy Mini Kit (QIAGEN, Co) according to the manual. Then reverse transcription was carried out using TaqMan Reverse Transcription Reagents (Applied Biosystems, Co.) at 25° C. for 10 min, at 48° C. for 60 min, and at 95° C. for 10 min. Using the cDNA obtained as a template, PCR reaction was carried out at 95° C. for 5 min and followed by repeating 35 cycles of reaction at 95° C. for 1 min, at 57° C. for 1 min, and at 72° C. for 3 min, with a final elongation reaction at 72° C. for 7 min using a pair of PCR primers consisting of SEQ ID NOs 7 and 8 and Expand High Fidelity PCR System (Roche Diagnostics, Co). Amplified PCR products of about 1.1 kbp were inserted into pCR2.1 (Invitrogen, Co.) and the sequence was confirmed using an ABI prism DNA sequencing kit (Perkin-Elmer Applied Biosystems, Co.). As a result, the sequence of 1086 base pairs inserted into pCR2.1 was identical to the sequence from nucleotide number 1 to 1086 of SEQ ID NO 1 and GPR120-pCR2.1 was obtained.

(2) Preparation of a Polynucleotide Encoding Mouse GPR120

For isolation of a polynucleotide encoding mouse GPR120 (referred to as mGPR120 hereinafter), a pair of PCR primers, which were a 5'-primer (5'-GATATCGCCGCCACCATGTC-CCCTGAGTGTGCACAGACGACG-3') (SEQ ID NO 9) and a 3'-primer (5'-GATATCTTAGCTGGAAATAACAGA-CAAGTCA-3') (SEQ ID NO 10) were designed based on the sequence of 1086 bp of SEQ ID NO 3 according to a conventional method. RNA prepared from colon of a 6-week old C57BL/6CrSlc mice (Japan SLC, Inc.) using RNeasy Mini Kit (QIAGEN, Co.) was used as a template, to carry out RT-PCR using the aforementioned primers of SEQ ID NOs 9 and 10, Taq Man reverse transcription reagents, and Ampli-TaqGold (Applied Biosystems, Co.). Amplified PCR products were inserted into pCR2.1 and the sequence was confirmed according to a conventional method. As a result, the cDNA sequence of 1086 bp inserted was identical to the sequence from nucleotide number 1 to 1086 of SEQ ID NO 3 and mGPR120-pCR2.1 was obtained.

Example 2

Preparation of a Retrovirus Vector Plasmid

By cleaving pBabe Puro (Morgenstern, J. P. and Land, H. Nucleic Acid Res. 18(12):3587-96, 1990) (SEQ ID NO 11) with SalI and ClaI, SV40 promoter-puro(r) domain was removed and terminals were blunted using Klenow fragment (Takara Shuzo, Co., Ltd.). Into this site, IRES-hyg(r) domain which is pIREShyg (Clontech, Co.) cleaved out with NsiI and XbaI and blunted with T4 polymerase (Takara Shuzo, Co., Ltd.) was inserted and pBabeXIH was obtained.

This BabeXIH was cleaved with SspI and BamHI, and 5'-LTR-packaging signal was deleted. Into this site, 5'-LTR-CMV promoter-packaging signal cleaved out from pCLXSN (IMGENEX Co.) with SspI and BamHI was inserted and pBabeCLXIH was obtained.

Example 3

Preparation of a Retrovirus Vector Plasmid for Introduction of Genes for GPR120 and mGPR120

The retrovirus expression plasmid pBabeCLXIH obtained in Example 2, was cleaved with a restriction enzyme, HpaI. Into this site, cDNA encoding GPR120 cleaved out using EcoRV, from GPR120-pCR2.1 obtained in Example 1 (1) was inserted and pBabeCL(GPR120)IH was obtained (FIG. 1). Similarly, pBabeCL(mGPR120)IH was obtained using mGPR120-pCR2.1 obtained in Example 1 (2).

Example 4

Preparation of a Retrovirus Vector for Introduction of Genes for GPR120 and mGPR120

$2 \times 10^6$ 293-EBNA cells (Invitrogen, Co.) were cultured with 10 mL of DMEM medium (Sigma, Co.) (containing 10% fetal bovine serum (FBS), penicillin 100 units/mL, streptomycin 100 µg/mL) (referred to as "EBNA medium" hereinafter) in a collagen coated dish of a 10 cm diameter (Asahi Technoglass, Co.). On the following day, 3.3 µg each of pV-gp (prepared by cleaving pVpack-GP (Stratagene, Co.) with NsiI and XbaI to delete IRES-hisD and blunting with T4 polymerase followed by auto-cyclization), pVPack-VSV-G (Stratagene, Co.), and the retrovirus vector plasmid for introduction of genes obtained in Example 3 (pBabeCL(GPR120) IH or pBabeCL(mGPR120)IH) was transfected to 293-EBNA cells using a lipofection reagent, FuGENE 6 Transfection Reagent (Roche Diagnostics, Co.). Culture media were collected 24 hours after transfection and centrifuged at 1,200×g for 10 min. The supernatant was filtered through a 0.45 µm filter (Millipore, Co.) and retrovirus vectors for introduction of GPR120 and mGPR120 genes were obtained.

Example 5

Construction of SE302 Cells Introduced with a Reporter Gene Comprising a Cyclic AMP Responsive Element (1) Preparation of a Reporter DNA Comprising a Cyclic AMP Responsive Element According to the method by Durocher, Y. et al., (Anal. Biochem., 284(2):316-26, 2000), a reporter gene unit responsive to cyclic AMP (cAMP) for transcription was constructed as follows.

To prepare a unit containing cAMP responsive element (CRE), oligo. DNAs of SEQ ID NO 12 (5'-cccaagcttgatatcgaattcgacgtcacagtatgacggccatggaattcgacgtcac agtatgacggccatggggatcccg-3') and of SEQ ID NO 13 (5'-cgggatccccatggccgtcatactgtgacgtcgaattcccatggccgtcatactgtgacgtcgaattcgatatcaagcttggg-3') for CREx2hb, and of SEQ ID NO 14 (5'-tgcactgcaggaattcccatggccgtcatactgtgacgtcgaattcccatggccgtcata ctgtgacgtcggatcccg-3'0 and of SEQ ID NO 15 (5'-cgggatccgacgtcacagtatgacggccatgggaattcgacgtcacagtatgacggcc atgggaattcctgcagtgca-3') for CREx2 bp were prepared according to a conventional method. Each pair of oligo DNAs were heat treated at 95° C. and left by gradually lowering the temperature to room temperature in order to form double-stranded DNA molecules (CRE2xhb and CREx2 bp). CRE2xhb was digested with HindIII and BamHI and CREx2 bp was digested with BamHI and PstI, while pBluescriptIISK(+) (Stratagene, Co.) was digested with HindIII and PstI. Digested DNA molecules were purified by electrophoresis to isolate DNA molecules with restriction enzyme sites at both terminals, then these 3 DNA molecules (CREx2hb, CREx2 bp and pBluescriptSK (+)) were ligated together. The sequence of the plasmid obtained was analyzed and CRE4/pBluescriptIISK(+) was prepared.

Next, to obtain DNA containing a VIP (vasoactive intestinal peptide) promoter, a pair of PCR primers, a 5'-primer (5'-tcgactgcagcccatggccgtcatactgtg-3') (SEQ ID NO 16) and a 3'-primer (5'-tgcactgcaggtcggagctgactgttctgg-3') (SEQ ID NO 17), were prepared according to a conventional method.

Figure 2:
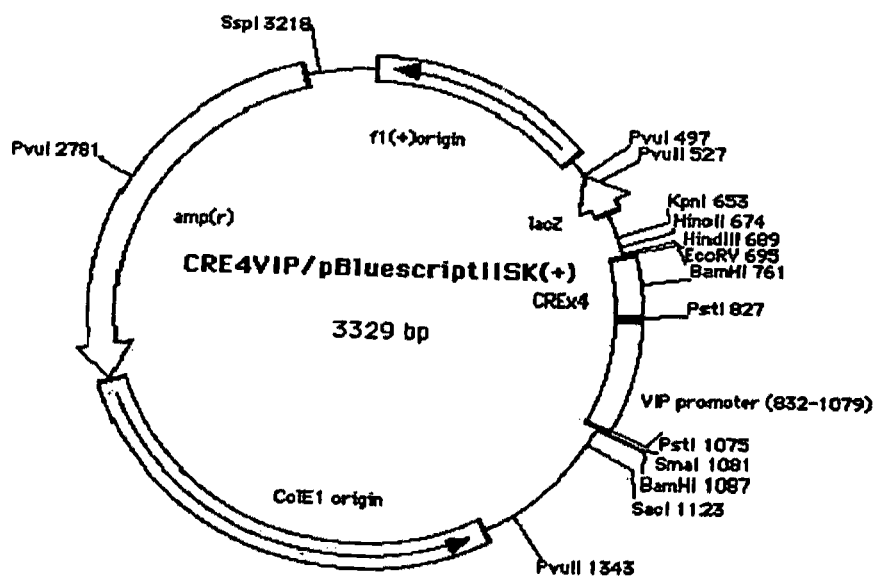
FIG. 2 shows the construction of CRE4VIP/pBluescriptI-ISK (+).

Using human genome DNA (Roche Diagnostics, Co.) as a template, and using the aforementioned PCR primers of SEQ ID NOs 16 and 17, and recombinant Taq polymerase (Takara Co.), PCR was carried out by repeating 35 cycles of reaction at 94° C. for 30 sec, at 55° C. for 30 sec, and at 72° C. for 1 min, and a DNA of 264 bp (SEQ ID NO 18) was obtained. This DNA of 264 bp was digested with PstI and inserted into CRE4/pBluescriptIISK(+) at PstI site. The sequence of the plasmid obtained was confirmed and CRE4VIP/pBluescriptIISK(+) was prepared (FIG. 2). This CRE4VIP/pBluescriptIISK(+) was digested with HindIII and SmaI and the terminals of CRE4VIP promoter fragments were blunted.

Figure 3:
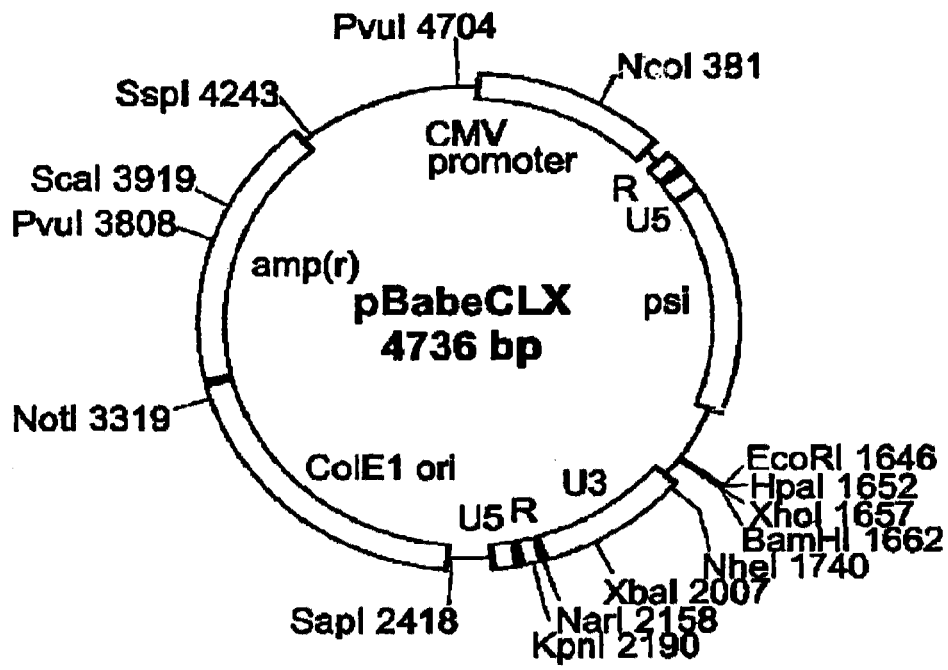
FIG. 3 shows the construction of pBabeCLX.
Figure 4:
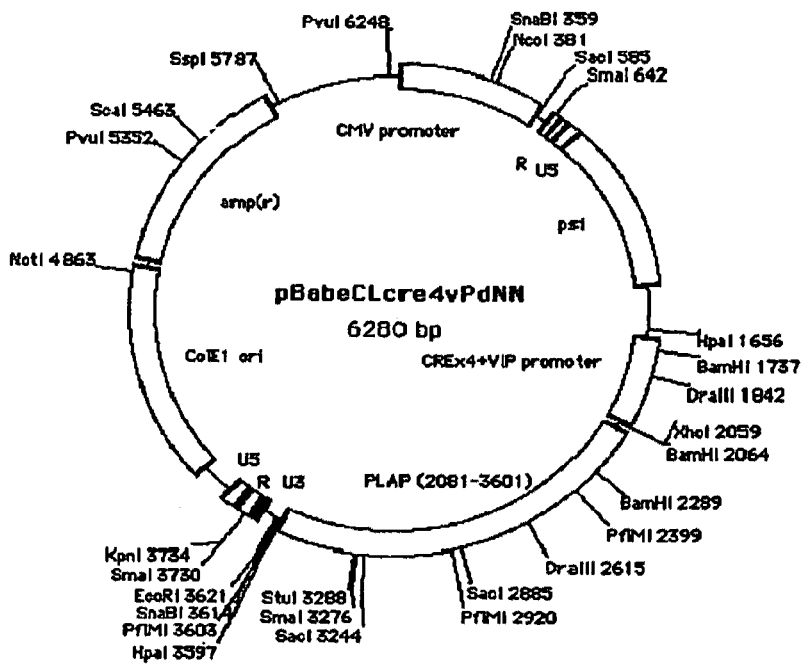
FIG. 4 shows the construction of pBabeCLcre4vPdNM.

The domain of IRES-hyg(r) was deleted from pBabe-CLXIH obtained in Example 2 and pBabeCLX was prepared (FIG. 3). A retrovirus vector plasmid for introduction of an exogenous promoter obtained by deleting the domain of NheI-NarI in the enhancer activity (LTR) originated from retrovirus from PBabeCLX was introduced with the aforementioned blunted CRE4VIP promoter fragment and placental alkaline phosphatase (PLAP), a reporter gene (Goto, M. et. al., Mol. Pharmacol. 49(5):860-73, 1996), and pBabeCLcre4vPdNN, was obtained (FIG. 4).

(2) Establishment of SE302 Cells Introduced with a Reporter Gene Comprising a Cyclic AMP Responsive Element Using a retrovirus vector plasmid pBabeCLcre4vPdNN capable of inducing a reporter PLAP gene by a cyclic AMP responsive element sequence, a retrovirus vector was prepared according to the method described in Example 4. The retrovirus vector prepared was introduced into HEK293 cells and cells were cloned by a limiting dilution method. The clone which showed the best response in PLAP induction (referred to as "SE302" hereinafter) was used for the following experiments.

Example 6

Preparation of GPR120-SE302 Cells by Virus Vector

The SE302 cells constructed in Example 5 were seeded onto a collagen coated 6 well plate (Asahi Technoglass, Co.) at $1.2\times10^5$ cells per well. Cells were cultured with 2 mL/well of DMEM medium (Sigma, Co.) (containing 10% FBS, penicillin 100 units/mL and streptomycin 100 μg/mL). On the following day, solutions of the virus vector containing GPR120 or mGPR120 obtained in Example 4, and polybrene (also called hexadimethrine bromide, Sigma, Co.) at a final concentration of 8 μg/mL were added to SE302 cells. Cells were cultured with the medium containing 500 μg/mL of hygromycin (Invitrogen, Co.) and cells grown under this condition were used for experiments as SE302 cells introduced with GPR120 gene, and SE302 cells introduced with mGPR120 gene (referred to as "GPR120-SE302 cells" and "mGPR120-SE302 cells", respectively hereinafter).

Example 7

Measurement of Transcription Activity in SE302 Cells Introduced with Genes

The aforementioned GPR120-SE302 cells or mGPR120-SE302 cells constructed in Example 6 were suspended in the culture medium for measurement of transcription activity (DMEM containing FBS which was heat-treated at 65° C. for 30 min at a final concentration of 10%) and seeded onto a 96 well plate (Becton Dickinson, Co.) at $1\times10^4$ cells/well. In addition, as control cells, SE302 cells expressing green fluorescent protein (GFP, Invitrogen, Co.) (referred to as "GFP-SE302 cells" hereinafter) were used. Specifically, GFP-302 cells were prepared by obtaining a virus for expressing GFP using the method shown in Example 3 and 4, and transfecting SE302 cells with the virus using the method shown in Example 6. Cells were cultured for 24 hours after seeding, and forskolin prepared at a final concentration of 1.0 μM and a sample were added. Cells were cultured for another 24 hours and 5 μL of the cell supernatant was recovered and transferred to a polypropylene 384-well white plate (Nalge Nunc International, Co.). Then, 20 μL of the assay buffer (280 mmol/L $Na_2CO_3$—$NaHCO_3$, 8 mmol/L $MgSO_4$, pH 10) and 25 μL of Lumiphos530 (Lumigen, Co.) were added. Following a 2-hour reaction at room temperature, chemiluminescence in each well was measured using a Fusion plate reader (Perkin Elmer, Co.) and was defined as the transcription activity. Based on these measured values, stimulation/inhibition of transcription activity was calculated using the equation (I) shown below and described as [% of control]. Activities of the group with a sample added were calculated using the value of control placed on each plate.

$$[\% \text{ of control}] = (X-C)/(F-C) \times 100 \quad (I)$$

Herein, in the above equation:
X: PLAP transcription activity in the group added with a sample,
F: Mean value of transcription activities in 2 wells of a positive control (no sample added, stimulated with forskolin),
C: Mean value of transcription activities in 2 wells of a negative control (no sample added, not stimulated with forskolin).

Example 8

Tissue Distribution of GPR120 Expression in Mouse by SYBR Green PCR Method

For quantitation of mRNA expression levels, ABI PRISM 7700 Sequence Detector (Applied Biosystems, Co.) was used. Primers used for quantitation of expression levels, 5'-primer (5'-TCCGAGTGTCCCAACAAGACT-3') (SEQ ID NO 19) and 3'-primer (5'-GGATCAAGATGAGGAG-GATGG-3') (SEQ ID NO 20), were designed based on the sequence of mouse GPR120 (SEQ ID NO 3) using Primer Express, a software exclusive for ABI PRISM Sequence Detector.

Total RNA was extracted from 7-week old C57BL/6NCrj mice (obtained from Charles River Laboratories, Japan, Inc.) tissues using a RNeasy Mini kit (QIAGEN, Co.) and treated with DNase according to the manual. DNase treatment was carried out using DNaseI (RNase free) (Roche Diagnostics, Co.) at 25° C. for 15 min. The total RNA of about 50 ng obtained was treated with TaqMan Reverse Transcription Reagents (Applied Biosystems, Co.) for reverse transcription at 25° C. for 10 min, at 48° C. for 60 min, and at 95° C. for 10 min to synthesize cDNA. The PCR reaction solution was mixed with 2.5 μL of 10×SYBR Green, 3.0 μL of 25 mM $MgCl_2$, 2.0 μL of dNTP mix, 0.125 μL of AmpliTaq Gold, and cDNA using SYBR Green PCR Core Reagents Kit and added with distilled water to adjust a volume to 25 μL. The reaction using ABI PRISM 7700 Sequence Detector was carried out at 50° C. for 2 min and at 95° C. for 10 min followed by repeating 40 cycles of reaction at 94° C. for 20 sec, at 58° C. for 20 sec and at 72° C. for 30 sec.

Figure 5:
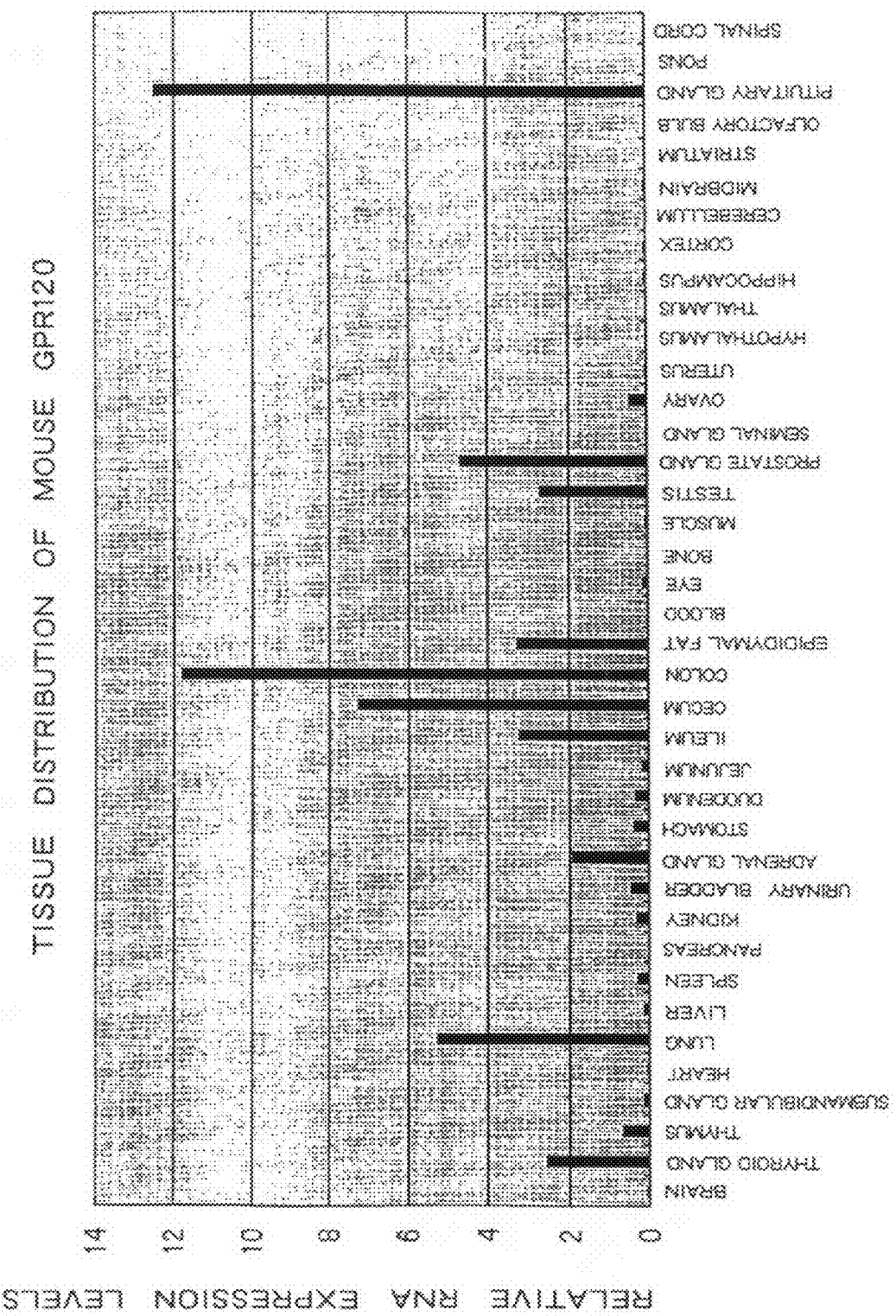
FIG. 5 shows the tissue expression pattern of GPR120 in mice.

The distribution pattern of mRNA expression in each tissue is shown in FIG. 5. As shown in FIG. 5, high levels of expression were detected in the pituitary gland, lung, intestinal tracts (particularly, ileum, cecum, and colon), testis, prostate gland, thyroid gland, and adrenal gland.

Example 9

Detection of Active Substances in Extracts of Mouse Intestinal Tracts and Testis which Elevate PLAP Activity Specifically in GPR120-SE302 Cells Based on the distribution pattern of GPR120 shown in Example 8, extracts of intestinal tracts and testis which showed high levels of GPR120 expression were used to search for substances showing GPR120 specific ligand activities by the method shown below.

Intestinal tracts of 18 g and testis of 20 g were excised from 6-week old C57BL/6CrSlc mice (Japan SLC, Inc.) and frozen immediately with dry ice and stored at −80° C. until use. The frozen organs were directly added to the homogenization buffer of 10 fold volume of the frozen organ weight (70% acetone, 1M acetic acid, 20 mM hydrochloric acid, chilled at 4° C.) and homogenized using a home fiber mixer MX-X103 (Matsushita Electronic Industrial Co., Ltd.). Following the 2-hour extraction on ice, extracts were transferred to 500 mL centrifuge tubes (Nalge Nunc International, Co.) and centrifuged at 10,000×g for min at 4° C. After centrifugation, supernatants were transferred to glass bottles with caps and an equal volume of diethylether was added. After shaking for 3 min, extracts were left to stand for 30 min at 4° C. to separate the upper ether layer containing lipids from the lower aqueous layer. The ether layer was removed using an aspirator and an equal volume of diethylether was added again to the remaining aqueous layer and the mixture was shaken well for 3 min. The mixture was left to stand for 30 min at 4° C. and the upper ether layer was removed using an aspirator again.

The aqueous layer obtained was transferred to 50 mL Oak Ridge centrifuge tubes (Nalge Nunc International, Co.) and centrifuged at 20,000×g for 30 min at 4° C. After centrifugation, intermediate aqueous layers were collected as an extract solution. The extract solution was filtered through a 100 μm nylon cell strainer (Becton Dickinson, Co.) and diluted to 2.5 fold with water and loaded onto a HF MEGA BOND ELUTE C18 column (10 g resin, 60 mL volume, Varian, Inc.). The column was washed with 80 mL of 0.1% trifluoroacetic acid (abbreviated as TFA hereinafter) and eluted with 40 mL of 50% acetonitrile comprising 0.1% TFA. Herein, an amount of the extract solution applied per column was kept at below a level so that the corresponding starting organ weight was 40 g or less and several columns were used and eluates were combined after elution if the amount of the extract solution exceeds the level.

The lyophilized powder of the extract solution was dissolved in 1 M acetic acid and filtered through a 0.22 μm Millex-GV PVDF filter (Millipore, Co.) and loaded onto a ODS column (YMC-Pack ODS-A, 4.6ϕ×300 mm, YMC, Inc.). Elution was carried out with a concentration gradient of 24-48% acetonitrile and fractions were collected every minute. Each fraction was lyophilized. These fractions were dissolved in 0.1% TFA and PLAP activity was measured according to the method descried in Example 7. As a result, a marked elevation of PLAP activity in GPR120-SE302 cells was observed in fractions eluted with about 34% acetonitrile. This elevation of PLAP activity was not observed in cells expressing other receptors indicating the presence of a GPR120 specific active substance in extracts of both intestinal tracts and testis from mouse.

Example 10

Detection of Active Substances n Extracts of Rat Intestinal Tracts and Testis which Elevate PLAP Activity Specifically in GPR120-SE302 Cells It was examined whether GPR120 specific ligand activities might be found also in rat testis and intestinal tracts as in the mouse.

About 300 g of testis and about 450 g of intestinal tracts from 100 of 9-week old Wistar rats (obtained from Japan SLC, Inc.) were excised and frozen with dry ice immediately. Using the method described in Example 9, extracts of intestinal tracts and testis were prepared. Lyophilized powder was dissolved in 1M acetic acid and filtered through a 0.22 μm Millex-GV PVDF filter (Millipore, Co.), and then, loaded onto a ODS column (YMC-Pack ODS-A, 4.6ϕ×300 mm, YMC, Inc.). Elution was carried out with a concentration gradient of 24-48% acetonitrile and fractions were collected every minute. Herein, for fractionation using a ODS column, an amount of sample per fractionation was kept at below a level so that the corresponding starting organ weight was 20 g or less and several fractionations were carried out and sample fractions were combined to one for further experiments. Each fraction was lyophilized to measure PLAP activity using the method described in Example 7.

As a result, similarly to the mouse extracts, GPR120-SE302 cell specific elevation of PLAP activity was detected. Thus, the presence of GPR120 specific active substance was shown also in rat extracts of intestinal tracts and testis. It was decided to use a rat with higher organ weight in the experiments thereafter.

Example 11

Purification and Amino Acid Sequence Determination of an Active Substance from Extracts of Rat Intestinal Tracts which Elevates PLAP Activity Specifically in GPR120-SE302 Cells Dried powder of active fractions from rat intestinal tracts extracts obtained in Example 10 was dissolved in 10 mM ammonium formate (pH was adjusted to 3 using phosphoric acid) containing 10% acetonitrile, and loaded onto a cation-exchange column (TSKgel SP-5PW, 7.5φ×75 mm, Tosoh, Co.). Elution was carried out using a concentration gradient of 10 mM-1.0M ammonium formate in the presence of 10% acetonitrile. The activity was recovered in fractions eluted with about 280 mM ammonium formate. Active fractions were loaded onto a Diphenyl column (Vydac219TP Diphenyl Reversed Phase, 4.6φ×250 mm, GRACE VYDAC) and eluted with a concentration gradient of 21%-48% acetonitrile containing 0.1% TFA. The activity was detected in fractions eluted with about 30% of acetonitrile.

Active fractions were diluted 3-fold with 0.1% TFA and loaded onto a ODS column (Vydac218TP C18 Reversed Phase, 4.6φ×250 mm, GRACE VYDAC) and eluted with a concentration gradient of 27%-42% acetonitrile containing 0.1% TFA. The activity was observed in fractions eluted with about 34% of acetonitrile.

Active fractions were diluted 3-fold with 0.1% TFA and loaded onto a μRPC C2/C18 column (4.6φ×100 mm, Amersham Biosciences, Co) and eluted with a concentration gradient of 24%-48% acetonitrile containing 0.1% TFA. Eluates were fractionated by a peak manually. The activity was observed in fractions eluted with about 35% acetonitrile.

Active fractions were diluted 3-fold with 0.1% heptafluorobutyric acid (abbreviated as HFBA hereinafter) and loaded onto a ODS column (YMC-Pack ProC18, 2.0φ×150 mm, YMC, Inc.). Elution was carried out with a concentration gradient of 24%-48% acetonitrile containing 0.1% HFBA and eluates were fractionated by a peak manually. The activity was obtained in fractions eluted with about 35% acetonitrile.

The active fraction was sent to the analytical service at Apro Science, Inc. for amino acid analysis and the amino acid sequence was determined by N-terminal amino acid analysis using Procise 494 cLC (Applied Biosystems, USA). As a result, the sequence of XLLELAGTLDXVGPRSP (SEQ ID NO 21) from N-terminal to the 17th residue was obtained. This sequence was 100% identical to the sequence from residue number 29 to 45 of a precursor form of rat Group X secretory phospholipase A2 (GX-sPLA2) (SEQ ID NO 22, Swiss-Prot accession number: Q9QZT3), namely, the sequence of rat GX-sPLA2 (SEQ ID NO 23) from N-terminal to the 17th residue, except for residue X which could not be determined. The first residue X of SEQ ID NO 21 was failed to get a part of the first cycle of chromatogram due to machine troubles. In addition, X at the 11th residue of SEQ ID NO 21 could not be identified as a corresponding amino acid quantitatively, however, this residue was predicted as cysteine based on the database sequence of Q9QZT3 (SEQ ID NO 22).

Example 12

Purification and Amino Acid Sequence Determination of an Active Substance from Rat Testis Extracts which Elevates PLAP Activity Specifically in GPR120-SE302 Cells Dried powder of active fractions from rat testis extracts obtained in Example 10 was dissolved in 10 mM ammonium formate (pH was adjusted to 3 using phosphoric acid) containing 10% acetonitrile, and loaded onto a cation-exchange column (TSKgel SP-5PW, 7.5φ×75 mm, Tosoh, Co.). Elution was carried out using a concentration gradient of 10 mM-1.0M ammonium formate in the presence of 10% acetonitrile. The activity was recovered in fractions eluted with about 280 mM ammonium formate. Active fractions were loaded onto a Diphenyl column (Vydac219TP Diphenyl Reversed Phase, 4.6φ×250 mm, GRACE VYDAC) and eluted with a concentration gradient of 21%-48% acetonitrile containing 0.1% TFA. The activity was detected in fractions eluted with about 30% acetonitrile.

Figure 6B:
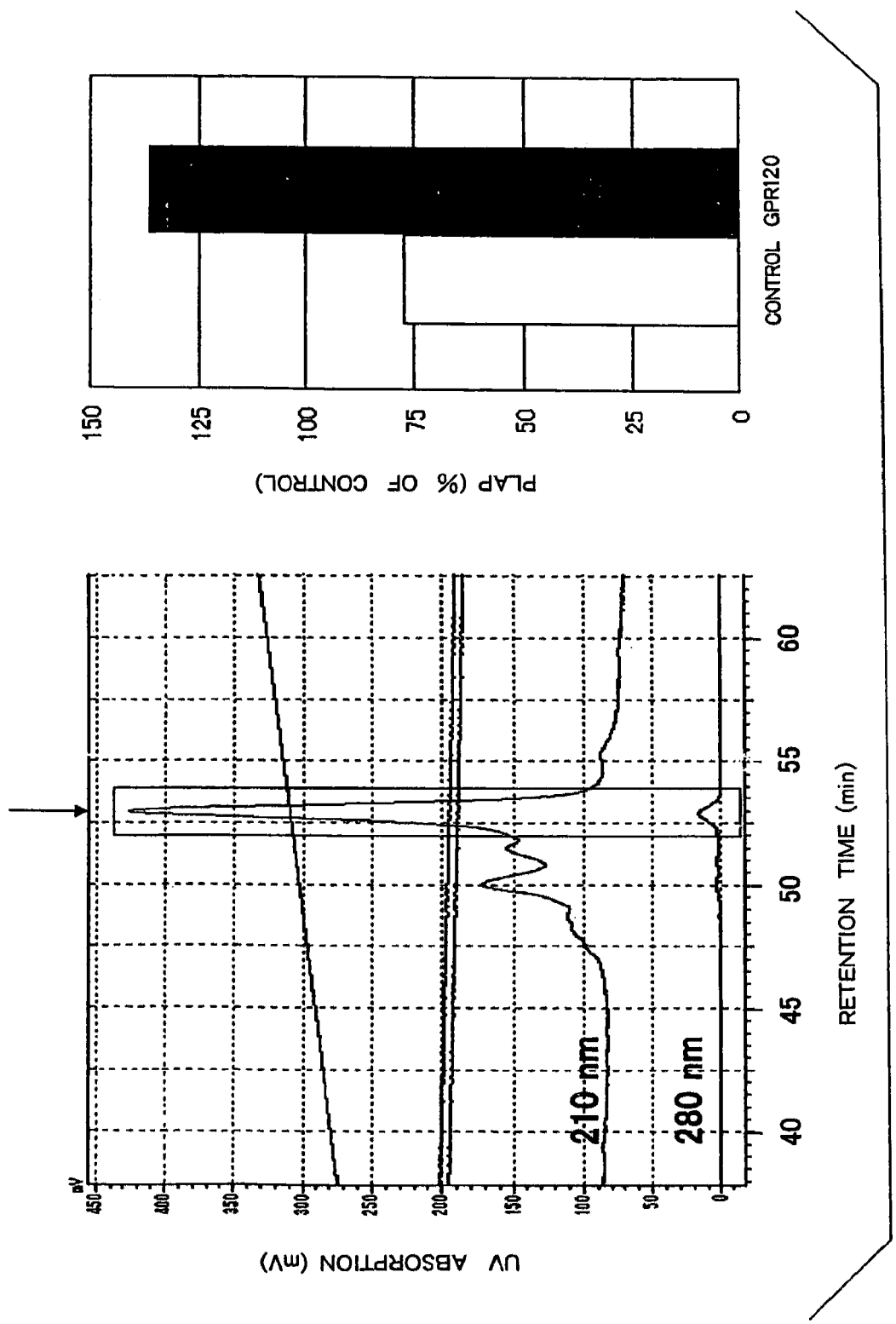
FIG. 6B shows a UV absorption pattern of finally purified rat testis extracts by HPLC using the SunFire C18 column, and GPR120 mediated PLAP activity in a peak fraction indicated with an arrow. Control cells and GPR120-SE302 cells were compared.

Active fractions were diluted 3-fold with 0.1% HFBA and loaded onto a ODS column (Vydac218TP C18 Reversed Phase, 4.6φ×250 mm, GRACE VYDAC) and eluted with a concentration gradient of 27%-51% acetonitrile containing 0.1% HFBA. The activity was observed in fractions eluted with about 44% acetonitrile (FIG. 6-A).

Active fractions were diluted 3-fold with 0.1% HFBA and loaded onto a ODS column (SunFire (trademark) C18 3.5 μm, 2.1φ×150 mm, Waters) and eluted with a concentration gradient of 28.8%-46.8% acetonitrile. Eluates were fractionated by a peak manually. The activity was obtained as a single peak eluted with about 36% acetonitrile (FIG. 6-B).

The active fraction was sent to the analytical service at Apro Science, Inc. for amino acid analysis and the amino acid sequence was determined by N-terminal amino acid analysis using Procise 494 cLC (Applied Biosystems, USA). As a result, the sequence of GLLELAGTLDXVGPR (SEQ ID NO 24) was obtained from N-terminal to the 15th residue. This sequence, except for the residue X which could not be determined, matched 100% with the sequence from residue number 29 to 43 of a precursor form of rat GX-sPLA2 (SEQ ID NO 22), namely rat GX-sPLA2 (SEQ ID NO 22) from N-terminal to 15th residue. The residue X of SEQ ID NO 24 could not be detected; however, this residue was predicted to be cysteine from the database sequence (SEQ ID NO 22).

Example 13

Cloning of Human and Mouse cDNA Encoding a Precursor form of GX-sPLA2

Cloning of cDNA encoding a precursor form of human and mouse homologue of GX-sPLA2 which were identified as an active substance in extracts of rat intestinal tracts and testis to elevate PLAP activity specifically in GPR120-SE302 cells was carried out by the following method.

(1) Cloning of cDNA Encoding a Precursor Form of Human GX-sPLA2 (hGX-sPLA2)

Isolation of a polynucleotide encoding a precursor form of hGX-sPLA2 was carried out by PCR using Human Lung QUICK-Clone cDNA (Clonetech, Co.) as a template, and a pair of primers, 5'-primer (5'-ATGGGGCCGCTACCTGT-GTGCCTGCC-3') (SEQ ID NO 26) and 3'-primer (5'-TCAGTCACACTTGGGCGAGTCCGGC-3') (SEQ ID NO 27), designed for the sequence from nucleotide number 441 to 938 of, the coding region of hGX-sPLA2 based on the nucleic acid sequence of SEQ ID NO 25 (GenBank accession number NM_003561). The reaction was carried out first at 94° C. for 5 min and followed by repeating 35 cycles of reaction at 94° C. for 1 min, at 61° C. for 1 min, and at 72° C. for 3 min and finally run at 72° C. for 7 min for elongation reaction using FastStart High Fidelity PCR System (Roche Diagnostics, Co.). The amplified PCR product of about 500 bp was inserted into pCR2.1 (Invitrogen, Co.) and hGX-sPLA2-pCR2.1 was obtained.

As a result of sequence confirmation using ABI prism DNA sequencing kit (Perkin-Elmer Applied Biosystems, Co.), the sequence of 498 base pairs inserted into pCR2.1 was identical to the sequence of the nucleotide from number 441 to 938 of SEQ ID NO 25.

(2) Cloning of cDNA Encoding Mouse GX-sPLA2 (mGX-sPLA2)

For the isolation of the polynucleotide encoding mGX-sPLA2, a pair of primers designed for the sequence from nucleotide number 175 to 630 of the coding region of mGX-sPLA2 based on the nucleic acid sequence of SEQ ID NO 28 (GenBank accession number NM_011987), which were 5'-primer (5'-ATGCTGCTGCTACTGCTGCTGTTGC-3') (SEQ ID NO 29) and 3'-primer (5'-TCAATTGCACTTGG-GAGAGTCCTTC-3') (SEQ ID NO 30). A template cDNA was prepared by reverse transcription of RNA of C57/BL/6NCrj mouse intestinal tracts shown in Example 8 using the same method as Example 8. The reaction was carried out first at 94° C. for 5 min and followed by repeating 35 cycles of reaction at 94° C. for 1 min, at 58° C. for 1 min, and at 72° C. for 3 min and finally run at 72° C. for 7 min for elongation reaction using FastStart High Fidelity PCR System (Roche Diagnostics, Co.). The amplified PCR product of about 450 bp was inserted into pCR2.1 (Invitrogen, Co.) and mGX-sPLA2-pCR2.1 was obtained. As a result of sequence confirmation using an ABI prism DNA sequencing kit (Perkin-Elmer Applied Biosystems, Co.), the sequence of 456 base pairs inserted into pCR2.1 was identical to the sequence of nucleotide from number 175 to 630 of SEQ ID NO 28.

Example 14

Preparation of the Retrovirus Vector for Introduction of a Gene for C-Terminal His Tagged GX-sPLA2 (GX-sPLA2-His6)

(1) Cloning of a Gene for C-Terminal His Tagged GX-sPLA2 (GX-sPLA2-His6)

For preparation of a gene for C-terminal His tagged GX-sPLA2 (hGX-sPLA2-His6), PCR was carried out using hGX-sPLA2-pCR2.1 as a template and a pair of primers, which were 5'-primer (5'-GATATCGCCGCCACCATGGGGC-CGCTACCTGTG-3') (SEQ ID NO 31) and 3'-primer (5'-GATATCTCAATGGTGATGGTGATGATG-GTCACACTTGGGCGAGTC-3') (SEQ ID NO 32). Similarly, C-terminal His tagged mouse GX-sPLA2 (mGX-sPLA2-His6) was prepared by PCR using a mGX-sPLA2-pCR2.1 obtained in Example 13 as a template and a pair of primers which were 5'-primer (5'-GATATCGCCGCCAC-CATGCTGCTGCTACTGCTG-3') (SEQ ID NO 33) and 3'-primer (5'-GATATCTCAATGGTGATGGTGATGAT-GATTGCACTTGGGAGAGTC-3') (SEQ ID NO 34). PCR was carried out using FastStart High Fidelity PCR System (Roche Diagnostics Co.) at 94° C. for 5 min first and followed by repeating 15 cycles of reaction at 94° C. for 1 min, at 61° C. for 1 min (for hGX-sPLA2) or at 58° C. for 1 min (for mGX-sPLA2), and at 72° C. for 3 min, and finally at 72° C. for 7 min for elongation reaction. The PCR product obtained was inserted again into pCR2.1 (Invitrogen, Co.) and hGX-sPLA2-His6-pCR2.1 and mGX-sPLA2-His6-pCR2.1 were obtained.

(2) Preparation of Retrovirus Vectors for hGX-sPLA2-His6 and mGX-sPLA2-His6 hGX-sPLA2-His6-pCR2.1 and mGX-sPLA2-His6-pCR2.1 were cleaved with EcoRV to obtain hGX-sPLA2-His6 and mGX-sPLA2-His6, respectively. These were subcloned into pBabeCLXIH (described in Example 2) which was cleaved with a restriction enzyme, HpaI, and retrovirus vector plasmids pBabe(mGX-sPLA2-His6)IH and pBabe(hGX-sPLA2-His6)IH were obtained for introduction of GX-sPLA2-His6 gene. These were used to prepare retrovirus vector solutions using the same method as Example 4.

Example 15

Preparation of CHO-K1 Cells Expressing GX-sPLA2-His6

$1.2 \times 10^5$ CHO-K1 cells were cultured in a 6-well plate (Japan Becton Dickinson, Co.) with 2 mL of DMEM medium (containing 10% FBS, penicillin 100 units/mL, and streptomycin 100 μg/mL). On the following day, culture media were removed and 4 mL of the retrovirus vector solution prepared in Example 14 and 20 μL of 1.6 mg/mL polybrene (a final concentration of 8 μg/mL) were added. Subsequently, cells were cultured with the medium containing 350 μg/mL of hygromycin and surviving cells were used for the following experiments as CHO-K1 cells expressing human or mouse His-tagged. GX-sPLA2 (hGX-sPLA2-His6-CHO-K1 cells and mGX-sPLA2-His6-CHO-K1 cells, respectively).

Example 16

Preparation of HEK Cells Expressing GX-sPLA2-His6

$1.2 \times 10^5$ HEK cells were cultured in a collagen coated 6-well plate (Asahi Technoglass, Co.) with 2 mL of DMEM medium (containing 10% FBS, penicillin 100 units/mL and streptomycin 100 μg/mL). On the following day, culture media were removed and 4 mL of the retrovirus vector solution prepared in Example 14 and 20 μL of 1.6 mg/mL polybrene (a final concentration of 8 μg/mL) were added. Subsequently, cells were cultured with the medium containing 350 μg/mL of hygromycin and surviving cells were used for the following experiments as HEK cells expressing human or mouse His-tagged GX-sPLA2 (hGX-sPLA2-His6-HEK cells and mGX-sPLA2-His6-HEK cells, respectively).

Example 17

Measurement of PLAP Activity in GPR120-SE302 Cells Using Culture Media of Human and Mouse GX-sPLA2-His6-CHO-K1 Cells hGX-sPLA2-His6-CHO-K1 cells and mGX-sPLA2-His6-CHO-K1 cells were cultured with 10 mL of DMEM medium (containing 10% FBS, penicillin 100 units/mL and streptomycin 100 μg/mL) in a petri dish with a diameter of 10 cm (Becton Dickinson, Co.). Cells were cultured 2 more days after reaching confluence and culture media were recovered and PLAP activity in GPR120-SE302 cells was measured according to the method described in Example 7. As shown in FIG. 7, the presence of an active substance which elevates PLAP activity in GPR120-SE302 cells indicated in culture media from both cells.

Example 18

Figure 8:
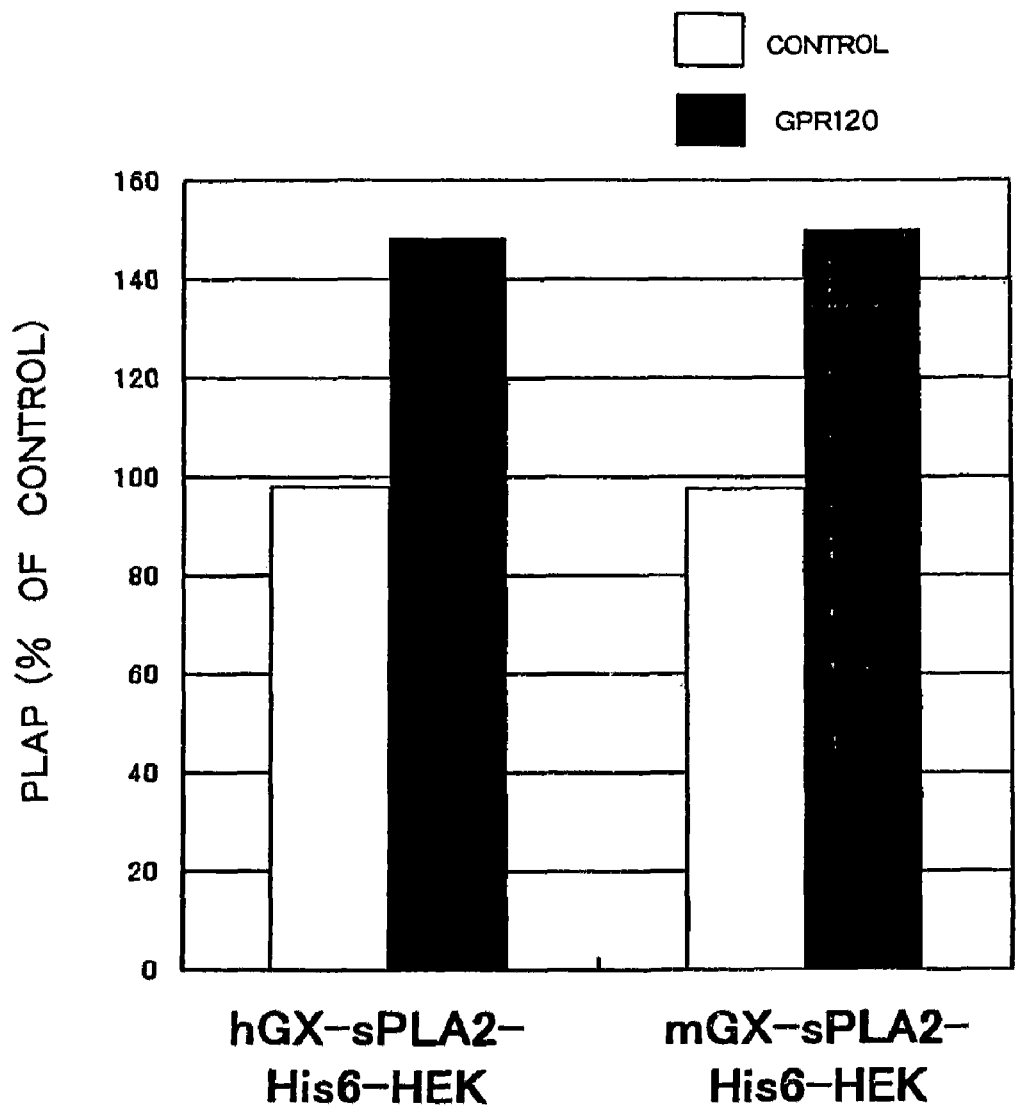
FIG. 8 shows the result of PLAP activities in GPR120-SE302 cells and control cells using the cultured media of GX-sPLA2-His6-HEK cells.

Measurement of PLAP Activity in GPR120-SE302 Cells Using Culture Media of Human and Mouse GX-sPLA2-His6-HEK Cells hGX-sPLA2-His6-HEK cells and mGX-sPLA2-His6-HEK cells were cultured with 10 mL of DMEM medium (containing 10% FBS, penicillin 100 units/mL and streptomycin 100 μg/mL) in a collagen coated petri dish with a diameter of 10 cm (Asahi Technoglass, Co.). Cells were cultured 2 more days after reaching confluence and culture media were recovered and PLAP activity in GPR120-SE302 cells was measured according to the method described in Example 7. As shown in FIG. 8, the presence of an active substance which elevates PLAP activity in GPR120-SE302 cells was indicated in culture media of both cells.

Example 19

Preparation of Baculovirus for Introduction of a Gene for C-Terminal His-Tagged GX-sPLA2

Baculovirus for introduction of a gene for C-terminal His-tagged GX-sPLA2 was prepared using BAC-TO-BAC Baculovirus Expression Systems (Invitrogen, Co.) according to the manual included in the kit. Specifically, hGX-sPLA2-His6-pCR2.1 and mGX-sPLA2-His6-pCR2.1 obtained in Example 14 were cleaved with restriction enzymes, XbaI and HindIII, and inserted into pFASTBAC1 plasmid cleaved with XbaI and HindIII to prepare hGX-sPLA2-His6-pFASTBAC and mGX-sPLA2-His6-pFASTBAC, respectively. Bacmid DNA was recovered by transposition of these plasmids in DH10BAC competent cells provided with the kit. Sf9 cells cultured with SF900II SFM (Invitrogen, Co.) were transfected with bacmid DNA using Cellfectin (Invitrogen, Co.) and the culture supernatant were recovered 3 days later and baculovirus for introduction of a gene for human or mouse C-terminal His-tagged GX-sPLA2.

Example 20

Purification of C-Terminal His-Tagged GX-sPLA2

The baculovirus for introduction of a gene for human or mouse C-terminal His-tagged GX-sPLA2 obtained in Example 19 was infected to Sf9 cells, respectively, and cultured in a flask with shaking. After 60 hours, the culture media were centrifuged and culture supernatants were obtained. Imidazol (Sigma, Co.) was added to the culture supernatants at a final concentration of 10 mM and loaded onto a Ni Sepharose 6 Fast Flow column (Amersham Biosciences, Co.). The column was washed with a 5 fold column volume of Binding Buffer (10 mM imidazol, 500 mM NaCl, 20 mM $NH_2PO_4$, pH 7.4) and eluted with Elution Buffer (500 mM imidazol, 500 mM NaCl, 20 mM $NaH_2PO_4$, 50 mM Tris-HCl, pH 7.4). Eluates were diluted 5-fold with 0.1% TFA and loaded onto a HF MEGA BOND ELUTE C18 column (Varian, Inc.). The column was eluted with 50% acetonitrile containing 0.1% TFA and eluates were lyophilized to obtain purified human and mouse C-terminal His-tagged GX-sPLA2 (hGX-sPLA2-His and mGX-sPLA2-His, respectively).

Example 21

Measurement of PLAP Activity in GPR120-302 Cells Using C-Terminal His-Tagged Mouse GX-sPLA2

Figure 9A:
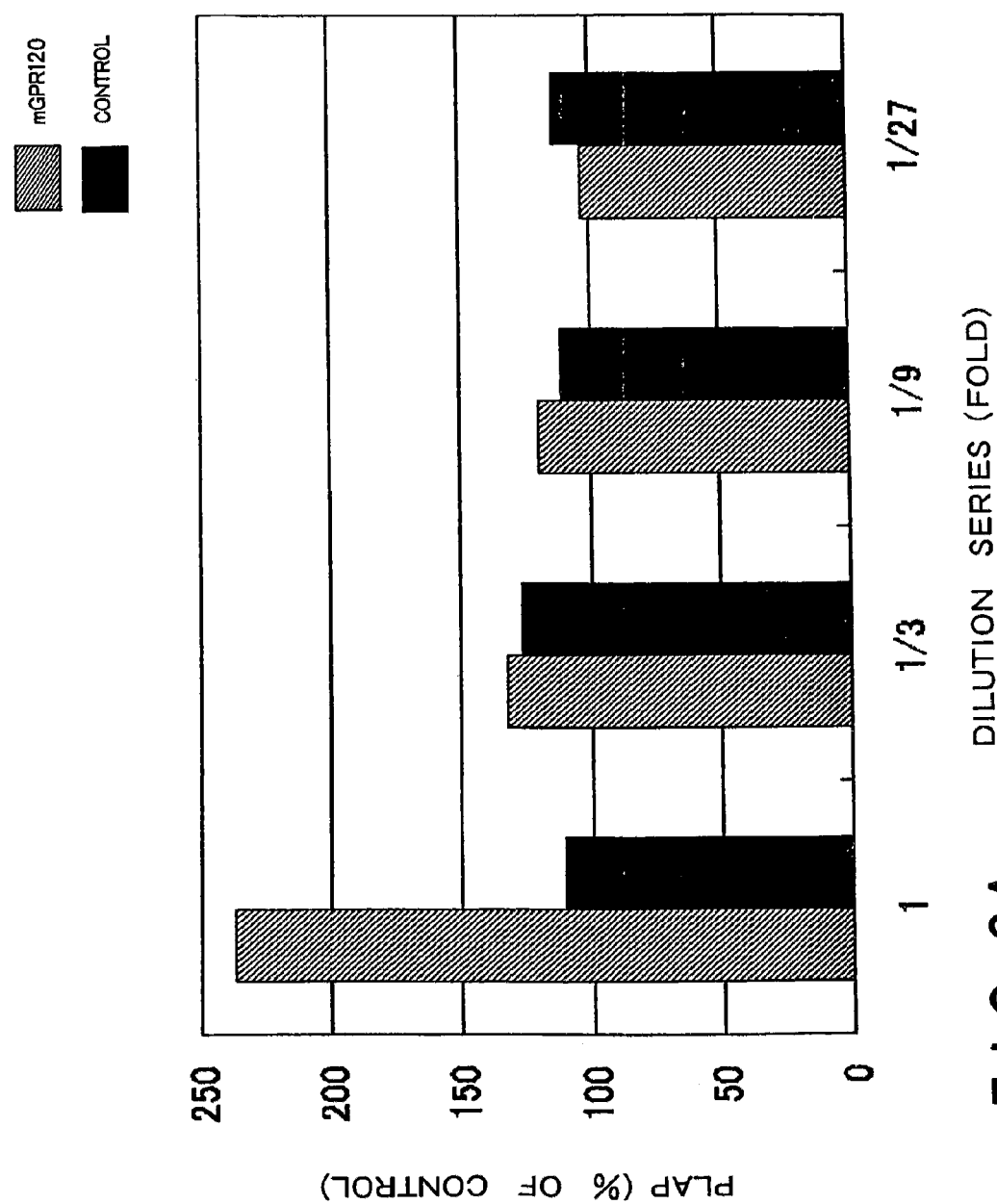
FIG. 9A shows PLAP activities in mGPR120-SE302 cells and control cells using C-terminal His tagged GX-sPLA2 purified by nickel-column. This
Figure 9B:
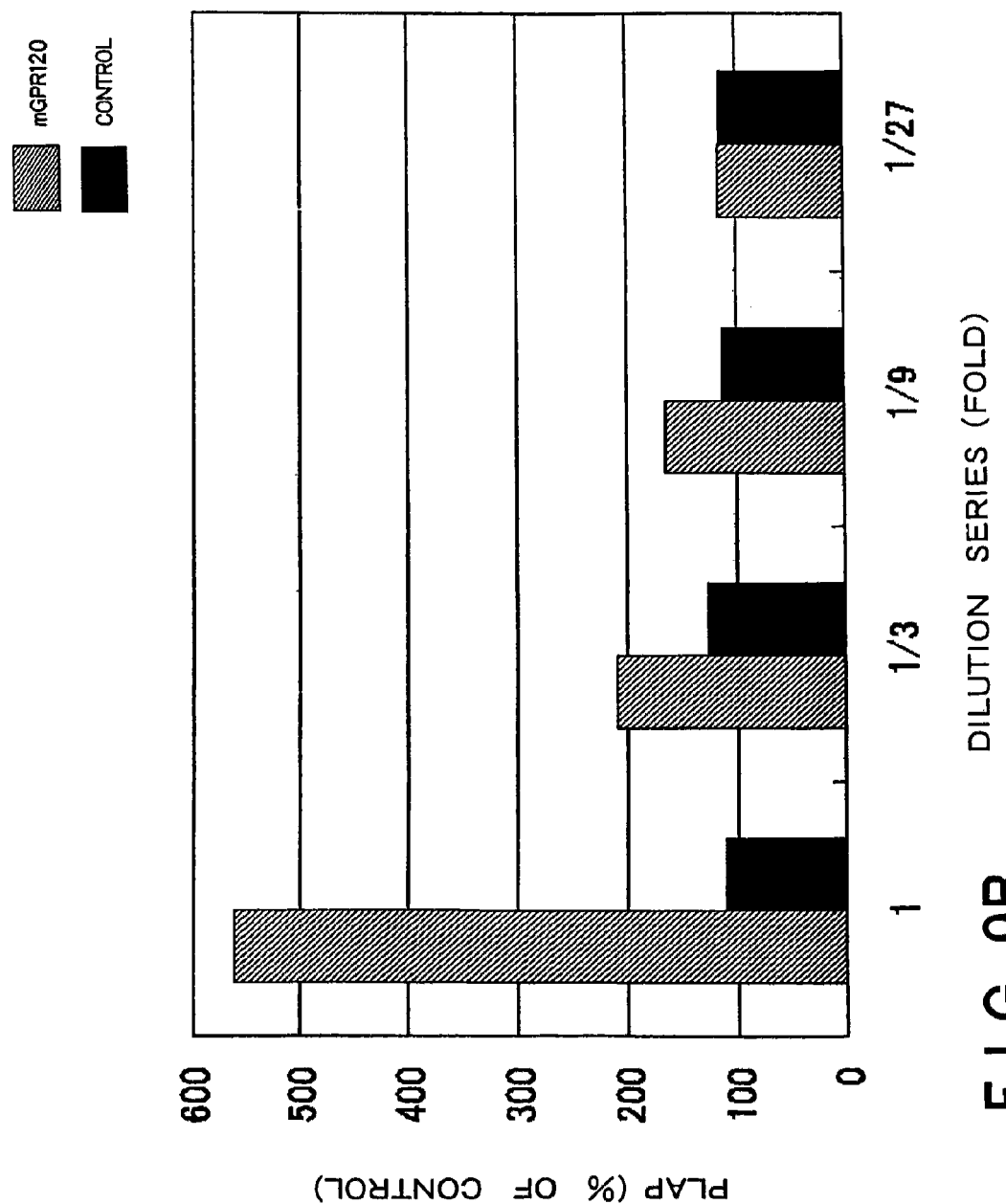
FIG. 9B shows PLAP activities in mGPR120-SE302 cells and control cells using C-terminal His tagged GX-sPLA2 purified by nickel column. This

The lyophilized powder of hGX-sPLA2-His and mGX-sPLA2-His obtained in Example 20 was dissolved in an appropriate amount of 0.1% TFA solution. Using these, PLAP activity in mGPR120-SE302 cells was measured according to the method described in Example 7. As shown in FIG. 9, a concentration dependent elevation of PLAP activity in mGPR120-SE302 cells of hGX-sPLA2-His (FIG. 9-A) and mGX-sPLA2-His (FIG. 9-B) was observed, indicating that GPR120 could be activated also by recombinant GX-sPLA2.

Example 22

Measurement of PLAP Activity in GPR120-SE302 Cells Using a Commercially-Available Porcine Pancreatic sPLA2

Figure 10A:
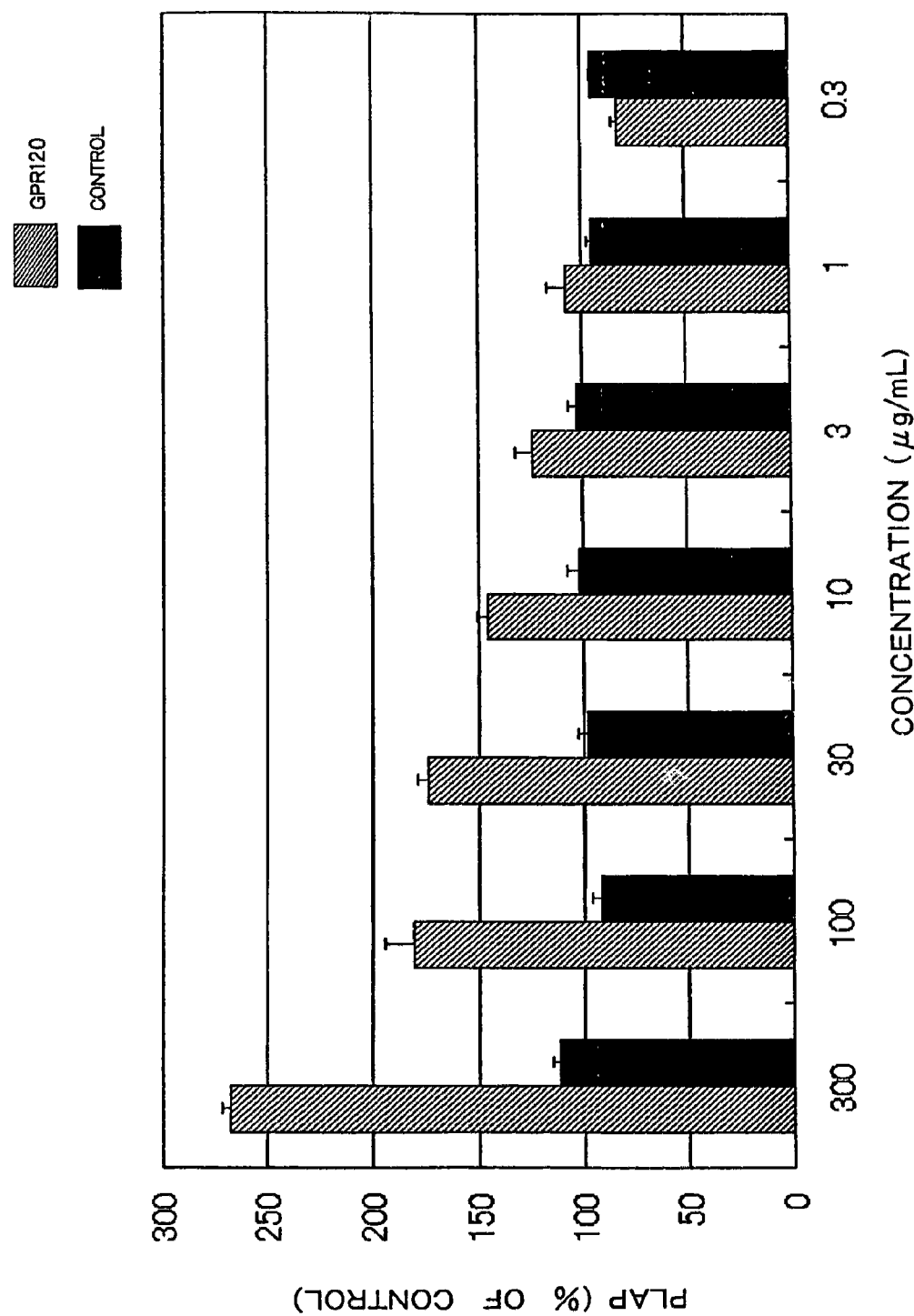
FIG. 10A shows the result of PLAP activities in GPR120-SE302 cells using commercially-available porcine pancreatic sPLA2 compared to control cells.

A porcine pancreatic sPLA2 (Phospholipase A2 from porcine pancreas (ammonium sulfate suspension (using soybean L-α-phosphatidylcholine) 600 units/mg protein, pH 8.0, 37° C., Sigma Co.) was centrifuged and the pellet was dissolved in water. PLAP activity was measured according to the method described in Example 7. As shown in FIG. 10, a concentration dependent elevation of PLAP activity in GPR120-SE302 cells (FIG. 10-A) and mGPR120-SE302 cells (FIG. 10-B) was detected. This porcine pancreatic sPLA2 is reported to be mainly Group IB sPLA2 (GIB-sPLA2) (Swiss Prot accession number P00592) (Ta-min Chang et al., J. Biol. Chem. 274 (16): 10758-10764, 1999), thus, it was shown that GPR120 could be activated by not only GX-sPLA2 but also GIB-sPLA2.

Example 23

Measurement of PLAP Activity in GPR120-SE302 Cells Using a Commercially-Available Honey Bee Venom PLA2

Figure 11A:
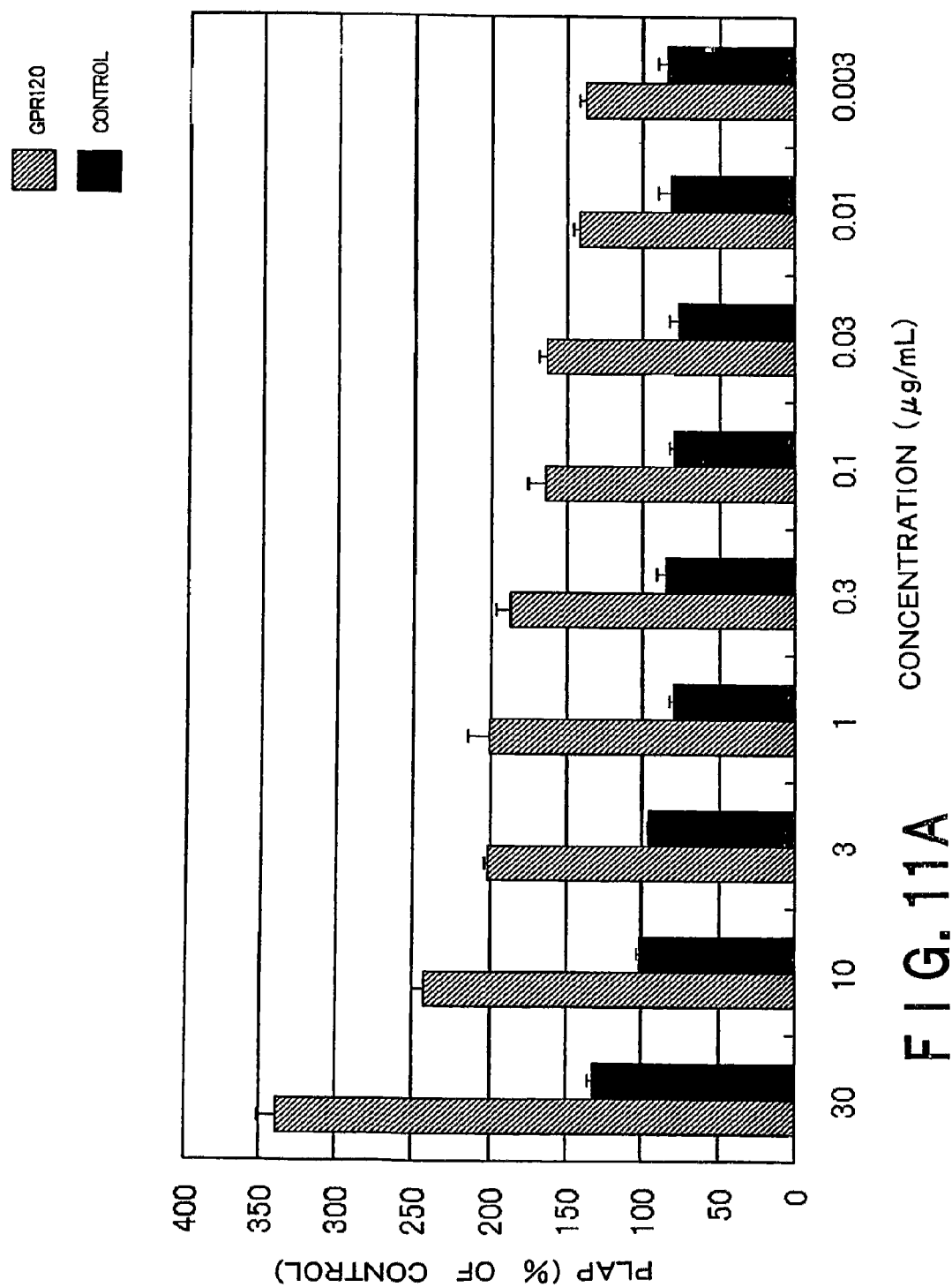
FIG. 11A shows the result of PLAP activities in GPR120-SE302 cells using commercially-available honey bee venom PLA2 compared to control cells.
Figure 11B:
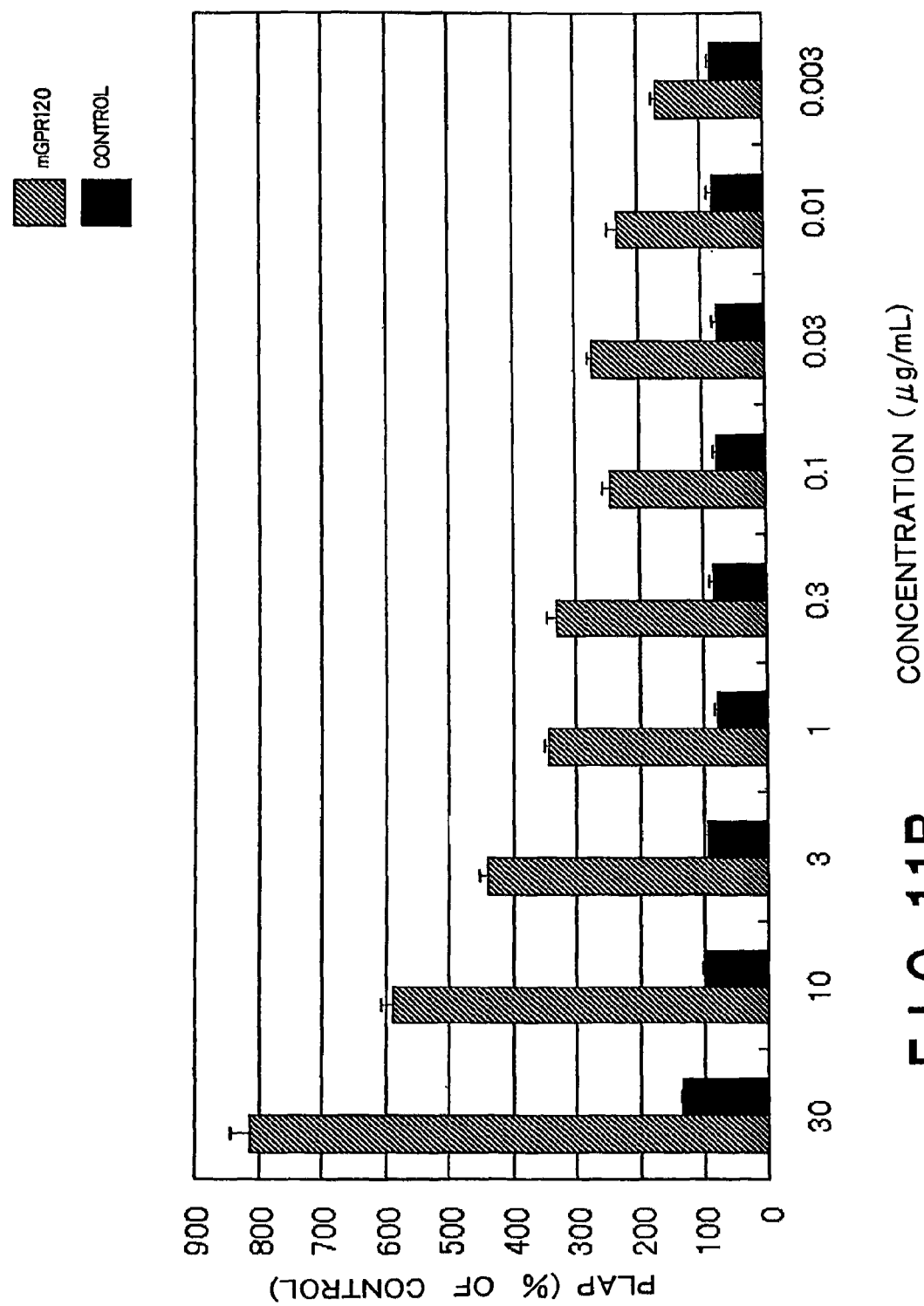
FIG. 11B shows the result of PLAP activities in mGPR120-SE302 cells using commercially-available honey bee venom PLA2 compared to control cells.

A honey bee venom PLA2 (bvPLA2) (Phospholipase A2 from honey bee venom (salt free, lyophilized powder 600-1800 units/mg protein, Sigma Co.) was dissolved in water and PLAP activity was measured in GPR120-SE302 cells and mGPR120-SE302 cells according to the method described in Example 7. As shown in FIG. 11, in GPR120-SE302 cells (FIG. 11-A) and mGPR12-SE302 cells (FIG. 11-B), a concentration dependent elevation of PLAP activity was detected. From these results, it was shown that not only secretary PLA2 such as GX-sPLA2 and GIB-sPLA2 but also honey bee venom PLA2 could activate GPR120.

Example 24

Measurement of PLAP Activity in GPR120-SE302 Cells Using a Commercially-Available Snake Venom PLA2

Figure 12A:
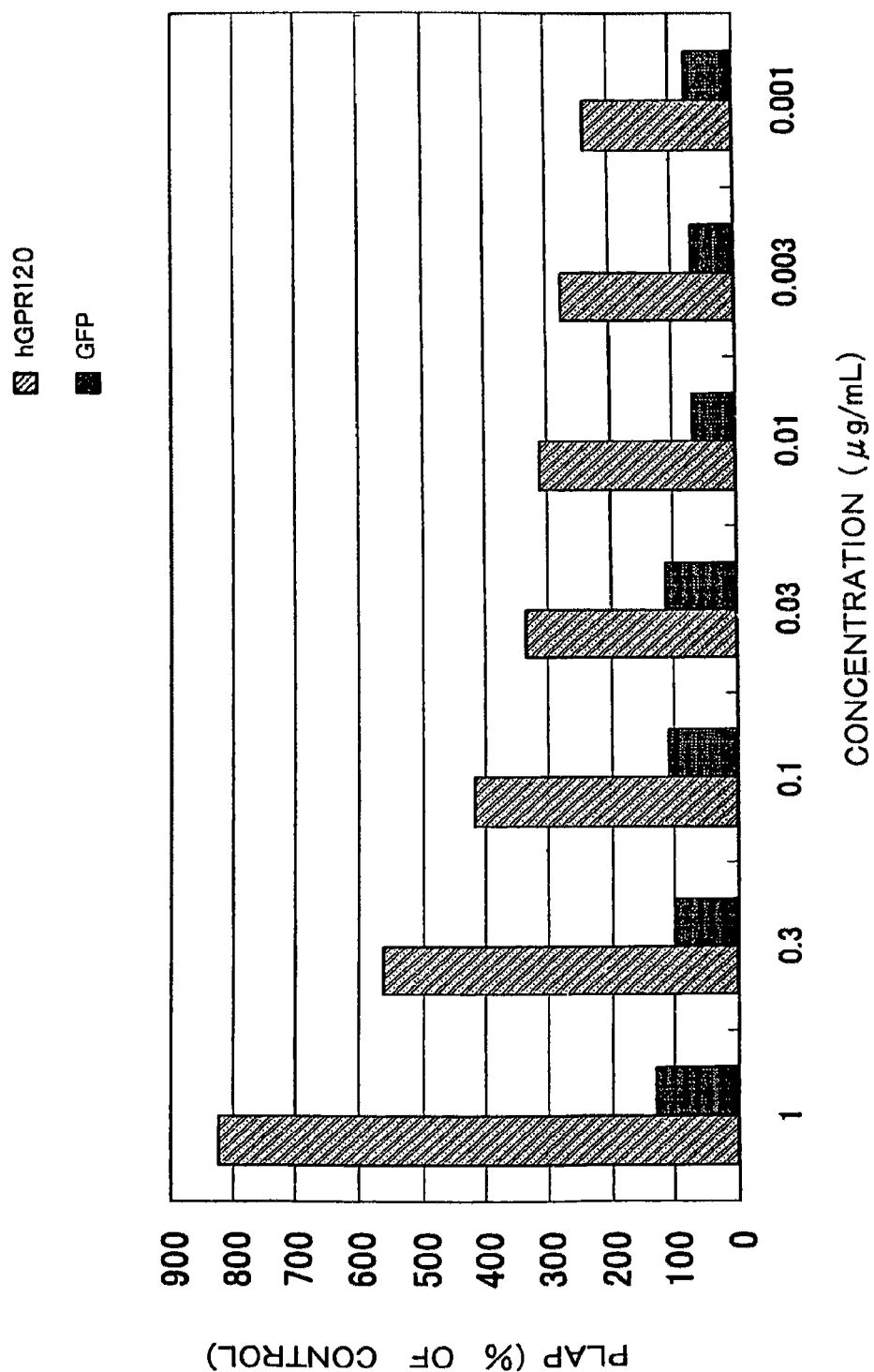
FIG. 12A shows the result of PLAP activities in GPR120-SE302 cells using commercially-available snake venom derived PLA2 compared to control cells.
Figure 12B:
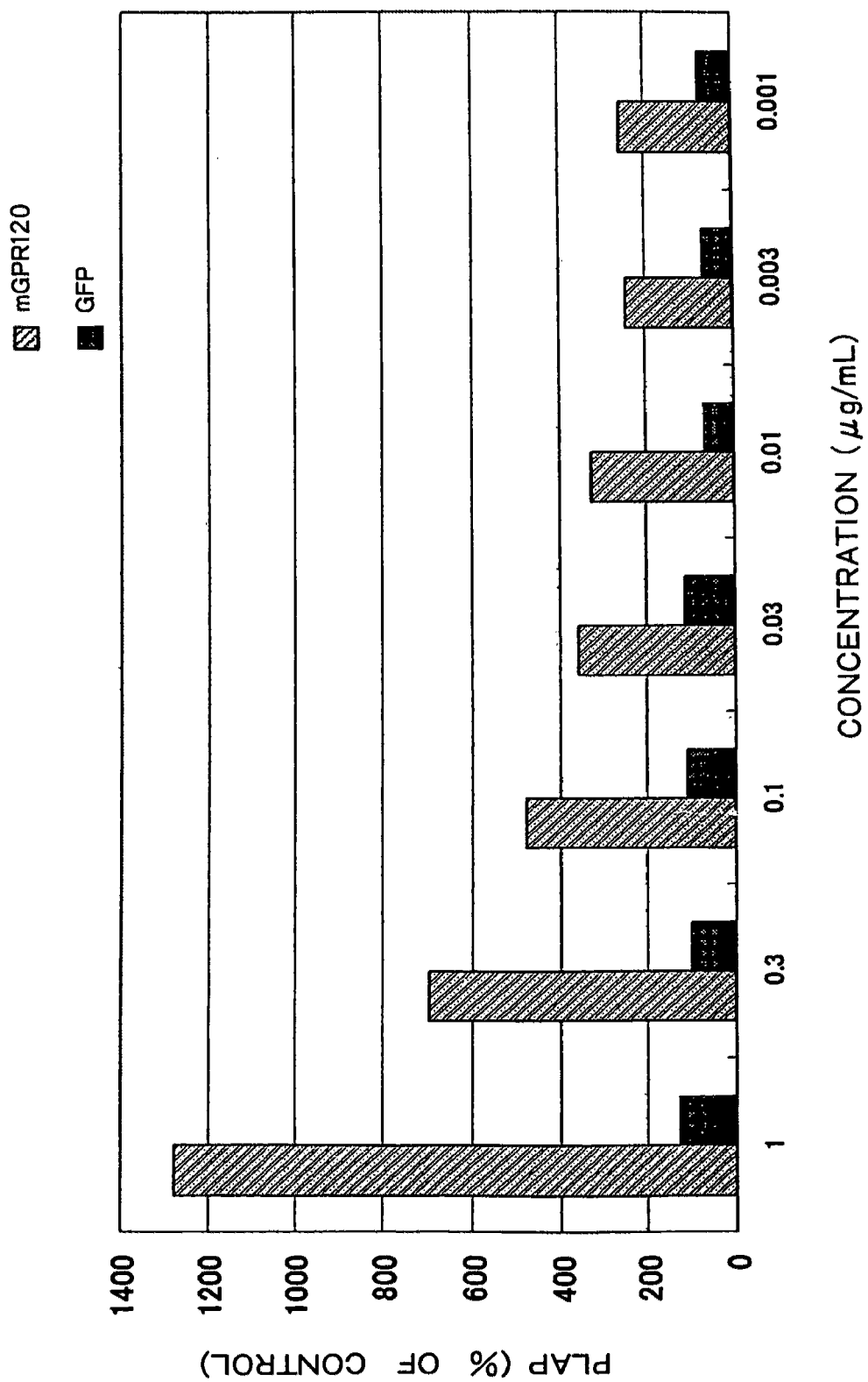
FIG. 12B shows the result of PLAP activities in mGPR120-SE302 cells using commercially-available snake venom derived PLA2 compared to control cells.

A snake venom PLA2 (Phospholipase A2 from Naja mossambica, Sigma, Co.) was dissolved in water and PLAP activity was measured in GPR120-SE302 cells and mGPR120-SE302 cells according to the method described in Example 7. As shown in FIG. 12, in GPR120-SE302 cells (FIG. 12A) and mGPR120-SE302 cells (FIG. 12B), a concentration dependent elevation of PLAP activity was detected. From these results, it was shown that snake venom PLA2 could also activate GPR120.

Example 25

Cloning of a cDNA Encoding C-Terminal FLAG Tagged GX-sPLA2

Using hGX-sPLA2-pCR2.1 obtained in Example 13 as a template and a pair of primers, which were a 5'-primer listed as SEQ ID NO 31 and a 3'-primer (5'-GATATCTCACTTGT- CATCGTCGTCCTTGTAGTCGTCACACTTGGGCGA-3') (SEQ ID NO 42), C-terminal FLAG-tagged human GX-sPLA2 (hGX-sPLA2-FLAG) (SEQ ID NO 43) was obtained by PCR. Similarly, C-terminal FLAG-tagged mouse GX-sPLA2 (mGX-sPLA2-FLAG) was obtained (SEQ ID NO 45) by PCR using mGX-sPLA2-pCR2.1 obtained in Example 13 as a template and a pair of primers which were a 5'-primer listed as SEQ ID NO 33 and a 3'-primer (5'-GATATCTCACTTGTCATCGTCGTCCTTG-TAGTCATTGCACTTGGGAGA-3') (SEQ ID NO 44). The PCR product obtained was inserted into pCR2.1 (Invitrogen, Co.) again and hGX-sPLA2-FLAG-pCR2.1 and mGX-sPLA2-FLAG-pCR2.1 were obtained, respectively.

Example 26

Figure 13B:
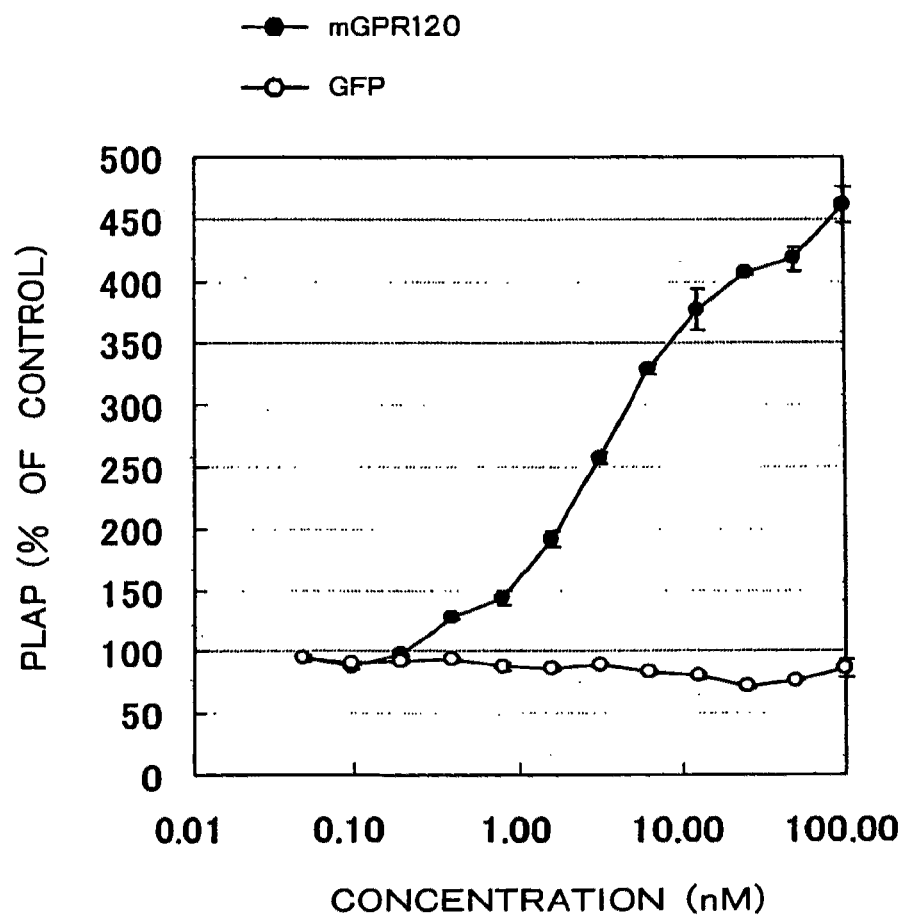
FIG. 13B shows the result of PLAP activities in mGPR120-SE302 cells using C-terminal FLAG tagged recombinant hGX-sPLA2 compared to control cells.

Measurement of PLAP Activity in GPR120-SE302 Cells Using C-Terminal FLAG-Tagged Recombinant hGX-sPLA2 hGX-sPLA2-FLAG-pCR2.1 obtained in Example 25 was digested with a restriction enzyme, EcoRV, and the fragment cleaved out was subcloned into pYNG vector (Katakura Industries, Co.) at EcoRV site. Extracted solution of silkworm pupae was obtained by ordering a protein production service (Superworm® system) (Katakura Industries, Co.). Extracted solution of silkworm pupae was loaded onto an ANTI-FLAG® M2 Agarose (Sigma Co.) and purification was carried out according to the manual provided with the column. Enzyme activity of sPLA2 was measured using sPLA2 Assay Kit (Cayman Chemical, Co.) according to the manual provided with the kit. Active fractions were loaded onto a VYDAC™ Protein & Peptide C18 column (#218TP54, VYDAC, Co.) and eluted with a concentration gradient of 24-42% of acetonitrile containing 0.1% TFA. Among peaks obtained, a single peak with the highest specific activity of sPLA2 was used for a PLAP assay as recombinant hGX-sPLA2. In addition, protein concentration of the recombinant protein was measured using Dc protein assay (BioRad, Co.). Recombinant hGX-sPLA2 obtained was dissolved in 0.1% TFA and PLAP activity was measured in GPR120-SE302 cells and mGPR120-SE302 cells according to the method described in Example 7. As shown in FIG. 13, a concentration dependent elevation of PLAP activity in GRP120-SE302 cells (FIG. 13A) and mGPR120-SE302 cells (FIG. 13B) was detected. From these results, it was shown that C-terminal FLAG-tagged recombinant hGX-sPLA2 could also activate GPR120.

Example 27

Measurement of PLAP Activity in GPR120-SE302 Cells Using Recombinant C-Terminal FLAG-Tagged mGX-sPLA2 mGX-sPLA2-FLAG-pCR2.1 obtained in Example 25 was digested with restriction enzymes, BamHI and XbaI, and fragments cleaved out were subcloned into pFastBac (Invitrogen, Co.) at BamHI and XbaI sites to obtain mGX-sPLA2-FLAG-pFAST Bac. Baculovirus was obtained using Bac-to-Bac™ Baculovirus Expression System (Invitrogen, Co.) and was infected to Sf-9 insect cells. Sf-9 cells were cultured with SF-900II medium (Invitrogen, Co.) (including penicillin/streptomycin and 2.5% FBS). The culture supernatant of baculovirus infected Sf-9 cells was loaded onto an ANTI FLAGR® M2 Agarose (Sigma, Co.) and the purification was carried out according to the manual provided with the column. Enzyme activity of sPLA2 was measured using sPLA2 Assay Kit (Cayman Chemical, Co.) according to the manual provided with the kit. Active fractions were loaded onto a VYDAC™ Protein & Peptide C18 column (#218TP54, VYDAC, Co.) and eluted with a concentration gradient of 24-54% of acetonitrile containing 0.1% TFA. Among peaks obtained, a single peak with the highest sPLA2 enzymatic activity was used for a PLAP assay as recombinant mGX-sPLA2. In addition, protein concentration of the recombinant was measured using Dc protein assay (BioRad, Co.). Recombinant mGX-sPLA2 obtained was dissolved in 0.05% TFA and 1% BSA (Fatty Acid Free, Sigma, Co.) and PLAP activity was measured in GPR120-SE302 cells and mGPR120-SE302 cells according to the method described in Example 7. As shown in FIG. 14, a concentration dependent elevation of PLAP activity in GRP120-SE302 cells (FIG. 14A) and mGPR120-SE302 cells (FIG. 14B) was detected. From these results, it was shown that C-terminal FLAG-tagged mGX-sPLA2 could also activate GPR120.

Example 28

Quantitation of GPR120 Gene Expression in Lung and Alveolar Macrophages Using the SYBR Green PCR Method 8-week old male C57BL/6NCrj mice (Charles River Laboratories, Japan, Inc.) or 8-week old male BALB/cAnNcrlcrlj mice (Charles River Laboratories, Japan, Inc.) were anesthetized with Nembutal and a catheter was inserted through airway. Broncho-Alveolar Lavage (BAL) was performed 4 times with 0.8 mL of PBS (−) (Phosphate Buffered Saline, Sigma, Co., 4° C.). 500 µL of bronco-alveolar lavage fluid (BALF) obtained was centrifuged at 350 rpm, for 5 min using a cytospin (Thermoelectron, Co.) and cells were collected and stained using DifQuick reagents (International Reagents, Co., Ltd.). As shown in FIG. 15A, most of cells in broncho-alveolar lavage fluid were confirmed to be alveolar macrophages. The rest of BALF was centrifuged at 450×g for 10 min to collect cells and total RNA was obtained using RNeasy Mini Kit (QIAGEN, Co.) according to the method described in Example 8. In addition, total RNA was also obtained from lung tissues. According to the method described in Example 8, cDNA was synthesized by reverse transcription. Then an amount of mouse GPR120 mRNA was measured using a pair of primers, a 5'-primer of SEQ ID NO 19 and a 3'-primer of SEQ ID NO 20, and a SYBR Green PCR Core Reagents Kit according to the method described in Example 8. As shown in FIG. 15, a similar expression level of mouse GPR120 mRNA was confirmed in the lung and alveolar macrophages from both C57BL/6 (FIG. 15B) and BALB/c (FIG. 15C).

Moreover, 8-week old Sprague-Dawley rats (Japan SLC, Inc.) were anesthetized with Nembutal and a catheter was inserted through airway and Broncho-Alveolar Lavage was performed 5 times with 5 mL PBS (−). Cells were collected by centrifugation at 450×g for 10 min and total RNA was recovered using RNeasy Mini Kit (QIAGEN, Co.). In addition, similarly, total RNA was recovered from lung. According to the method described in example 8, cDNA was synthesized by reverse transcription. Then, using a 5'-primer (5'-TGATC-CAGAACTTCCGGCA-3') (SEQ ID NO 46) and a 3'-primer (5'-CGGAGTTGGCAAACGTGAA-3') (SEQ ID NO 47) and a SYBR Green PCR Core Reagents Kit, 2.5 µL of 10×SYBR Green, 3.0 µL of 25 mM $MgCl_2$, 2.0 µL of dNTP mix, 0.125 µL of AmpliTaq Gold, 0.5 µL of 10 µM 5'-primer, 0.5 µL of 10 µM 3'-primer and cDNA were mixed and distilled water was added to make a total volume of 25 µL.

Moreover, primers of SEQ ID NOs 46 and 47 were designed based on the sequence of rat GPR120 using a software, Primer Express of ABI PRISM Sequence Detector. The reaction in ABI PRISM 7700 Sequence Detector was carried out at 50° C. for 2 min and at 95° C. for 10 min followed by repeating 40 cycles of reaction at 94° C. for 20 sec, at 58° C. for 20 sec, and at 72° C. for 30 sec. As shown in FIG. 15D, a similar expression level of rat GPR120 mRNA was also observed in the lung and alveolar macrophages from rats.

Example 29

Quantitation of GPR120 Gene Expression in Various Types of Macrophages Using the SYBR Green PCR Method 8-week old male C57BL/6NCrj mice were used (Charles River Laboratories, Japan, Inc.). Alveolar macrophages were collected according to the method described in Example 28. Peritoneal macrophages were collected by washing peritoneal cavity twice with 2.5 mL of PBS (−). In addition, peritoneal macrophages from the thioglycolate treated group were collected by injecting 2 mL of 3% thioglycolate (Sigma, Co.) intraperitoneally, and washing peritoneal cavity twice with 2.5 mL of PBS (−) 4 days later. Bone marrow was collected from femur. Bone marrow derived macrophages were obtained by treating bone marrow with BD Pharm Lyse™ Lysing Buffer (Becton Dickinson, Co.) for 5 min to lyse red blood cells and by suspending in RPMI 1640 medium (10% FBS, penicillin/streptomycin, 50 μM mercaptoethanol) and recombinant mouse M-CSF (R & D Systems, Co.) at a final concentration of 50 ng/mL and culturing in a 75 cm² flask for 5 days. Total RNA from each sample was prepared using TRIzol Reagent (Invitrogen, Co.) according to the manual. Total RNA obtained was DNase treated using DNA-free™ (Ambion Co.) according to the manual. According to the method described in Example 8, cDNA was synthesized by reverse transcription and levels of mouse GPR120 mRNA were measured using a 5′-primer of SEQ ID NO 19 and a 3′-primer of SEQ ID NO 20 according to the method described in Example 8 with a SYBR Green PCR Core Reagents Kit.

Figure 16:
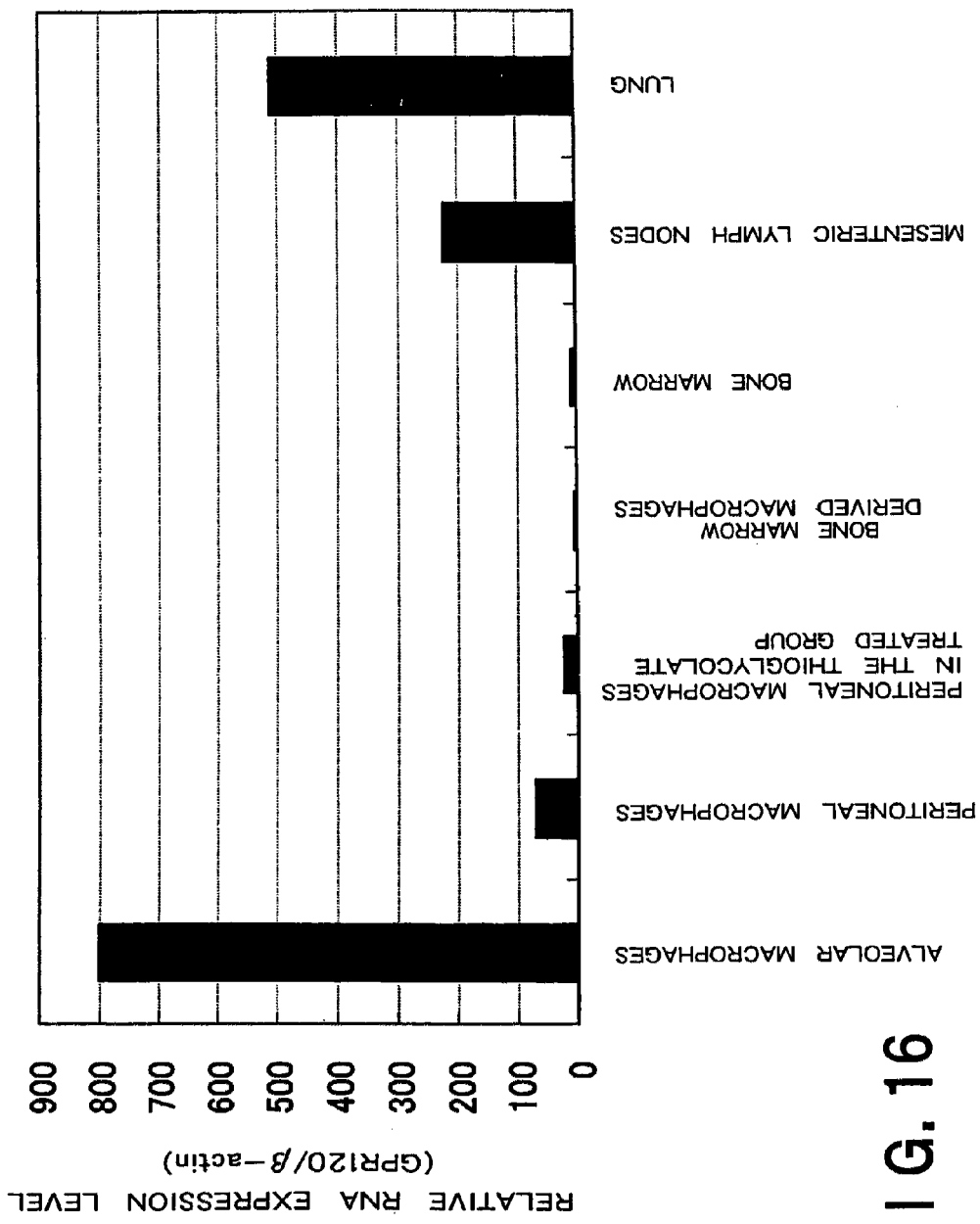
FIG. 16 shows the relative mGPR120 RNA expression level in various types of macrophages.

As shown in FIG. 16, GPR120 mRNA levels in peritoneal macrophages, peritoneal macrophages from thioglycolate treated mice and bone marrow derived macrophages were detected as one tenth or less of the expression level in alveolar macrophages. In addition, GPR120 expression was hardly detectable in bone marrow, whereas, an expression of GPR120 was observed in mesenteric lymph nodes.

Example 30

Figure 17A:
FIG. 17A shows a microscopic photograph of alveolar macrophages immediately after seeding.
Figure 17B:
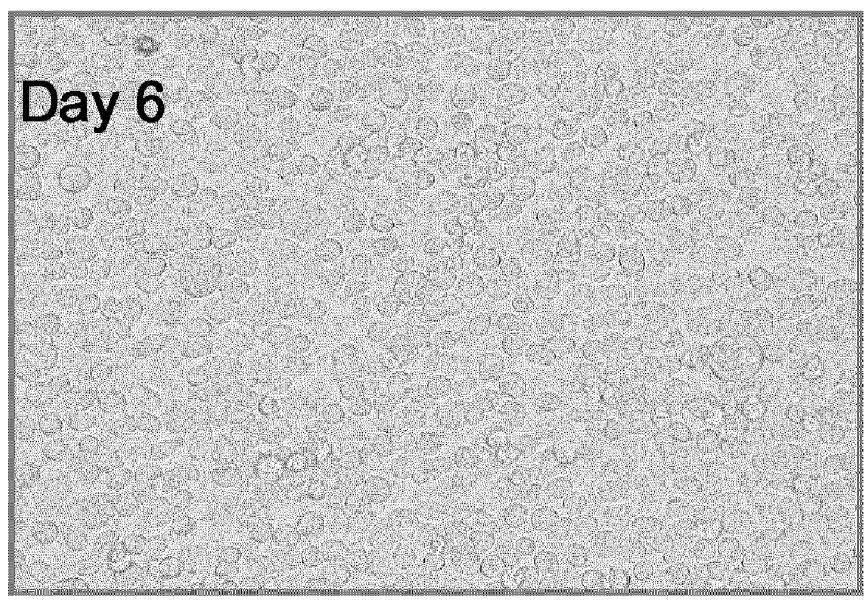
FIG. 17B shows a microscopic photograph of alveolar macrophages 6 days after seeding.
Figure 17C:
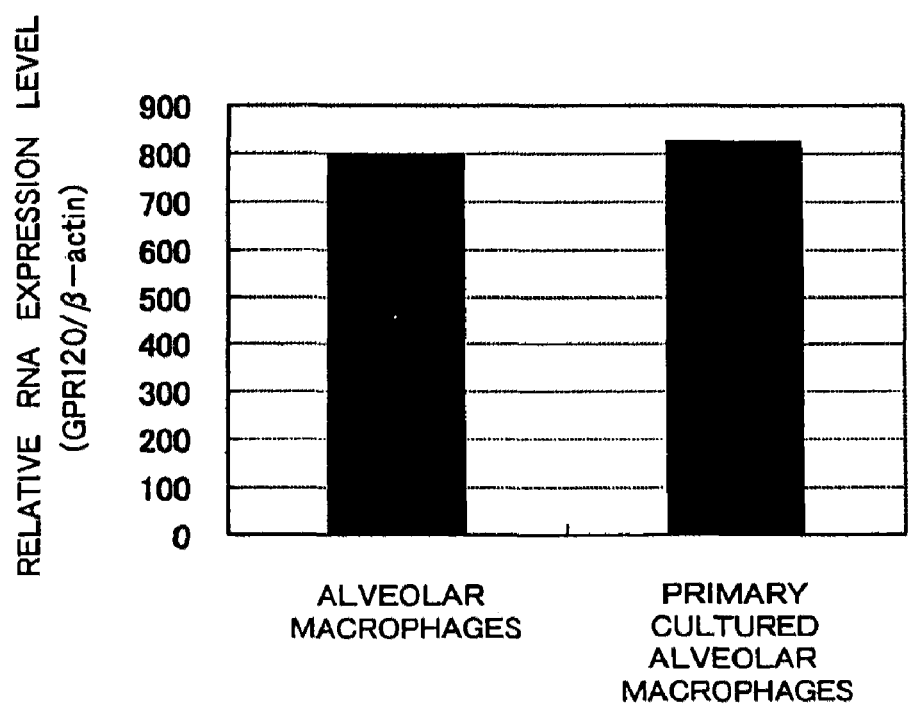
FIG. 17C shows the relative mGPR120 RNA expression level in alveolar macrophages immediately after harvesting or after 6 days in primary culture.

Quantitation of GPR120 Gene Expression in Primary Cultured Alveolar Macrophages Using the SYBR Green PCR Method Primary cultures of alveolar macrophages were carried out according to the method by Akagawa, K et al. (Akagawa, K. et al., The Journal of Immunology, Vol. 141, 3383-3390, 1988). In detail, 8-week old male C57BL/6Nrj mice (Charles River Laboratories, Japan, Inc.) were anesthetized with Nembutal and blood was removed by perfusing with PBS(−) and 10 U/mL heparin from right ventricle. Lung was isolated and dissected in PBS(−)/1 mM EDTA into 1-2 mm squares using a pair of scissors and filtered through a 70 μm cell strainer and the flow through was collected as alveolar macrophages. Cells were recovered by centrifugation at 1,500 rpm for 5 min and red blood cells were removed by treating with BD Pharm Lyse™ Lysing Buffer (Becton Dickinson, Co.). Then, cells were centrifuged again at 1,500 rpm for 5 min and suspended in RPMI 1640 medium (penicillin/streptomycin, 10% FBS, 50 μM β-mercaptoethanol) and plated in a 24 well plate. Recombinant mouse GM-CSF (R & D Systems, Co.) was added at a final concentration of 20 ng/mL and cultured for 6 days with a medium change every 2-3 days. FIG. 17A and FIG. 17B show a microscopic photograph of alveolar macrophages right after seeding and on day 6, in culture, respectively. Six days later, cells were collected and total. RNA was prepared using TRIzol Reagent (Invitrogen, Co.), and DNase treated using DNA-free (trademark) (Ambion, Co.). According to the method described in Example 8, cDNA was synthesized by reverse transcription and levels of mouse GPR120 mRNA were measured using a 5′-primer of SEQ ID NO 19 and a 3′-primer of SEQ ID NO 20 according to the method described in Example 8 with a SYBR Green PCR Core Reagents Kit. As shown in FIG. 17C, levels of GPR120 expression were maintained in primary cultured alveolar macrophages at the same level as those in alveolar macrophages immediately after isolation.

Example 31

Figure 18:
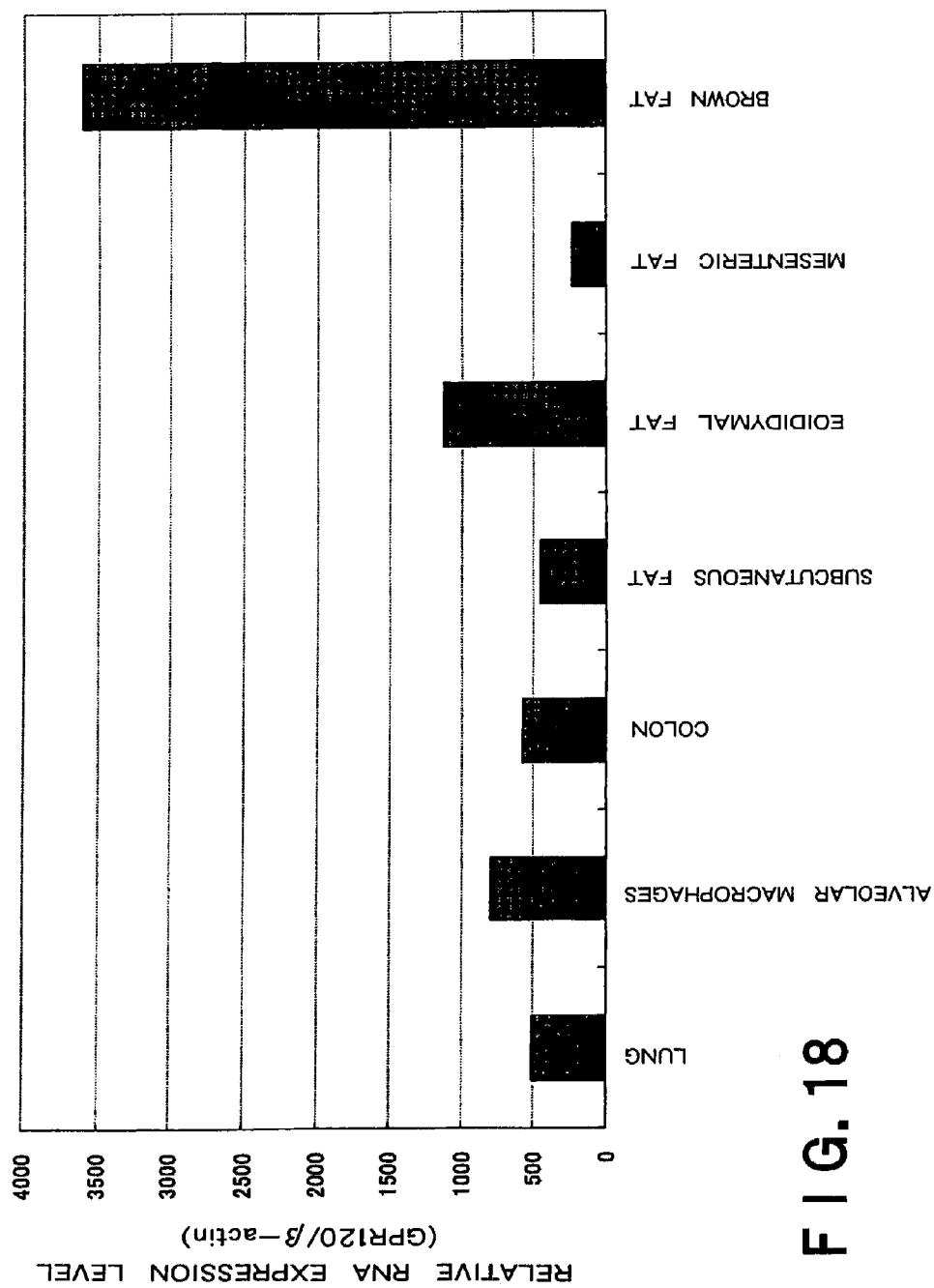
FIG. 18 shows the relative mGPR120 RNA expression level in mouse adipose tissues.

Quantitation of GPR120 Gene Expression in Adipose Tissues Using the SYBR Green PCR Method Four different types of adipose tissues (subcutaneous fat, epididymal fat, mesenteric fat and brown fat) were isolated from 8-week old male C57BL/6NCrj mice (Charles River Laboratories, Japan, Inc.) and homogenized in QIAzol™ Lysis Reagent (QIAGEN, Co.). Following chloroform extraction, total RNA was extracted using RNeasy (QIAGEN, Co.) according to the manual. The total RNA was DNase treated with DNA-free™ (Ambion, Co.) according to the manual. According to the method described in Example 8, cDNA was synthesized by reverse transcription and levels of mouse GPR120 mRNA were measured using a 5′-primer of SEQ ID NO 19 and a 3′-primer of SEQ ID NO 20 according to the method described in Example 8 with a SYBR Green PCR Core Reagents Kit. As shown in FIG. 18, GPR120 expression was observed in all adipose tissues tested, and a significantly high level of expression was observed in brown fat.

Example 32

Figure 19:
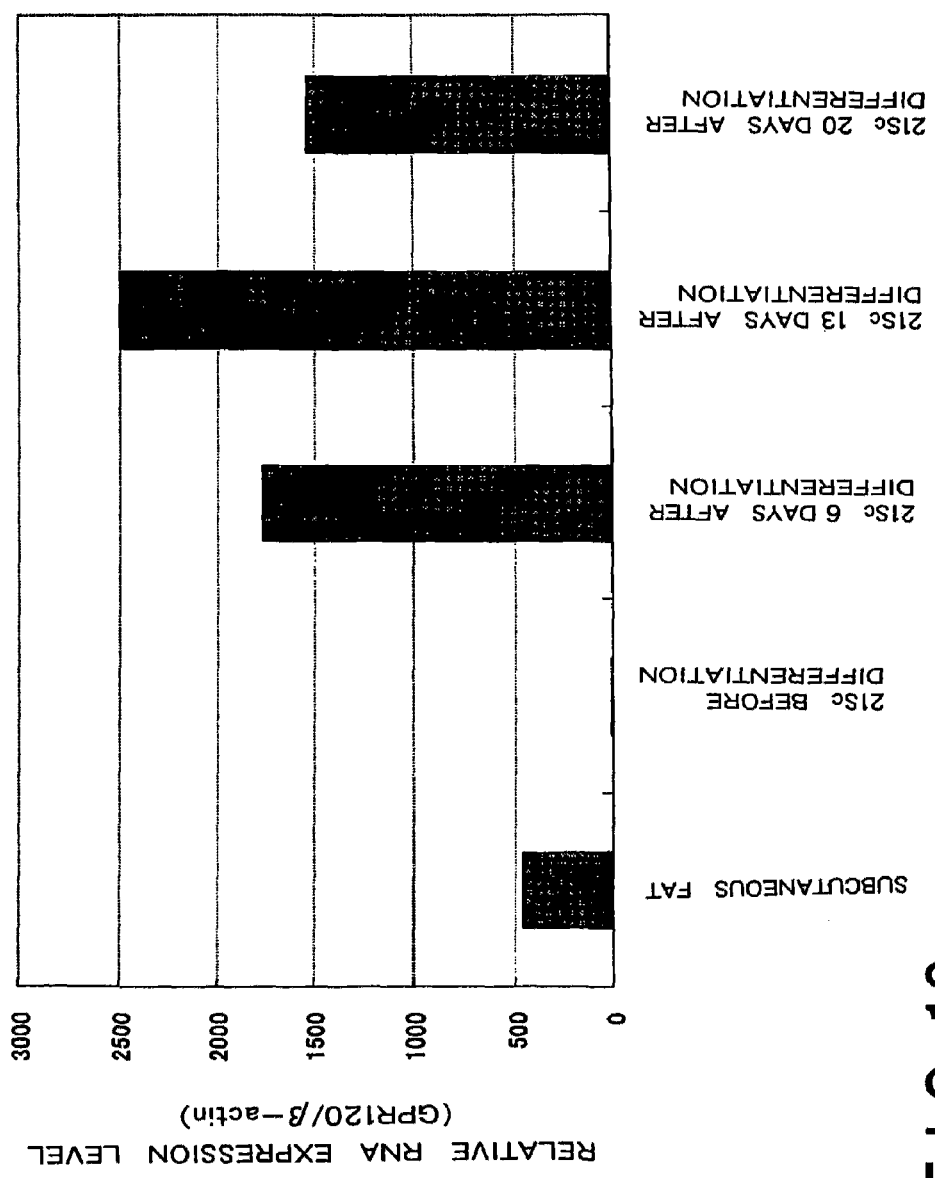
FIG. 19 shows the relative mGPR120 RNA expression level in mouse derived adipocytes.

GPR120 Expression in Mouse Derived Cultured Adipocyte Using the SYBR Green PCR Method Subcutaneous adipose tissues were excised from inguinal region of 3-4-week old male Balb/c mice (obtained from Charles River Laboratories) and adipocyte (designated as 21Sc cells) were isolated by the ceiling culture method (Sugihara, H. et al., Differentiation 1986, 31:42-49). Cells were cryopreserved after subculture. Cryopreserved 21Sc cells were defrosted and diluted to 1:4 to plate in a 6-well culture plate. Cells were cultured with the normal medium (DMEM-4.5 g/L glucose, 10% FBS, penicillin/streptomycin) for 4 days to reach confluence. Culture media were changed to the induction media (normal medium supplemented with 0.5 mM IBMX, 0.25 μM dexamethazone, 10 μg/mL insulin, and 0.2 mM indometacin) and cells were cultured for 2 days. Then media were changed to the maturation media (normal medium supplemented with 5 μg/mL insulin) and a medium change was carried out every 1-2 days. Adipocytes were collected before differentiation and on the 6th, 13th and 20th day following a change to induction media and total RNA was prepared using TRIzol Reagent; (Invitrogen, Co.) according to the manual. The obtained total RNA was DNase treated using DNA-free™ (Ambion, Co.) according to the manual. According to the method described in Example 8, cDNA was synthesized by reverse transcription and levels of mouse GPR120 mRNA were measured using a 5'-primer of SEQ ID NO 19 and a 3'-primer of SEQ ID NO 20 according to the method described in Example 8 with a SYBR Green PCR Core Reagents Kit. Levels of GPR120 mRNA expression on each day in culture are shown in FIG. 19. Compared to before induction of differentiation, a remarkable increase in GPR120 RNA level (about 200 fold) was observed in the cells after the induction of differentiation.

Example 33

Quantitation of GPR120 Gene Expression in Mouse Bone Marrow Derived Dendritic Cells Using the SYBR Green PCR Method Bone marrow was collected from femur of 8-week old male C57BL/6NCrj mice (Charles River Laboratories, Japan, Inc.), and bone marrow derived dendritic cells were obtained using the method by Luts, M. B. et al. (Luts, M. B. et al., Journal of Immunological methods 233, 77-92, 1999). Specifically, bone marrow was treated with BD Pharm Lyse™ Lysing Buffer (Becton Dickenson, Co.) for 5 min to remove red blood cells and by suspending in RPMI 1640 medium (10% FBS, penicillin/streptomycin; 50 µM mercaptoethanol) with recombinant mouse GM-CSF (R & D Systems, Co.) at a final concentration of 20 ng/mL to culture in a 75 cm² flask. Medium change was carried out every 2-3 days (RPMI 1640, penicillin/streptomycin, 50 µM mercaptoethanol, 20 ng/mL recombinant mouse GM-CSF), and cultured for 11 days to obtain bone marrow derived dendritic cells. To some of dendritic cells, 1 µg/mL of LPS (Sigma, Co.) was added on the 11th day and cells were cultured for 24 hours to obtain activated bone marrow derived dendritic cells. Total RNA from each sample was prepared using TRIzol Reagent (Invitrogen, Co.) according to the manual. The obtained total RNA was DNase treated using DNA-free™ (Ambion, Co.) according to the manual. According to the method described in Example 8, cDNA was synthesized by reverse transcription and levels of mouse GPR120 mRNA were measured using a 5'-primer of SEQ ID NO 19 and a 3'-primer of SEQ ID NO 20 according to the method described in Example 8 with a SYBR Green PCR Core Reagents Kit. As shown in FIG. 20, an expression of GPR120 in bone marrow derived dendritic cells was observed. In addition, following 24-hour stimulation with 1 µg/mL of LPS, the expression level of GPR120 was about one fifth of the level observed before stimulation.

The invention claimed is:

1. A screening method for determining whether a substance of interest is a substance which alters GPR120-mediated cell-stimulating activities, comprising the following steps:
   (1) contacting a biomembrane containing GPR120 or cells containing said biomembrane with secretory phospholipase A2 or salts thereof in the presence and absence of the substance of interest;
   (2) measuring cell-stimulating activities;
   (3) comparing a result measured in the presence of the substance of interest with a result measured in absence of the substance of interest; and
   (4) determining that the substance of interest is the substance that alters GPR120-mediated cell-stimulating activities, in the case where there is a difference between results measured in the presence and absence of the substance of interest.

2. The method according to claim 1, wherein the secretory phospholipase A2 is selected from the group consisting of Group IB secretory phospholipase A2, Group IIA secretory phospholipase A2, Group IIC secretory phospholipase A2, Group IID secretory phospholipase A2, Group IIE secretory phospholipase A2, Group IIF secretory phospholipase A2, Group III secretory phospholipase A2, Group V secretory phospholipase A2, Group X secretory phospholipase A2, Group XIIA secretory phospholipase A2, honey bee venom phospholipase A2, snake venom phospholipase A2, and a mixture thereof.

3. The method according to claim 1, wherein the secretory phospholipase A2 is selected from the group consisting of Group IB secretory phospholipase A2, Group X secretory phospholipase A2, honey bee venom phospholipase A2, snake venom phospholipase A2, and a mixture thereof.

4. The method according to any one of claims 1, 2, and 3, wherein the measurement of cell stimulating activities is performed either by using the reporter-assay system that detects a change in translation/transcription level of a reporter gene caused by a production of signal transduction substances, or by measuring a parameter selected from the group consisting of intracellular calcium ion release, activation of adenylate cyclase, intracellular cAMP production, intracellular cGMP production, release of arachidonic acid, release of acetylcholine, production of inositol phosphate, a change in cellular membrane potential, phosphorylation or activation of intracellular proteins, pH changing activities, phosphorylation or activation of MAP kinase, activation of c-fos, glycerol production activities, lipolysis activities, adrenocorticotropic hormone (ACTH) secretion activities, cholestikinin (CCK) secretion activities, and glucagon like peptide (GLP-1) secretion activities.

5. The method according to any one of claims 1, 2, and 3, wherein GPR120 is composed of a polypeptide selected from the group consisting of (a), (b), and (c) below:
   (a) a polypeptide comprising the amino acid sequence of SEQ ID NO 2;
   (b) a polypeptide consisting of the amino acid sequence having 95% or higher identity to the amino acid sequence of SEQ ID NO 2; and
   (c) a polypeptide encoded by a polynucleotide consisting of the base sequence having 95% or higher identity to the base sequence of SEQ ID NO 1, and having substantially the same activity as GPR120.

6. A screening kit comprising, at least, a biomembrane containing GPR120 or cells containing said biomembrane, and secretory phospholipase A2 or salts thereof for screening of a substance that alters GPR120-mediated cell-stimulating activities.

7. The kit according to claim 6, wherein said GPR120 is composed of a polypeptide selected from the group consisting of (a) to (c) below:
   (a) a polypeptide comprising the amino acid sequence of SEQ ID NO 2;
   (b) a polypeptide consisting of the amino acid sequence having 95% or higher identity to the amino acid sequence of SEQ ID NO 2; and
   (c) a polypeptide encoded by a polynucleotide consisting of the base sequence having 95% or higher identity to the base sequence of SEQ ID NO 1, and having substantially the same activity as GPR120.

8. The kit according to claim 6 or 7, wherein the phospholipase is selected from the group consisting of Group IB secretory phospholipase A2, Group MA secretory phospholipase A2, Group IIC secretory phospholipase A2, Group IID secretory phospholipase A2, Group HE secretory phospholipase A2, Group IIF secretory phospholipase A2, Group III secretory phospholipase A2, Group V secretory phospholipase A2, Group X secretory phospholipase A2, Group XIIA secretory phospholipase A2, honey bee venom phospholipase A2, snake venom phospholipase A2, and a mixture thereof.

9. The kit according to claim 6 or 7, wherein the phospholipase is selected from the group consisting of Group IB secretory phospholipase A2, Group X secretory phospholipase A2, honey bee venom phospholipase A2, snake venom phospholipase A2 and a mixture thereof.

* * * * *

SEQUENCE LISTING

```
<160> NUMBER OF SEQ ID NOS: 47

<210> SEQ ID NO 1
<211> LENGTH: 1086
<212> TYPE: DNA
<213> ORGANISM: Homo sapiens

<400> SEQUENCE: 1 atgtccctg aatgcgcgcg ggcagcgggc gacgcgccct tgcgcagcct ggagcaagcc      60
aaccgcaccc gctttccctt cttctccgac gtcaagggcg accaccggct ggtgctggcc     120
gcggtggaga caaccgtgct ggtgctcatc tttgcagtgt cgctgctggg caacgtgtgc     180
gccctggtgc tggtggcgcg ccgacgacgc cgcggcgcga ctgcctgcct ggtactcaac     240
ctcttctgcg cggacctgct cttcatcagc gctatccctc tggtgctggc cgtgcgctgg     300
actgaggcct ggctgctggg cccgttgcc tgccacctgc tcttctacgt gatgaccctg     360
agcggcagcg tcaccatcct cacgctggcc gcggtcagcc tggagcgcat ggtgtgcatc     420
gtgcacctgc agcgcggcgt gcggggtcct gggcggcggg cgcgggcagt gctgctggcg     480
ctcatctggg gctattcggc ggtcgccgct ctgcctctct gcgtcttctt ccgagtcgtc     540
ccgcaacggc tccccggcgc cgaccaggaa atttcgattt gcacactgat ttggcccacc     600
attcctggag agatctcgtg ggatgtctct tttgttactt tgaacttctt ggtgccagga     660
ctggtcattg tgatcagtta ctccaaaatt ttacagatca caaaggcatc aaggaagagg     720
ctcacggtaa gcctggccta ctcggagagc caccagatcc gcgtgtccca gcaggacttc     780
cggctcttcc gcacccctctt cctcctcatg gtctccttct tcatcatgtg gagccccatc     840
atcatcacca tcctcctcat cctgatccag aacttcaagc aagacctggt catctggccg     900
tccctcttct tctgggtggt ggccttcaca tttgctaatt cagccctaaa ccccatcctc     960
tacaacatga cactgtgcag gaatgagtgg aagaaaattt tttgctgctt ctggttccca    1020
```

```
gaaaagggag ccattttaac agacacatct gtcaaaagaa atgacttgtc gattatttct  1080
ggctaa                                                              1086
```

<210> SEQ ID NO 2
<211> LENGTH: 361
<212> TYPE: PRT
<213> ORGANISM: Homo sapiens

<400> SEQUENCE: 2

```
Met Ser Pro Glu Cys Ala Arg Ala Ala Gly Asp Ala Pro Leu Arg Ser
1               5                  10                  15

Leu Glu Gln Ala Asn Arg Thr Arg Phe Pro Phe Ser Asp Val Lys
            20                  25                  30

Gly Asp His Arg Leu Val Leu Ala Ala Val Glu Thr Thr Val Leu Val
        35                  40                  45

Leu Ile Phe Ala Val Ser Leu Leu Gly Asn Val Cys Ala Leu Val Leu
    50                  55                  60

Val Ala Arg Arg Arg Arg Gly Ala Thr Ala Cys Leu Val Leu Asn
65                  70                  75                  80

Leu Phe Cys Ala Asp Leu Leu Phe Ile Ser Ala Ile Pro Leu Val Leu
            85                  90                  95

Ala Val Arg Trp Thr Glu Ala Trp Leu Leu Gly Pro Val Ala Cys His
            100                 105                 110

Leu Leu Phe Tyr Val Met Thr Leu Ser Gly Ser Val Thr Ile Leu Thr
        115                 120                 125

Leu Ala Ala Val Ser Leu Glu Arg Met Val Cys Ile Val His Leu Gln
    130                 135                 140

Arg Gly Val Arg Gly Pro Gly Arg Arg Ala Arg Ala Val Leu Leu Ala
145                 150                 155                 160

Leu Ile Trp Gly Tyr Ser Ala Val Ala Ala Leu Pro Leu Cys Val Phe
            165                 170                 175

Phe Arg Val Val Pro Gln Arg Leu Pro Gly Ala Asp Gln Glu Ile Ser
            180                 185                 190

Ile Cys Thr Leu Ile Trp Pro Thr Ile Pro Gly Glu Ile Ser Trp Asp
        195                 200                 205

Val Ser Phe Val Thr Leu Asn Phe Leu Val Pro Gly Leu Val Ile Val
    210                 215                 220

Ile Ser Tyr Ser Lys Ile Leu Gln Ile Thr Lys Ala Ser Arg Lys Arg
225                 230                 235                 240

Leu Thr Val Ser Leu Ala Tyr Ser Glu Ser His Gln Ile Arg Val Ser
            245                 250                 255

Gln Gln Asp Phe Arg Leu Phe Arg Thr Leu Phe Leu Leu Met Val Ser
            260                 265                 270

Phe Phe Ile Met Trp Ser Pro Ile Ile Ile Thr Ile Leu Leu Ile Leu
        275                 280                 285

Ile Gln Asn Phe Lys Gln Asp Leu Val Ile Trp Pro Ser Leu Phe Phe
    290                 295                 300

Trp Val Val Ala Phe Thr Phe Ala Asn Ser Ala Leu Asn Pro Ile Leu
305                 310                 315                 320

Tyr Asn Met Thr Leu Cys Arg Asn Glu Trp Lys Lys Ile Phe Cys Cys
            325                 330                 335

Phe Trp Phe Pro Glu Lys Gly Ala Ile Leu Thr Asp Thr Ser Val Lys
            340                 345                 350

Arg Asn Asp Leu Ser Ile Ile Ser Gly
```

<210> SEQ ID NO 3
<211> LENGTH: 1086
<212> TYPE: DNA
<213> ORGANISM: Mus musculus

<400> SEQUENCE: 3

```
atgtccnctg agtgtgcaca gacgacgggc cctggcccct cgcacaccct ggaccaagtc    60
aatcgcaccc acttcccttt cttctcggat gtcaagggcg accaccggtt ggtgttgagc   120
gtcgtggaga ccaccgttct ggggctcatc tttgtcgtct cactgctggg caacgtgtgt   180
gctctagtgc tggtggcgcg ccgtcggcgc cgtggggcga cagccagcct ggtgctcaac   240
ctcttctgcg cggatttgct cttcaccagc gccatccctc tagtgctcgt cgtgcgctgg   300
actgaggcct ggctgttggg gcccgtcgtc tgccacctgc tcttctacgt gatgacaatg   360
agcggcagcg tcacgatcct cacactggcc gcggtcagcc tggagcgcat ggtgtgcatc   420
gtgcgcctcc ggcgcggctt gagcggcccg gggcggcgga ctcaggcggc actgctggct   480
ttcatatggg gttactcggc gctcgccgcg ctgcccctct gcatcttgtt ccgcgtggtc   540
ccgcagcgcc ttcccggcgg ggaccaggaa attccgattt gcacattgga ttggcccaac   600
cgcataggag aaatctcatg ggatgtgttt tttgtgactt tgaacttcct ggtgccggga   660
ctggtcattg tgatcagtta ctccaaaatt ttacagatca cgaaagcatc gcggaagagg   720
cttacgctga gcttggcata ctctgagagc caccagatcc gagtgtccca acaagactac   780
cgactcttcc gcacgctctt cctgctcatg gtttccttct tcatcatgtg gagtcccatc   840
atcatcacca tcctcctcat cttgatccaa aacttccggc aggacctggt catctggcca   900
tccctttttct tctgggtggt ggccttcacg tttgccaact ctgccctaaa ccccatactg   960
tacaacatgt cgctgttcag gaacgaatgg aggaagattt tttgctgctt cttttttcca  1020
gagaagggag ccattttttac agacacgtct gtcaggcgaa atgacttgtc tgttatttcc  1080
agctaa                                                              1086
```

<210> SEQ ID NO 4
<211> LENGTH: 361
<212> TYPE: PRT
<213> ORGANISM: Mus musculus

<400> SEQUENCE: 4

```
Met Ser Pro Glu Cys Ala Gln Thr Thr Gly Pro Gly Pro Ser His Thr
 1               5                  10                  15

Leu Asp Gln Val Asn Arg Thr His Phe Pro Phe Phe Ser Asp Val Lys
            20                  25                  30

Gly Asp His Arg Leu Val Leu Ser Val Val Glu Thr Thr Val Leu Gly
        35                  40                  45

Leu Ile Phe Val Val Ser Leu Leu Gly Asn Val Cys Ala Leu Val Leu
    50                  55                  60

Val Ala Arg Arg Arg Arg Arg Gly Ala Thr Ala Ser Leu Val Leu Asn
65                  70                  75                  80

Leu Phe Cys Ala Asp Leu Leu Phe Thr Ser Ala Ile Pro Leu Val Leu
                85                  90                  95

Val Val Arg Trp Thr Glu Ala Trp Leu Leu Gly Pro Val Val Cys His
            100                 105                 110

Leu Leu Phe Tyr Val Met Thr Met Ser Gly Ser Val Thr Ile Leu Thr
        115                 120                 125
```

```
Leu Ala Ala Val Ser Leu Glu Arg Met Val Cys Ile Val Arg Leu Arg
            130                 135                 140

Arg Gly Leu Ser Gly Pro Gly Arg Arg Thr Gln Ala Ala Leu Leu Ala
145                 150                 155                 160

Phe Ile Trp Gly Tyr Ser Ala Leu Ala Ala Leu Pro Leu Cys Ile Leu
                165                 170                 175

Phe Arg Val Val Pro Gln Arg Leu Pro Gly Gly Asp Gln Glu Ile Pro
            180                 185                 190

Ile Cys Thr Leu Asp Trp Pro Asn Arg Ile Gly Glu Ile Ser Trp Asp
                195                 200                 205

Val Phe Phe Val Thr Leu Asn Phe Leu Val Pro Gly Leu Val Ile Val
            210                 215                 220

Ile Ser Tyr Ser Lys Ile Leu Gln Ile Thr Lys Ala Ser Arg Lys Arg
225                 230                 235                 240

Leu Thr Leu Ser Leu Ala Tyr Ser Glu Ser His Gln Ile Arg Val Ser
                245                 250                 255

Gln Gln Asp Tyr Arg Leu Phe Arg Thr Leu Phe Leu Leu Met Val Ser
            260                 265                 270

Phe Phe Ile Met Trp Ser Pro Ile Ile Thr Ile Leu Leu Ile Leu
            275                 280                 285

Ile Gln Asn Phe Arg Gln Asp Leu Val Ile Trp Pro Ser Leu Phe Phe
290                 295                 300

Trp Val Val Ala Phe Thr Phe Ala Asn Ser Ala Leu Asn Pro Ile Leu
305                 310                 315                 320

Tyr Asn Met Ser Leu Phe Arg Asn Glu Trp Arg Lys Ile Phe Cys Cys
                325                 330                 335

Phe Phe Phe Pro Glu Lys Gly Ala Ile Phe Thr Asp Thr Ser Val Arg
            340                 345                 350

Arg Asn Asp Leu Ser Val Ile Ser Ser
            355                 360

<210> SEQ ID NO 5
<211> LENGTH: 1203
<212> TYPE: DNA
<213> ORGANISM: Rattus norvegicus

<400> SEQUENCE: 5
atggcagcca actcagacct catggccagc aagtttggca ttggtatggt gttgctgaca      60
gtcagttacc tcgcagatga acgctctcac agacagcggc gcggccgggc gcccggcatg     120
tcccctgagt gtgcgcagac gacgggccct ggcccctcgc gcaccccgga ccaagtcaat     180
cgcacccact cccttttctt ctcggatgtc aagggcgacc accggctggt gctgagcgtc     240
ctggagacca ccgttctggg actcatcttt gtggtctcac tgctgggcaa cgtgtgtgcc     300
ctggtgctgg tggtgcgccg tcggcgccgt ggggcgacag tcagcttggt gctcaacctc     360
ttctgcgcgg atttgctctt caccagcgcc atccctctag tgctcgtggt gcgctggact     420
gaagcctggc tgctgggccc cgtcgtctgt cacctgctct tctacgtgat gaccatgagc     480
ggcagcgtca cgatcctcac gctggccgcg gtcagcctgg agcgcatggt gtgcatcgtg     540
cgcctgcggc gcggcttgag cggcccgggg cggcggacgc aggcggcgct gctggctttc     600
atatggggtt actcggcgct cgccgcgctg cccctctgca tcttgttccg cgtggtcccg     660
cagcgccttc ccggcgggga ccaggaaatt ccgatttgca cattggattg gcccaaccgc     720
ataggagaaa tctcatggga tgtgttttt gtgactttga cttcctggt accaggactg     780 gtcattgtga tcagctactc caagatttta cagatcacga aagcctcgcg gaagaggctt     840
```

-continued

```
acgctgagct tggcatactc cgagagccac cagatccgag tgtcccagca ggactaccgg    900
ctcttccgaa cgctcttcct gctcatggtt tccttcttca tcatgtggag tcccatcatc    960
atcaccatcc tcctcatctt gatccagaac ttccggcagg acctggttat ctggccgtcc   1020
cttttcttct gggtggtggc cttcacgttt gccaactccg ccctaaaccc cattctgtac   1080
aacatgtcgc tgttcaggag cgagtggagg aagatttttt gctgcttctt tttcccagag   1140
aagggagcca ttttacaga aacgtctatc aggcgaaatg acttgtctgt tatttccacc   1200
taa                                                                 1203
```

<210> SEQ ID NO 6
<211> LENGTH: 400
<212> TYPE: PRT
<213> ORGANISM: Rattus norvegicus

<400> SEQUENCE: 6

```
Met Ala Ala Asn Ser Asp Leu Met Ala Ser Lys Phe Gly Ile Gly Met
1               5                   10                  15

Val Leu Leu Thr Val Ser Tyr Leu Ala Asp Glu Arg Ser His Arg Gln
            20                  25                  30

Arg Arg Gly Arg Ala Pro Gly Met Ser Pro Glu Cys Ala Gln Thr Thr
        35                  40                  45

Gly Pro Gly Pro Ser Arg Thr Pro Asp Gln Val Asn Arg Thr His Phe
    50                  55                  60

Pro Phe Phe Ser Asp Val Lys Gly Asp His Arg Leu Val Leu Ser Val
65                  70                  75                  80

Leu Glu Thr Thr Val Leu Gly Leu Ile Phe Val Val Ser Leu Leu Gly
                85                  90                  95

Asn Val Cys Ala Leu Val Leu Val Arg Arg Arg Arg Arg Arg Gly Ala
            100                 105                 110

Thr Val Ser Leu Val Leu Asn Leu Phe Cys Ala Asp Leu Leu Phe Thr
        115                 120                 125

Ser Ala Ile Pro Leu Val Leu Val Val Arg Trp Thr Glu Ala Trp Leu
    130                 135                 140

Leu Gly Pro Val Val Cys His Leu Leu Phe Tyr Val Met Thr Met Ser
145                 150                 155                 160

Gly Ser Val Thr Ile Leu Thr Leu Ala Ala Val Ser Leu Glu Arg Met
                165                 170                 175

Val Cys Ile Val Arg Leu Arg Arg Gly Leu Ser Gly Pro Gly Arg Arg
            180                 185                 190

Thr Gln Ala Ala Leu Leu Ala Phe Ile Trp Gly Tyr Ser Ala Leu Ala
        195                 200                 205

Ala Leu Pro Leu Cys Ile Leu Phe Arg Val Val Pro Gln Arg Leu Pro
    210                 215                 220

Gly Gly Asp Gln Glu Ile Pro Ile Cys Thr Leu Asp Trp Pro Asn Arg
225                 230                 235                 240

Ile Gly Glu Ile Ser Trp Asp Val Phe Phe Val Thr Leu Asn Phe Leu
                245                 250                 255

Val Pro Gly Leu Val Ile Val Ile Ser Tyr Ser Lys Ile Leu Gln Ile
            260                 265                 270

Thr Lys Ala Ser Arg Lys Arg Leu Thr Leu Ser Leu Ala Tyr Ser Glu
        275                 280                 285

Ser His Gln Ile Arg Val Ser Gln Gln Asp Tyr Arg Leu Phe Arg Thr
    290                 295                 300
```

```
Leu Phe Leu Leu Met Val Ser Phe Ile Met Trp Ser Pro Ile Ile
305                 310                 315                 320

Ile Thr Ile Leu Leu Ile Leu Ile Gln Asn Phe Arg Gln Asp Leu Val
                325                 330                 335

Ile Trp Pro Ser Leu Phe Phe Trp Val Val Ala Phe Thr Phe Ala Asn
            340                 345                 350

Ser Ala Leu Asn Pro Ile Leu Tyr Asn Met Ser Leu Phe Arg Ser Glu
        355                 360                 365

Trp Arg Lys Ile Phe Cys Cys Phe Phe Pro Glu Lys Gly Ala Ile
    370                 375                 380

Phe Thr Glu Thr Ser Ile Arg Arg Asn Asp Leu Ser Val Ile Ser Thr
385                 390                 395                 400

<210> SEQ ID NO 7
<211> LENGTH: 39
<212> TYPE: DNA
<213> ORGANISM: Artificial
<220> FEATURE:
<223> OTHER INFORMATION: primer

<400> SEQUENCE: 7
gatatcgccg ccaccatgtc ccctgaatgc gcgcgggca                    39

<210> SEQ ID NO 8
<211> LENGTH: 30
<212> TYPE: DNA
<213> ORGANISM: Artificial
<220> FEATURE:
<223> OTHER INFORMATION: primer

<400> SEQUENCE: 8
gatatcttag ccagaaataa tcgacaagtc                              30

<210> SEQ ID NO 9
<211> LENGTH: 42
<212> TYPE: DNA
<213> ORGANISM: Artificial
<220> FEATURE:
<223> OTHER INFORMATION: primer

<400> SEQUENCE: 9
gatatcgccg ccaccatgtc ccctgagtgt gcacagacga cg                 42

<210> SEQ ID NO 10
<211> LENGTH: 31
<212> TYPE: DNA
<213> ORGANISM: Artificial
<220> FEATURE:
<223> OTHER INFORMATION: primer

<400> SEQUENCE: 10
gatatcttag ctggaaataa cagacaagtc a                            31

<210> SEQ ID NO 11
<211> LENGTH: 5020
<212> TYPE: DNA
<213> ORGANISM: Artificial
<220> FEATURE:
<223> OTHER INFORMATION: probe

<400> SEQUENCE: 11
ctgcagcctg aatatgggcc aaacaggata tctgtggtaa gcagttcctg ccccggctca    60
gggccaagaa cagatggaac agctgaatat gggccaaaca ggatatctgt ggtaagcagt   120
```

-continued

| | |
|---|---|
| tcctgccccg gctcagggcc aagaacagat ggtccccaga tgcggtccag ccctcagcag | 180 |
| tttctagaga accatcagat gtttccaggg tgccccaagg acctgaaatg accctgtgcc | 240 |
| ttatttgaac taaccaatca gttcgcttct cgcttctgtt cgcgcgcttc tgctccccga | 300 |
| gctcaataaa agagcccaca acccctcact cggggcgcca gtcctccgat tgactgagtc | 360 |
| gcccgggtac ccgtgtatcc aataaaccct cttgcagttg catccgactt gtggtctcgc | 420 |
| tgttccttgg gagggtctcc tctgagtgat tgactacccg tcagcggggg tctttcattt | 480 |
| gggggctcgt ccgggatcgg gagacccctg cccagggacc accgacccac caccgggagg | 540 |
| taagctggcc agcaacttat ctgtgtctgt ccgattgtct agtgtctatg actgatttta | 600 |
| tgcgcctgcg tcggtactag ttagctaact agctctgtat ctggcggacc cgtggtggaa | 660 |
| ctgacgagtt ctgaacaccc ggccgcaacc ctggagacg tcccaggac tttggggcc | 720 |
| gttttttgtgg cccgacctga ggaagggagt cgatgtggaa tccgaccccg tcaggatatg | 780 |
| tggttctggt aggagacgag aacctaaaac agttcccgcc tccgtctgaa tttttgcttt | 840 |
| cggtttggaa ccgaagccgc gcgtcttgtc tgctgcagca tcgttctgtg ttgtctctgt | 900 |
| ctgactgtgt ttctgtattt gtctgaaaat tagggccaga ctgttaccac tcccttaagt | 960 |
| ttgaccttag atcactggaa agatgtcgag cggctcgctc acaaccagtc ggtagatgtc | 1020 |
| aagaagagac gttgggttac cttctgctct gcagaatggc caacctttaa cgtcggatgg | 1080 |
| ccgcgagacg gcacctttaa ccgagacctc atcacccagg ttaagatcaa ggtcttttca | 1140 |
| cctggcccgc atggacaccc agaccaggtc ccctacatcg tgacctggga agccttggct | 1200 |
| tttgaccccc ctccctgggt caagcccttt gtacacccta agcctccgcc tcctcttctt | 1260 |
| ccatccgcgc cgtctctccc ccttgaacct cctctttcga ccccgcctca atcctccctt | 1320 |
| tatccagccc tcactccttc tctaggcgcc ggccggatcc cagtgtggtg gtacgtagga | 1380 |
| attcgccagc acagtggtcg acctgtggaa tgtgtgtcag ttagggtgtg aaagtccccc | 1440 |
| aggctcccca gcaggcagaa gtatgcaaag catgcatctc aattagtcag caaccaggtg | 1500 |
| tggaaagtcc ccaggctccc cagcaggcag aagtatgcaa agcatgcatc tcaattagtc | 1560 |
| agcaaccata gtcccgcccc taactccgcc catcccgccc ctaactccgc ccagttccgc | 1620 |
| ccattctccg ccccatggct gactaatttt ttttatttat gcagaggccg aggccgcctc | 1680 |
| ggcctctgag ctattccaga agtagtgagg aggcttttt ggaggcctag cttttgcaa | 1740 |
| acgctgcttg aggctgaagg tgcgttgctg gcgttttcc ataggctccg ccccctgac | 1800 |
| gagcatcaca aaaatcgacg ctcaagtcag aggtggcgaa acccgacagg actataaaga | 1860 |
| taccaggcgt ttccccctgg aagctccctc gtgcgctctc ctgttccgac cctgccgctt | 1920 |
| accggatacc tgtccgcctt tctcccttcg ggaagcgtgg cgctttctca tagctcacgc | 1980 |
| tgtaggtatc tcagttcggt gtaggtcgtt cgctccaagc tgggctgtgt gcacgaaccc | 2040 |
| cccgttcagc ccgaccgctg cgccttatcc ggtaactatc gtcttgagtc aacccggta | 2100 |
| agacacgact tatcgccact ggcagcagcc actggtaaca ggattagcag agcgaggtat | 2160 |
| gtaggcggtg ctacagagtt cttgaagtgg tggcctaact acggctacac tagaaggaca | 2220 |
| gtatttggta tctgcgctct gctgaagcca gttaccttcg aaaaagagt tggtagctct | 2280 |
| tgatccgca aacaaccac cgctggtagc ggtggttttt ttgtttgcaa gcagcagatt | 2340 |
| acgatcgata aaataaaaga tttttatttag tctccagaaa aagggggaa tgaaagaccc | 2400 |
| cacctgtagg tttggcaagc tagcttaagt aacgccattt tgcaaggcat ggaaaaatac | 2460 |
| ataactgaga atagagaagt tcagatcaag gtcaggaaca gatggaacag ctgaatatgg | 2520 |

```
gccaaacagg atatctgtgg taagcagttc ctgccccggc tcagggccaa gaacagatgg    2580
aacagctgaa tatgggccaa acaggatatc tgtggtaagc agttcctgcc ccggctcagg    2640
gccaagaaca gatggtcccc agatgcggtc cagccctcag cagtttctag agaaccatca    2700
gatgtttcca gggtgcccca aggacctgaa atgaccctgt gccttatttg aactaaccaa    2760
tcagttcgct tctcgcttct gttcgcgcgc ttctgctccc cgagctcaat aaaagagccc    2820
acaacccctc actcggggcg ccagtcctcc gattgactga gtcgcccggg tacccgtgta    2880
tccaataaac cctcttgcag ttgcatccga cttgtggtct cgctgttcct tgggagggtc    2940
tcctctgagt gattgactac ccgtcagcgg gggtctttca catgcagcat gtatcaaaat    3000
taatttggtt ttttttctta agtatttaca ttaaatggcc atagttgcat taatgaatcg    3060
gccaacgcgc ggggagaggc ggtttgcgta ttgggcgctc ttccgcttcc tcgctcactg    3120
actcgctgcg ctcggtcgtt cggctgcggc gagcggtatc agctcactca aaggcggtaa    3180
tacggttatc cacagaatca ggggataacg caggaaagaa catgtgagca aaaggccagc    3240
aaaaggccag gaaccgtaaa aaggccgcgt tgctggcgtt tttccatagg ctccgccccc    3300
ctgacgagca tcacaaaaat cgacgctcaa gtcagaggtg gcgaaacccg acaggactat    3360
aaagatacca ggcgtttccc cctggaagct ccctcgtgcg ctctcctgtt ccgaccctgc    3420
cgcttaccgg atacctgtcc gcctttctcc cttcgggaag cgtggcgctt tctcatagct    3480
cacgctgtag gtatctcagt tcggtgtagg tcgttcgctc caagctgggc tgtgtgcacg    3540
aaccccccgt tcagcccgac cgctgcgcct tatccggtaa ctatcgtctt gagtccaacc    3600
cggtaagaca cgacttatcg ccactggcag cagccactgg taacaggatt agcagagcga    3660
ggtatgtagg cggtgctaca gagttcttga agtggtggcc taactacggc tacactagaa    3720
ggacagtatt tggtatctgc gctctgctga agccagttac cttcggaaaa agagttggta    3780
gctcttgatc cggcaaacaa accaccgctg gtagcggtgg ttttttttgtt tgcaagcagc    3840 agattacgcg cagaaaaaaa ggatctcaag aagatccttt gatcttttct acggggtctg    3900
acgctcagtg gaacgaaaac tcacgttaag ggattttggt catgagatta tcaaaaagga    3960
tcttcaccta gatccttttta aattaaaaat gaagttttgcg ccgcaaatc aatctaaagt    4020 atatatgagt aaacttggtc tgacagttac caatgcttaa tcagtgaggc acctatctca    4080
gcgatctgtc tatttcgttc atccatagtt gcctgactcc ccgtcgtgta gataactacg    4140
atacgggagg gcttaccatc tggccccagt gctgcaatga taccgcgaga cccacgctca    4200
ccggctccag atttatcagc aataaaccag ccagccggaa gggccgagcg cagaagtggt    4260
cctgcaactt tatccgcctc catccagtct attaattgtt gccgggaagc tagagtaagt    4320
agttcgccca ttaatagttt gcgcaacgtt gttgccattg ctacaggcat cgtggtgtca    4380
cgctcgtcgt ttggtatggc ttcattcagc tccggttccc aacgatcaag gcgagttaca    4440
tgatccccca tgttgtgcaa aaaagcggtt agctccttcg gtcctccgat cgttgtcaga    4500
agtaagttgg ccgcagtgtt atcactcatg gttatggcag cactgcataa ttctcttact    4560
gtcatgccat ccgtaagatg cttttctgtg actggtgagt actcaaccaa gtcattctga    4620
gaatagtgta tgcggcgacc gagttgctct tgcccggcgt caacacggga taataccgcg    4680
ccacatagca gaactttaaa agtgctcatc attggaaaac gttcttcggg gcgaaaactc    4740
tcaaggatct taccgctgtt gagatccagt tcgatgtaac ccactcgtgc acccaactga    4800
tcttcagcat cttttacttt caccagcgtt tctgggtgag caaaaacagg aaggcaaaat    4860
gccgcaaaaa agggaataag ggcgacacgg aaatgttgaa tactcatact cttccttttt    4920
```

```
caatattatt gaagcattta tcagggttat tgtctcatga gcggatacat atttgaatgt    4980
atttagaaaa ataaacaaat aggggttccg cgcacatttc                         5020
```

<210> SEQ ID NO 12
<211> LENGTH: 83
<212> TYPE: DNA
<213> ORGANISM: Artificial
<220> FEATURE:
<223> OTHER INFORMATION: primer

<400> SEQUENCE: 12

```
cccaagcttg atatcgaatt cgacgtcaca gtatgacggc catgggaatt cgacgtcaca     60
gtatgacggc catggggatc ccg                                             83
```

<210> SEQ ID NO 13
<211> LENGTH: 83
<212> TYPE: DNA
<213> ORGANISM: Artificial
<220> FEATURE:
<223> OTHER INFORMATION: primer

<400> SEQUENCE: 13

```
cgggatcccc atggccgtca tactgtgacg tcgaattccc atggccgtca tactgtgacg     60
tcgaattcga tatcaagctt ggg                                             83
```

<210> SEQ ID NO 14
<211> LENGTH: 78
<212> TYPE: DNA
<213> ORGANISM: Artificial
<220> FEATURE:
<223> OTHER INFORMATION: primer

<400> SEQUENCE: 14

```
tgcactgcag gaattcccat ggccgtcata ctgtgacgtc gaattcccat ggccgtcata     60
ctgtgacgtc ggatcccg                                                   78
```

<210> SEQ ID NO 15
<211> LENGTH: 78
<212> TYPE: DNA
<213> ORGANISM: Artificial
<220> FEATURE:
<223> OTHER INFORMATION: primer

<400> SEQUENCE: 15

```
cgggatccga cgtcacagta tgacggccat gggaattcga cgtcacagta tgacggccat     60
gggaattcct gcagtgca                                                   78
```

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16

```
tcgactgcag cccatggccg tcatactgtg                                      30
```

<210> SEQ ID NO 17
<211> LENGTH: 30
<212> TYPE: DNA
<213> ORGANISM: Artificial
<220> FEATURE:
<223> OTHER INFORMATION: primer

```
<400> SEQUENCE: 17
tgcactgcag gtcggagctg actgttctgg                                              30

<210> SEQ ID NO 18
<211> LENGTH: 264
<212> TYPE: DNA
<213> ORGANISM: Artificial
<220> FEATURE:
<223> OTHER INFORMATION: promoter

<400> SEQUENCE: 18
tcgactgcag cccatggccg tcatactgtg tgacgtcttt cagagcactt tgtgattgct            60
cagtcctaag tataagccct ataaaatgat gggctttgaa atgctggtca gggtagagtg           120
agaagcacca gcaggcagta acagccaacc cttagccatt gctaagggca gagaactggt           180
ggagcctttc tcttactccc aggacttcag cacctaagac agctccaaaa caaaccagaa           240
cagtcagctc cgacctgcag tgca                                                  264

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
tccgagtgtc ccaacaagac t                                                      21

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
ggatcaagat gaggaggatg g                                                      21

<210> SEQ ID NO 21
<211> LENGTH: 17
<212> TYPE: PRT
<213> ORGANISM: Rattus norvegicus
<220> FEATURE:
<221> NAME/KEY: MISC_FEATURE
<222> LOCATION: (1)..(17)
<223> OTHER INFORMATION: Xaa in postions 1 and 11 mean unknown amino
      acid.

<400> SEQUENCE: 21

Xaa Leu Leu Glu Leu Ala Gly Thr Leu Asp Xaa Val Gly Pro Arg Ser
1               5                   10                  15

Pro

<210> SEQ ID NO 22
<211> LENGTH: 151
<212> TYPE: PRT
<213> ORGANISM: Rattus norvegicus

<400> SEQUENCE: 22

Met Leu Leu Leu Leu Leu Leu Leu Leu Gly Pro Gly Ser Cys Leu
1               5                   10                  15

Ser Glu Ala Thr Arg Arg Ser His Val Tyr Lys Arg Gly Leu Leu Glu
                20                  25                  30
```

```
Leu Ala Gly Thr Leu Asp Cys Val Gly Pro Arg Ser Pro Met Ala Tyr
         35                  40                  45

Met Asn Tyr Gly Cys Tyr Cys Gly Leu Gly Gly His Gly Glu Pro Arg
     50                  55                  60

Asp Ala Ile Asp Trp Cys Cys Tyr Tyr His Asp Cys Cys Tyr Ser Gln
 65                  70                  75                  80

Ala Gln Asp Ala Gly Cys Ser Pro Lys Leu Tyr Arg Tyr Pro Trp Lys
                 85                  90                  95

Cys Met Asp His Arg Ile Leu Cys Gly Pro Ala Glu Asn Lys Cys Gln
                100                 105                 110

Glu Leu Leu Cys Arg Cys Asp Glu Thr Leu Ala Tyr Cys Leu Ala Asp
            115                 120                 125

Thr Glu Tyr His Leu Lys Tyr Leu Phe Phe Pro Ser Val Leu Cys Glu
        130                 135                 140

Lys Asp Ser Pro Lys Cys Asn
145                 150

<210> SEQ ID NO 23
<211> LENGTH: 123
<212> TYPE: PRT
<213> ORGANISM: Rattus norvegicus

<400> SEQUENCE: 23

Gly Leu Leu Glu Leu Ala Gly Thr Leu Asp Cys Val Gly Pro Arg Ser
 1               5                  10                  15

Pro Met Ala Tyr Met Asn Tyr Gly Cys Tyr Cys Gly Leu Gly Gly His
             20                  25                  30

Gly Glu Pro Arg Asp Ala Ile Asp Trp Cys Cys Tyr Tyr His Asp Cys
         35                  40                  45

Cys Tyr Ser Gln Ala Gln Asp Ala Gly Cys Ser Pro Lys Leu Tyr Arg
     50                  55                  60

Tyr Pro Trp Lys Cys Met Asp His Arg Ile Leu Cys Gly Pro Ala Glu
 65                  70                  75                  80

Asn Lys Cys Gln Glu Leu Leu Cys Arg Cys Asp Glu Thr Leu Ala Tyr
                 85                  90                  95

Cys Leu Ala Asp Thr Glu Tyr His Leu Lys Tyr Leu Phe Phe Pro Ser
                100                 105                 110

Val Leu Cys Glu Lys Asp Ser Pro Lys Cys Asn
            115                 120

<210> SEQ ID NO 24
<211> LENGTH: 15
<212> TYPE: PRT
<213> ORGANISM: Rattus norvegicus
<220> FEATURE:
<221> NAME/KEY: MISC_FEATURE
<222> LOCATION: (1)..(15)
<223> OTHER INFORMATION: Xaa in postions 11 means unknown amino acid.

<400> SEQUENCE: 24

Gly Leu Leu Glu Leu Ala Gly Thr Leu Asp Xaa Val Gly Pro Arg
 1               5                  10                  15

<210> SEQ ID NO 25
<211> LENGTH: 1020
<212> TYPE: DNA
<213> ORGANISM: Homo sapiens

<400> SEQUENCE: 25
ggccttccaa agtgctggga ttacaggcgt gagtcaccgc gcccggccaa ataaaataaa        60
```

```
atgttaaagc aaattcagga ctacccctcc tccaagtctt ctgttcccctt tgggcgccca    120 ggtgagcggg ggaggggctg ggggagtaat aacatcaaaa gagcgccttt tcctcccctta   180 ttccgaggag acttccctgg gcctgactcc cggtcctgtc cccagcgccc cgcggcctct   240
ggagcccctt cagtgaccaa gatacagaga tcaggacgcc tttgcgccgc cccaggtgcc   300 cgccctagc tggctctgct tgggccgcga gggaaggtga ggtcggggc ggagccgggg    360 cgtgacagcc ggggtgtgtg tccgccgggc ttggtgcctc cggtgccct gcagcaccgt   420 cccacctctg ccaccctccg atggggccgc tacctgtgtg cctgccaatc atgctgctcc   480
tgctactgcc gtcgctgctg ctgctgctgc ttctacctgg ccccgggtcc ggcgaggcct   540
ccaggatatt acgtgtgcac cggcgtggga tcctggaact ggcaggaact gtgggttgtg   600
ttggtccccg aacccccatc gcctatatga aatatggttg cttttgtggc ttgggaggcc   660
atggccagcc ccgcgatgcc attgactggt gctgccatgg ccacgactgt tgttacactc   720
gagctgagga ggccggctgc agccccaaga cagagcgcta ctcctggcag tgcgtcaatc   780
agagcgtcct gtgcggaccg gcagagaaca aatgccaaga actgttgtgc aagtgtgacc   840
aggagattgc taactgctta gcccaaactg agtacaactt aaagtacctc ttctaccccc   900
agttcctatg tgagccggac tcgcccaagt gtgactgact accttgactt gaaatgctct   960
tttgcacaag gaaataaagc gtcctctcag taatgaaaaa aaaaaaaaaa aaaaaaaaa    1020
```

<210> SEQ ID NO 26
<211> LENGTH: 26
<212> TYPE: DNA
<213> ORGANISM: Artificial
<220> FEATURE:
<223> OTHER INFORMATION: primer

<400> SEQUENCE: 26

```
atggggccgc tacctgtgtg cctgcc                                          26
```

<210> SEQ ID NO 27
<211> LENGTH: 25
<212> TYPE: DNA
<213> ORGANISM: Artificial
<220> FEATURE:
<223> OTHER INFORMATION: primer

<400> SEQUENCE: 27

```
tcagtcacac ttgggcgagt ccggc                                           25
```

<210> SEQ ID NO 28
<211> LENGTH: 1040
<212> TYPE: DNA
<213> ORGANISM: Mus musculus

<400> SEQUENCE: 28

```
ctcctcaagg ctccaggtga ccactcctgc ttgactccgc cccacggaaa gaaggtgagg    60 taggggcgg ggctggtggt gggggtcggc aggattggtg agtatactgg ccccttctggt   120 cagtcctaca cctgtcactc tcctatgtgt gggccacctc tgtgacgggc aataatgctg   180
ctgctactgc tgctgttgct gctgggacct ggacccggat tcagcgaagc aaccaggagg   240
tcacatgtat acaagcgtgg actcctggag ctggcaggga ccttggattg tgttgggcct   300
cgatctccga tggcttacat gaactatggc tgttattgtg gccttggtgg ccatggagag   360
ccacgtgacg ccattgactg gtgctgctac caccacgact gctgctactc tcgggctcag   420
gacgctggct gcagccctaa gttagaccgc tacccatgga agtgcatgga ccatcacatc   480
```

```
ctgtgtggac cagcagagaa caaatgccaa gaacttttgt gcaggtgtga cgaggagctg    540
gcttactgcc tggcagggac cgagtaccac ctgaaatacc tcttcttccc ctccatttta    600
tgtgagaagg actctcccaa gtgcaattga caggctcaca tgtccctttg cacatggaaa    660
cgcacttcac tttcagtgat caccaacagc atgcaatttg tgcaggagag tcaccggagt    720
ccaagtgcta agccacctg cgtttgcttt ctccttccat tcaggaactc acaactatga     780
gcctgtggag ttgccagtct gatgaaggtt caaagtcctg ggcctgtttt atacaaatag    840
cgctgtgttg ggcgtggtat acttttgaa attcagcctt tatgagaagc tgtactatct     900
tgtacctgct gcagggctgc tggtcagatg tgggtgaaca cctgcttagg cttggctgtg    960
gtaataacat tgccacatga tacatctaag aattgtaact gtaataaaaa aatgttccct   1020
aaaaaaaaaa aaaaaaaaaa                                               1040
```

<210> SEQ ID NO 29
<211> LENGTH: 25
<212> TYPE: DNA
<213> ORGANISM: Artificial
<220> FEATURE:
<223> OTHER INFORMATION: primer

<400> SEQUENCE: 29
atgctgctgc tactgctgct gttgc                                            25

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
tcaattgcac ttgggagagt ccttc                                            25

<210> SEQ ID NO 31
<211> LENGTH: 33
<212> TYPE: DNA
<213> ORGANISM: Artificial
<220> FEATURE:
<223> OTHER INFORMATION: primer

<400> SEQUENCE: 31
gatatcgccg ccaccatggg gccgctacct gtg                                   33

<210> SEQ ID NO 32
<211> LENGTH: 45
<212> TYPE: DNA
<213> ORGANISM: Artificial
<220> FEATURE:
<223> OTHER INFORMATION: primer

<400> SEQUENCE: 32
gatatctcaa tggtgatggt gatgatggtc acacttgggc gagtc                      45

<210> SEQ ID NO 33
<211> LENGTH: 33
<212> TYPE: DNA
<213> ORGANISM: Artificial
<220> FEATURE:
<223> OTHER INFORMATION: primer

<400> SEQUENCE: 33
gatatcgccg ccaccatgct gctgctactg ctg                                   33

<210> SEQ ID NO 34
<211> LENGTH: 45
<212> TYPE: DNA
<213> ORGANISM: Artificial
<220> FEATURE:
<223> OTHER INFORMATION: primer

<400> SEQUENCE: 34
gatatctcaa tggtgatggt gatgatgatt gcacttggga gagtc        45

<210> SEQ ID NO 35
<211> LENGTH: 122
<212> TYPE: PRT
<213> ORGANISM: Homo sapiens

<400> SEQUENCE: 35

Gly Ile Leu Glu Leu Ala Gly Thr Val Gly Cys Val Gly Pro Arg Thr
1               5                   10                  15

Pro Ile Ala Tyr Met Lys Tyr Gly Cys Phe Cys Gly Leu Gly Gly His
            20                  25                  30

Gly Gln Pro Arg Asp Ala Ile Asp Trp Cys Cys His Gly His Asp Cys
        35                  40                  45

Cys Tyr Thr Arg Ala Glu Glu Ala Gly Cys Ser Pro Lys Thr Glu Arg
    50                  55                  60

Tyr Ser Trp Gln Cys Val Asn Gln Ser Val Leu Cys Gly Pro Ala Glu
65                  70                  75                  80

Asn Lys Cys Gln Glu Leu Leu Cys Cys Asp Gln Glu Ile Ala Asn Cys
                85                  90                  95

Leu Ala Gln Thr Glu Tyr Asn Leu Lys Tyr Leu Phe Tyr Pro Gln Phe
            100                 105                 110

Leu Cys Glu Pro Asp Ser Pro Lys Cys Asp
        115                 120

<210> SEQ ID NO 36
<211> LENGTH: 123
<212> TYPE: PRT
<213> ORGANISM: Mus musculus

<400> SEQUENCE: 36

Gly Leu Leu Glu Leu Ala Gly Thr Leu Asp Cys Val Gly Pro Arg Ser
1               5                   10                  15

Pro Met Ala Tyr Met Asn Tyr Gly Cys Tyr Cys Gly Leu Gly Gly His
            20                  25                  30

Gly Glu Pro Arg Asp Ala Ile Asp Trp Cys Cys Tyr His His Asp Cys
        35                  40                  45

Cys Tyr Ser Arg Ala Gln Asp Ala Gly Cys Ser Pro Lys Leu Asp Arg
    50                  55                  60

Tyr Pro Trp Lys Cys Met Asp His His Ile Leu Cys Gly Pro Ala Glu
65                  70                  75                  80

Asn Lys Cys Gln Glu Leu Leu Cys Arg Cys Asp Glu Glu Leu Ala Tyr
                85                  90                  95

Cys Leu Ala Gly Thr Glu Tyr His Leu Lys Tyr Leu Phe Phe Pro Ser
            100                 105                 110

Ile Leu Cys Glu Lys Asp Ser Pro Lys Cys Asn
        115                 120

<210> SEQ ID NO 37
<211> LENGTH: 456

```
<212> TYPE: DNA
<213> ORGANISM: Rattus norvegicus

<400> SEQUENCE: 37
atgctgctgc tactgctgct gttgctactg ggacctggat cctgtctcag cgaagcaacc      60
aggaggtcac atgtgtacaa gcgtggactc ctggaactgg cagggacctt ggattgtgtt     120
ggtcctcgat cgccgatggc ttacatgaac tatggttgtt attgtggcct tggtggccac     180
ggagagccac gtgatgccat tgactggtgc tgctactacc atgactgctg ctactctcag     240
gctcaggatg ccggctgcag ccccaagcta taccgatacc cgtggaagtg catggaccat     300
cgcatcctgt gtggaccggc agagaacaaa tgccaagaac tcctatgcag gtgtgatgag     360
acgctcgcat actgcctggc agacacagag taccacctga atacctcttt cttcccctcg     420 gtttatgtg agaaggactc acccaagtgc aactaa                                456

<210> SEQ ID NO 38
<211> LENGTH: 441
<212> TYPE: DNA
<213> ORGANISM: Sus scrofa

<400> SEQUENCE: 38
atgaaattcc tcgtgttggc tgttctgctc acagtgggcg ctgcccagga aggcatcagc      60
tcaagggcat tatggcagtt tcgtagcatg attaagtgcg caatccccgg cagtcacccc     120
ttgatggatt tcaacaacta tggctgctac tgtggcctag gtggatcagg acccctgtg      180 gatgaactgg acaggtgctg cgagacacac gacaactgct acagagatgc caagaacctg     240
gacagctgta aattcctcgt ggacaatccc tacaccgaaa gctactccta tcatgttct      300 aacactgaga tcacctgcaa cagcaaaaac aatgcttgtg aggccttcat ctgtaactgt     360
gaccgaaatg ctgccatttg cttctcaaag gccccataca caaggagca caagaacctg      420 gacaccaaga agtactgtta g                                              441

<210> SEQ ID NO 39
<211> LENGTH: 124
<212> TYPE: PRT
<213> ORGANISM: Sus scrofa

<400> SEQUENCE: 39

Ala Leu Trp Gln Phe Arg Ser Met Ile Lys Cys Ala Ile Pro Gly Ser
1               5                   10                  15

His Pro Leu Met Asp Phe Asn Asn Tyr Gly Cys Tyr Cys Gly Leu Gly
            20                  25                  30

Gly Ser Gly Thr Pro Val Asp Glu Leu Asp Arg Cys Cys Glu Thr His
        35                  40                  45

Asp Asn Cys Tyr Arg Asp Ala Lys Asn Leu Asp Ser Cys Lys Phe Leu
    50                  55                  60

Val Asp Asn Pro Tyr Thr Glu Ser Tyr Ser Tyr Ser Cys Ser Asn Thr
65                  70                  75                  80

Glu Ile Thr Cys Asn Ser Lys Asn Asn Ala Cys Glu Ala Phe Ile Cys
                85                  90                  95

Asn Cys Asp Arg Asn Ala Ala Ile Cys Phe Ser Lys Ala Pro Tyr Asn
            100                 105                 110

Lys Glu His Lys Asn Leu Asp Thr Lys Lys Tyr Cys
        115                 120

<210> SEQ ID NO 40
<211> LENGTH: 504
```

<212> TYPE: DNA
<213> ORGANISM: Apis mellifera

<400> SEQUENCE: 40

| | | |
|---|---|---|
| atgcaagtcg ttctcggatc cttgttcctt ctcctcctct ctacctctca cggatggcaa | 60 |
| atcagggata ggatcgggga taacgagttg gaggaacgga taatatatcc aggaacgtta | 120 |
| tggtgcgggc atggtaacaa gtcgtccggc ccgaacgagc taggtcggtt caagcacacg | 180 |
| gatgcatgct gtcgaaccca cgacatgtgc ccggacgtga tgtcagctgg tgaatcgaag | 240 |
| cacggcctga ccaacacggc ctcccacacc aggttgtcgt gcgactgcga cgacaagttc | 300 |
| tatgattgtc ttaaaaattc ggcggacacg attagctcgt atttcgtagg gaagatgtac | 360 |
| ttcaatctga tagacacgaa gtgttacaaa ctggagcatc ctgtcaccgg gtgcggtgag | 420 |
| agaaccgagg gtcgttgtct tcactacacc gtggacaaaa gcaaaccgaa agtgtaccaa | 480 |
| tggttcgatc ttcgcaagta ttga | 504 |

<210> SEQ ID NO 41
<211> LENGTH: 134
<212> TYPE: PRT
<213> ORGANISM: Apis mellifera

<400> SEQUENCE: 41

Ile Ile Tyr Pro Gly Thr Leu Trp Cys Gly His Gly Asn Lys Ser Ser
1               5                   10                  15

Gly Pro Asn Glu Leu Gly Arg Phe Lys His Thr Asp Ala Cys Cys Arg
            20                  25                  30

Thr His Asp Met Cys Pro Asp Val Met Ser Ala Gly Glu Ser Lys His
        35                  40                  45

Gly Leu Thr Asn Thr Ala Ser His Thr Arg Leu Ser Cys Asp Cys Asp
    50                  55                  60

Asp Lys Phe Tyr Asp Cys Leu Lys Asn Ser Ala Asp Thr Ile Ser Ser
65                  70                  75                  80

Tyr Phe Val Gly Lys Met Tyr Phe Asn Leu Ile Asp Thr Lys Cys Tyr
                85                  90                  95

Lys Leu Glu His Pro Val Thr Gly Cys Gly Glu Arg Thr Glu Gly Arg
            100                 105                 110

Cys Leu His Tyr Thr Val Asp Lys Ser Lys Pro Lys Val Tyr Gln Trp
        115                 120                 125

Phe Asp Leu Arg Lys Tyr
    130

<210> SEQ ID NO 42
<211> LENGTH: 48
<212> TYPE: DNA
<213> ORGANISM: Artificial
<220> FEATURE:
<223> OTHER INFORMATION: primer

<400> SEQUENCE: 42
gatatctcac ttgtcatcgt cgtccttgta gtcgtcacac ttgggcga                48

<210> SEQ ID NO 43
<211> LENGTH: 522
<212> TYPE: DNA
<213> ORGANISM: Homo sapiens

<400> SEQUENCE: 43
atggggccgc tacctgtgtg cctgccaatc atgctgctcc tgctactgcc gtcgctgctg    60

-continued

```
ctgctgctgc ttctacctgg ccccgggtcc ggcgaggcct ccaggatatt acgtgtgcac    120
cggcgtggga tcctggaact ggcaggaact gtgggttgtg ttggtccccg aaccccatc    180 gcctatatga aatatggttg cttttgtggc ttgggaggcc atggccagcc ccgcgatgcc    240
attgactggt gctgccatgg ccacgactgt tgttacactc gagctgagga ggccggctgc    300
agccccaaga cagagcgcta ctcctggcag tgcgtcaatc agagcgtcct gtgcggaccg    360
gcagagaaca aatgccaaga actgttgtgc aagtgtgacc aggagattgc taactgctta    420
gcccaaactg agtacaactt aaagtacctc ttctaccccc agttcctatg tgagccggac    480
tcgcccaagt gtgacgacta caaggacgac gatgacaagt ga                      522
```

<210> SEQ ID NO 44
<211> LENGTH: 48
<212> TYPE: DNA
<213> ORGANISM: Artificial
<220> FEATURE:
<223> OTHER INFORMATION: primer

<400> SEQUENCE: 44

```
gatatctcac ttgtcatcgt cgtccttgta gtcattgcac ttgggaga             48
```

<210> SEQ ID NO 45
<211> LENGTH: 480
<212> TYPE: DNA
<213> ORGANISM: Mus musculus

<400> SEQUENCE: 45

```
atgctgctgc tactgctgct gttgctgctg ggacctggac ccggattcag cgaagcaacc    60
aggaggtcac atgtatacaa gcgtggactc ctggagctgg cagggacctt ggattgtgtt    120
gggcctcgat ctccgatggc ttacatgaac tatggctgtt attgtggcct tggtggccat    180
ggagagccac gtgacgccat tgactggtgc tgctaccacc acgactgctg ctactctcgg    240
gctcaggacg ctggctgcag ccctaagtta gaccgctacc catggaagtg catgaccat    300 cacatcctgt gtggaccagc agagaacaaa tgccaagaac ttttgtgcag gtgtgacgag    360
gagctggctt actgcctggc agggaccgag taccacctga aatacctctt cttcccctcc    420
attttatgtg agaaggactc tcccaagtgc aatgactaca aggacgacga tgacaagtga    480
```

<210> SEQ ID NO 46
<211> LENGTH: 19
<212> TYPE: DNA
<213> ORGANISM: Artificial
<220> FEATURE:
<223> OTHER INFORMATION: primer

<400> SEQUENCE: 46

```
tgatccagaa cttccggca                                                  19
```

<210> SEQ ID NO 47
<211> LENGTH: 19
<212> TYPE: DNA
<213> ORGANISM: Artificial
<220> FEATURE:
<223> OTHER INFORMATION: primer

<400> SEQUENCE: 47

```
cggagttggc aaacgtgaa                                                  19
```